United States Patent [19]
Kondo et al.

[11] Patent Number: 5,849,524
[45] Date of Patent: Dec. 15, 1998

[54] TRANSFORMATION SYSTEMS FOR THE YEAST *CANDIDA UTILIS* AND THE EXPRESSION OF HETEROLOGOUS GENES THEREWITH

[75] Inventors: Keiji Kondo, Yokohama; Susumu Kajiwara, Tokyo-to; Norihiko Misawa, Yokohama, all of Japan

[73] Assignee: Kirin Beer Kabushiki Kaisha, Tokyo, Japan

[21] Appl. No.: 557,128

[22] PCT Filed: May 25, 1995

[86] PCT No.: PCT/JP95/01005

§ 371 Date: May 24, 1996

§ 102(e) Date: May 24, 1996

[87] PCT Pub. No.: WO95/32289

PCT Pub. Date: Nov. 30, 1995

[30] Foreign Application Priority Data

| | | | |
|---|---|---|---|
| May 25, 1994 | [JP] | Japan | 6-135015 |
| Oct. 26, 1994 | [JP] | Japan | 6-285823 |
| Apr. 28, 1995 | [JP] | Japan | 7-129287 |

[51] Int. Cl.⁶ ...... C12P 21/02
[52] U.S. Cl. ...... 435/69.1; 435/71.1; 435/172.3; 435/173.5; 435/320.1; 435/254.22; 536/23.1; 536/24.1; 536/24.2
[58] Field of Search ...... 435/69.1, 172.3, 435/320.1, 254, 71.1, 254.22, 173.5; 536/23.4, 24.1, 24.2

[56] References Cited

U.S. PATENT DOCUMENTS 5,436,136  7/1995  Hinnen et al. ............ 435/69.1

FOREIGN PATENT DOCUMENTS 1-42573  9/1969  Japan .
4-66089  3/1992  Japan .

OTHER PUBLICATIONS

Rose et al. Methods in Enzymology, vol. 194, pp.199–206, 1991.
Hsu et al. Journal of Bacteriology, vol. 154(3), pp. 1033–1039, Jun. 1991.
Rothstein, R. Methods in Enzymology, vol. 194, pp.281–301, 1991.
Dehoux et al. European Journal of Biochemistry, vol. 213, pp. 841–848,1993.
Kawai et al. Journal of Bacteriology, vol. 173(1), pp. 254–262, 1992.
Lopes et al. Gene, vol. 79, pp. 199–206, 1989.
Russel et al. Biochemica et Biophysica Acta, vol. 1008, pp. 243–246, 1989.
Becker et al. Methods in Enzymology, vol. 194, pp. 281–301, 1991.

*Primary Examiner*—James Ketter
*Assistant Examiner*—Irem Yucel
*Attorney, Agent, or Firm*—Foley & Lardner

[57] ABSTRACT

An reproducible transformation system of a yeast of *Candida utilis*, a process for expressing a heterologous gene in the transformation system, a vector which can be used in the transformation system and the expression method, and a novel DNA group are disclosed. In particular, the process for expressing a heterologous gene in *Candida utilis* comprises transforming *Candida utilis* with a vector comprising a drug-resistance marker, a sequence homologous to the chromosomal DNA of the *Candida utilis* yeast, and the heterologous gene, culturing the transformant, and isolating the expression product of the heterologous gene.

101 Claims, 50 Drawing Sheets

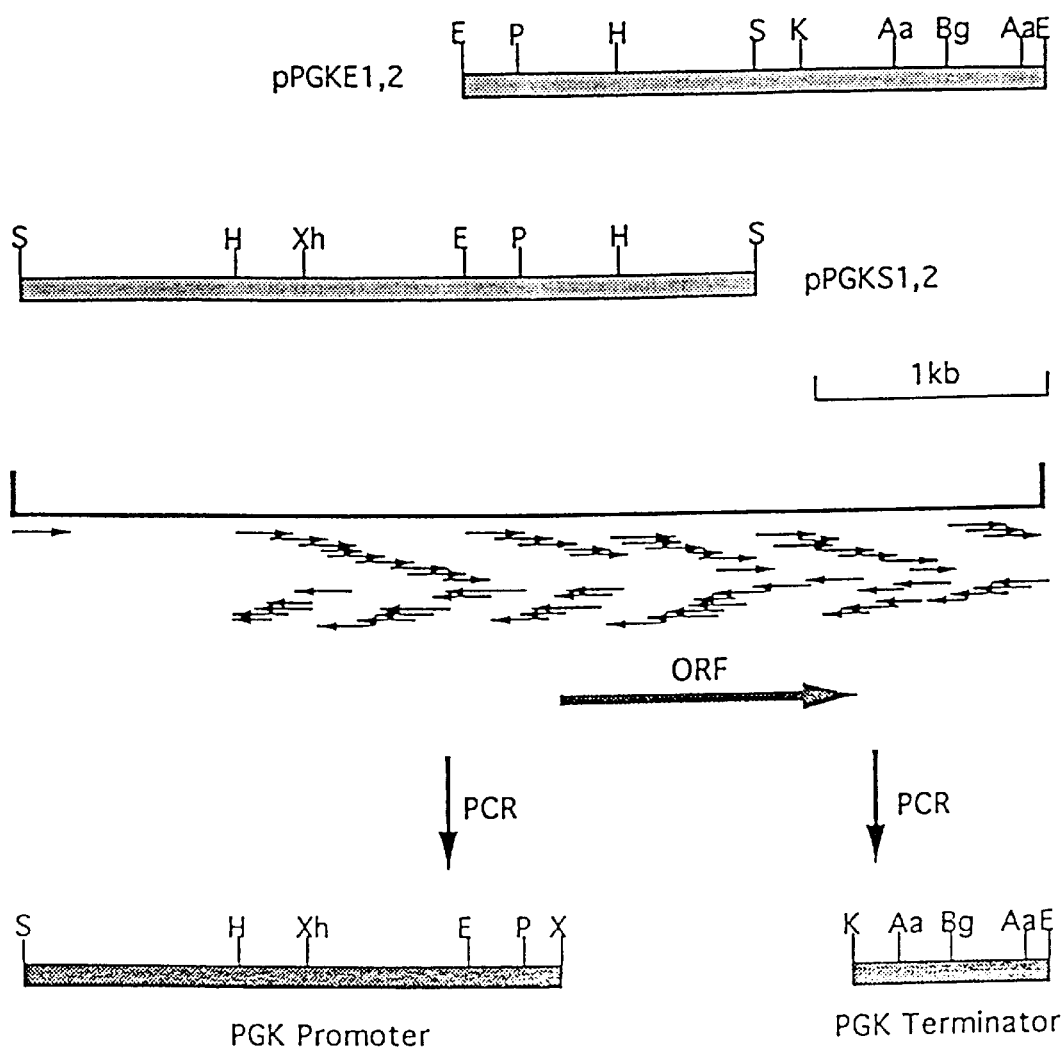
F I G. 1

```
  1 CTGCAAGCTA CTTTGTAATT AAACAAATAA CGGGATTATA TGTCAATATC ATTATGATTA
 61 TTTAGGAAAA CATGTAGACC TTACCCGATG CACCTCCACC AACAAGCCAA TTCTGGGTGG
121 GATGGAAGTT ACACACTGCT GGTACGTTGG TCACCAGTGG GTTTGACAAA TGTGCCAGCT
181 GATGACCATC TCGGTCGTAG ACGTCAAAGT ACTTGTTCAT ATTGGCAATG ACAAACTTTT
241 CTTTATCCGG GGTATATTGC TGCCACCTTG CCTTCAAAAT GGATACCCAT CTTCCCGTTT
301 GACAGTTGTG TTTGATACGA TGACTTGGGG TCAAATCACC TTCAATAGCG AAGTTCTTAG
361 GTTTAGTGCT GATGTCCTCA CCAAGATTGA AGATGTTAAC TGTGTCATCG TAACCGTTAC
421 AAACAAGGTC ACCAGATCTA TTCCAATCCA CGATGGAAAC TGACAATCTT GAATCATAGA
481 CGCCAACAGT GTGAAGAGTC TCCAGGTTAT CATCCCATTC ATCCCAATCA CACGTAGTTA
541 CTGTTCTTAG ATCCCAAACC TTCAAAGTTC GATCCAATGA GGCAGTAGCA ATCTGGTTCT
601 TATTCATCGG ATTGGTAGTG AATCCACCAA TCTTTTTATT CGACAATCTC AAAACTTGTC
661 TTCTTGAGTG ATCGCCTGCT CTTAGGTCAA TTCTGCTGAA TTGTCCTTGC ATTGTTGTGT
721 AGTACATTTC ATTGTCGTTG TTGTAATTTA TGTCAGTGAT ACCGACGTCA AAGTCGTTGA
781 TGAATAACTG TGAGGACTTC ATGGAGCGTA GATCNATTGA GCGAATGGAC CCATCATACG
841 ATGCACTGTA GACCTTCGTC GTGTCATTCA TGTTGAATTC
```

FIG. 2

```
   1 AAGCTTTTGT CTTTTAGGAG CCTTCTTTTC ACCCTGGCTT TCTTCAGACT CCACGCCTCT
  61 CGCCCGTTTG TTGTTGATCT TCTTCTGTTG CTTCTTCGTG AGCTTACCAG TATCCAGATG
 121 CGTTGTCAGG GCAAGAGGGT CATGTTCAAG CTCCTCTTTC ACTTTCAGTC CAATACGTTT
 181 CCAGGCAGGG ATGTGTTCGC TCATCGTTCC AGACTCGAGT GGTGAAAACT ATGGCAACCT
 241 CTACTTCCTT TCCAAACACA CAGCGTGCTT TGTAGTGTGT GCCTAAGAGC TGAATTTTTT
 301 TTCCTTCCAT GCTGCGCTGC GATGAGCTCT GCCCGCCCGC AGCCTCGGAG CTAGCGACG
 361 TATAAAAAAG GCCTGTGAAA ATTTTATCCT CCTCCTTAAC GACCCTTCTT TCTCTTCTTC
 421 ACATTCAAAA ACTTCAAGCA GCTGTCTCTG TTCCTTTGCT GTGTTCTACC ATTGGATATT
 481 CCCATTCCCC GTGGAGAACC GAACTGGAGT CTAGCAGCAT GCGAGATCAA TATTACACGG
 541 TTTGAGTCTG ATACGCTTGA GCAGCCATTT TTTGGCTTCT CCTGGTGTGT ATCCAGATAT
 601 AGAAGTTCGT ATACATTTCC CATAGCGATT GTAAAATGAT TCTGCAATGG AACCATCCGT
 661 AATTGTAGGC CTGCTGAGAT GGCACTCGCA ATGCCTCTGT GTCTGGTTTT TTGCCTTCTC
 721 CGTCCATCAG CACCAGTGGC TTCTTAGGGC ATAACGAGAC GGCTCCTTGG TGAAAGATGC
 781 CCTGCTCCGT CTGTCTGCCT GTTGCTACAA CCACTGCGTA GTCAGATGAC CCGGTCTGTG
 841 TGCTGTGGAA TCACCGGGAG CGAAATTCCG GTTTCGCTGG CAGATGAGCT CATCAACCAC
 901 ATCAACTGGA GCAACCTCAC CAGAGGACAC GTAACCTGCC CGGTTGAATT CTGTCAAACC
 961 GTACATCACA CAACAACAGC AGCAGCAACA ACAACAACGT CAGTTGTCGT TCGCATGGCG
1021 ACGTTACCTA ACGGCACCAA CATCGTCTCG TCCTCGCCAA TGCCTGTTTC CCCTACCCGG
1081 AGTGGCCCGG CCCACCTGTC GTTCTTTTTT CGTCAATTGT GTCCAGCTGG TGCCATCACC
1141 ATATGTTCAA GTGCGTGGCC TGTACTAGCG CAGTCTGCTG CAGTATAAAA GGGATTGCTG
1201 AGGCCCCCTT TAGCGTTTCC AATTAACAAT TGATTCCCTT TTCCCCATAG TCCGTTTGTA
1261 CTACATCCTA CATAACAAAA GTGAGTGTTA CAAGACAAGT GTGGCGGTCA ATTGGATCAT
1321 TTGGACTAAC ATACTGGCGG ATAAAG
```

FIG. 3

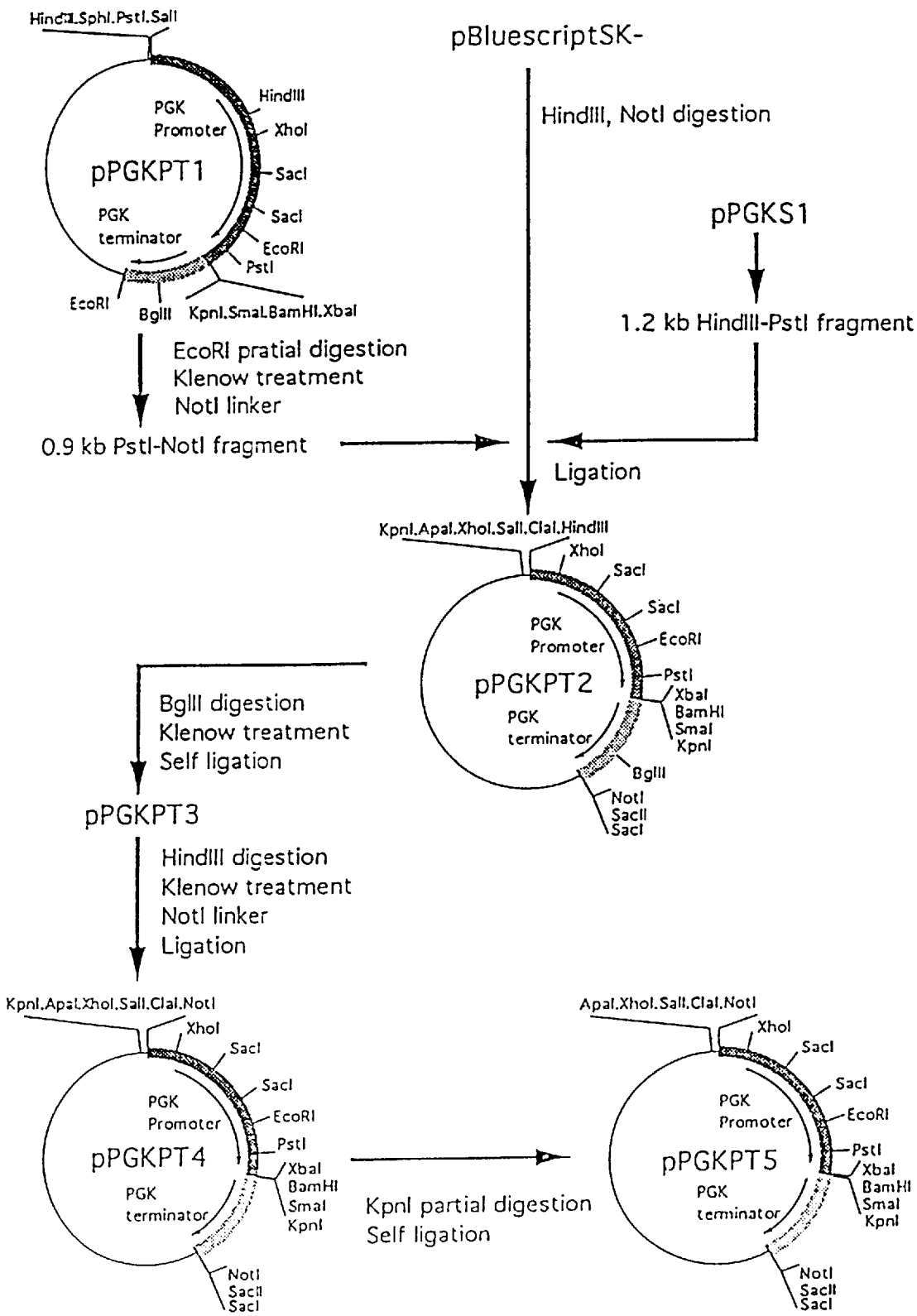
F I G. 4

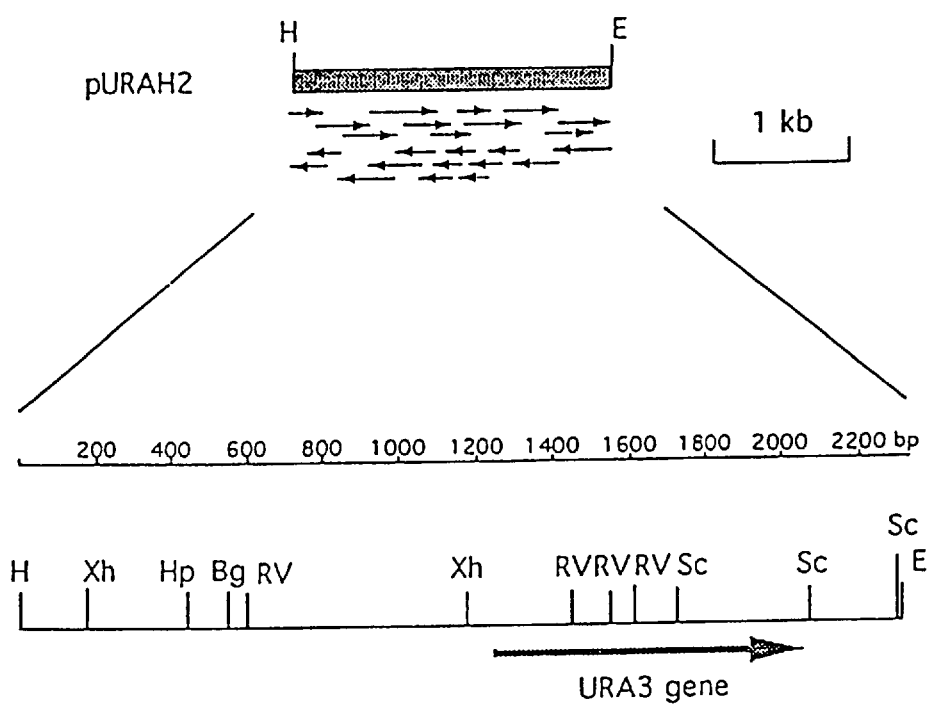
F I G. 8

```
   1 AAGCTTATGG AGGAGATTGG GAAGATTGAA CGAGGTGAGA TGGACACGTT GCTGATTGAC
  61 GAGATCGGCA AGAAGGAGGC ACCTGTGGTG AAACCACTTA CACCCGACGT GGATAGTAAT
 121 GTAACAGGGG AACCGACTGG ACATAGTTCT ACGACACCAC CACCGGTGGA ACAGGACTCG
 181 AGCACAACCA CGAGGAAGAG AGCACAAGAC GATGGTGAGG AAAACACAAG GAAGAAGCCC
 241 AAGGTTGAGG CAGAGAAAAA GGCAGAGCAA GAGGCAGAGA AAGAGGCAGA GAAAGAGGCA
 301 GAGAAAGAGG CAGAGCAAGA GGCAGAGAAA GAGGCTCCGC GTGCAGTGCC GAACAAGAGA
 361 CTACAACACA TTGCTACTCC TCTCATCGAG AGCATCTCGT CATACAAGTA CGCCTCAGCG
 421 TTTCTACACC CTGTTAACGA GTCCAGTGCA CCCAACTATT ACTCTCTGAT CAAGAAACCA
 481 AGGGATCTGA AGACCATCAA ACAGATGGTC AAGGACGGAC GTATACAGAC CAATCTTGAG
 541 CTGGAGAGGG AGATCTTGCT GATGTTTGCC AATGCCATCA TGTACAACAA GACCGGGACG
 601 GATATCTACG AGTGGACCAA GGAGATGCAG CCGGAAGTTG ACAAGCTCAT CGAGCTGTTT
 661 AACGAGAGTA AATAGGATAC AGGCTAGAGA TCAAAAGAAG AATAGAAACA GCTCGATAAA
 721 ACGGTATTGT AAGTGGTATG TACAAAGGGG TGTGTCTTGC TCAACGTCTT TGCATCTGCT
 781 GAGTCAAAGC AGCGTTCTGC TCTTGGAATC TAAGACCGAC TCTTTCCGAA TGCTTGAGGA
 841 ACTTTTCAGA GCACTTCAAC ACACAGGATT CCTCCTTTGA TGATAGCTTT TCAGAGGTGA
 901 AGTCGTTGAC ACAGTCGCTG AAACAACGCT CAACGAGGTT GGAATAAAGA CGCATAAAGT
 961 CCTTCATCTG CTTCTGCTCA ACAAGCTGCT GGAACTGCTG CTGCTCTTTT GGGTTCAATT
1021 GGTCCATCCT TGCTACTTTT CCGCCTAGTT TCGATTCCGA TTCTGATAGA AAGCCCAGC
1081 TATGAATGGA AGAAATTTTT CACTTTTGTA TGTCCTTTTT TTCACGCTTC GTTGCTTCGG
1141 ACAAAAAAAT AGTGGAGGCA CTCGGTGGAG GGAAGCTATC CTCGAGATGA AAAATTTCAA
1201 GCTCATCTCA TCGTCCAAGT GGGACAGCAA GCTGAGGCTT CTGAAGAGGT TGAGGAAAAT
1261 GGTCACCACG TTATCGTACA CAGAGAGGGC ATCGCAGCAC CCTTCGCCAC TTGCTAAGCG
1321 TCTGTTTTCG CTTATGGAGT CCAAGAAGAC GAACCTGTGT GCCAGTGTCG ATGTTCGTAC
1381 CACAGAGGAG TTGCTCAAGC TCGTTGATAC GCTTGGTCCT TATATCTGTC TGTTGAAGAC
1441 GCATATTGAT ATCATTGATG ACTTCTCTAT GGAGTCTACT GTGGCTCCAC TGTTGGAGCT
1501 TTCAAAGAAG CACAATTTCC TCATCTTTGA GGACCGTAAG TTTGCTGATA TCGGCAACAC
1561 CGTCAAGGCA CAGTACGCCG GTGGTGCGTT CAAGATTGCG CAATGGGCAG ATATCACCAA
1621 CGCCCACGGT GTCACCGGTG CAGGTATCGT CAAGGGGTTA AAGGAGGCTG CACAGGAAAC
1681 CACGGATGAG CCAAGAGGGC TGTTGATGCT TGCGGAGCTG AGCTCCAAGG GCTCCTTGGC
1741 CCACGGGACA TATACCGAGG AGACCGTGGA GATTGCCAAA ACTGATAAGG ACTTTTGTAT
1801 TGGATTCATC GCACAGAGAG ACATGGGTGG CAGAGAAGAT GGGTTCGACT GGATCATCAT
1861 GACACCAGGC GTGGGACTCG ACGATAAGGG CGACTCCCTG GCCAACAGT ACAGAACTGT
1921 CGATGAGGTT GTCAGTGGTG GCTCTGACAT CATCATCGTT GGTAGAGGCT TGTTTGGAAA
1981 GGGAAGAGAT CCAACAGTGG AAGGTGAGCG TTATAGAAAA GCAGGCTGGG ATGCTTATCT
2041 CAAGAGATGC TCAGCTCAAT AAGCGTTGAG CTCTGGCTTG TATAGGTTCA CTTGTATAAA
2101 ATGTTCATTA CTGTTTTCGG AAGTTGTAGA TTGCCATTTT TGCGCAAATT GACGCCAGTC
2161 TTTTTTTGCG CCAAATGTCA GTTTTTTTGC GCCAAAATTT ACTTCATCTT ATACAACTGC
2221 AAAAACCATC CAATCCAATC CAGAAAGGAC TGATCAATGG TGGTGATTGA CTCAAGTTCT
2281 GATGCTACAC AACAGACAGA GCTCTCTAAA AAGAATTCGA TATCAAGCTT
```

FIG. 9

```
1260         1270         1280         1290         1300
  *    *    *    *    *    *    *    *    *    *
ATG GTC ACC ACG TTA TCG TAC ACA GAG AGG GCA TCG CAG CAC CCT TCG
Met Val Thr Thr Leu Ser Tyr Thr Glu Arg Ala Ser Gln His Pro Ser
     1310         1320         1330         1340         1350
       *    *    *    *    *    *    *    *    *
CCA CTT GCT AAG CGT CTG TTT TCG CTT ATG GAG TCC AAG AAG ACG AAC
Pro Leu Ala Lys Arg Leu Phe Ser Leu Met Glu Ser Lys Lys Thr Asn
     1360         1370         1380         1390         1400
  *    *    *    *    *    *    *    *    *    *
CTG TGT GCC AGT GTC GAT GTT CGT ACC ACA GAG GAG TTG CTC AAG CTC
Leu Cys Ala Ser Val Asp Val Arg Thr Thr Glu Glu Leu Leu Lys Leu
          1410         1420         1430         1440         1450
       *    *    *    *    *    *    *    *    *
GTT GAT ACG CTT GGT CCT TAT ATC TGT CTG TTG AAG ACG CAT ATT GAT
Val Asp Thr Leu Gly Pro Tyr Ile Cys Leu Leu Lys Thr His Ile Asp
               1460         1470         1480         1490
       *    *    *    *    *    *    *    *    *
ATC ATT GAT GAC TTC TCT ATG GAG TCT ACT GTG GCT CCA CTG TTG GAG
Ile Ile Asp Asp Phe Ser Met Glu Ser Thr Val Ala Pro Leu Leu Glu
1500         1510         1520         1530         1540
  *    *    *    *    *    *    *    *    *    *
CTT TCA AAG AAG CAC AAT TTC CTC ATC TTT GAG GAC CGT AAG TTT GCT
Leu Ser Lys Lys His Asn Phe Leu Ile Phe Glu Asp Arg Lys Phe Ala
     1550         1560         1570         1580         1590
       *    *    *    *    *    *    *    *    *
GAT ATC GGC AAC ACC GTC AAG GCA CAG TAC GCC GGT GGT GCG TTC AAG
Asp Ile Gly Asn Thr Val Lys Ala Gln Tyr Ala Gly Gly Ala Phe Lys
          1600         1610         1620         1630         1640
       *    *    *    *    *    *    *    *    *
ATT GCG CAA TGG GCA GAT ATC ACC AAC GCC CAC GGT GTC ACC GGT GCA
Ile Ala Gln Trp Ala Asp Ile Thr Asn Ala His Gly Val Thr Gly Ala
               1650         1660         1670         1680         1690
       *    *    *    *    *    *    *    *    *    *
GGT ATC GTC AAG GGG TTG AAG GAG GCT GCA CAG GAA ACC ACG GAT GAG
Gly Ile Val Lys Gly Leu Lys Glu Ala Ala Gln Glu Thr Thr Asp Glu
                    1700         1710         1720         1730
       *    *    *    *    *    *    *    *    *
CCA AGA GGG CTG TTG ATG CTT GCG GAG CTG AGC TCC AAG GGC TCC TTG
Pro Arg Gly Leu Leu Met Leu Ala Glu Leu Ser Ser Lys Gly Ser Leu
1740         1750         1760         1770         1780
  *    *    *    *    *    *    *    *    *    *
GCC CAC GGG ACA TAT ACC GAG GAG ACC GTG GAG ATT GCC AAA ACT GAT
Ala His Gly Thr Tyr Thr Glu Glu Thr Val Glu Ile Ala Lys Thr Asp
```

FIG. 10

```
        1790        1800        1810        1820        1830
          *     *     *     *     *     *     *     *     *
        AAG GAC TTT TGT ATT GGA TTC ATC GCA CAG AGA GAC ATG GGT GGC AGA
        Lys Asp Phe Cys Ile Gly Phe Ile Ala Gln Arg Asp Met Gly Gly Arg
            1840        1850        1860        1870        1880
          *     *     *     *     *     *     *     *     *     *
        GAA GAT GGG TTC GAC TGG ATC ATC ATG ACA CCA GGC GTG GGA CTC GAC
        Glu Asp Gly Phe Asp Trp Ile Ile Met Thr Pro Gly Val Gly Leu Asp
            1890        1900        1910        1920        1930
          *     *     *     *     *     *     *     *     *     *
        GAT AAG GGC GAC TCC CTG GGC CAA CAG TAC AGA ACT GTC GAT GAG GTT
        Asp Lys Gly Asp Ser Leu Gly Gln Gln Tyr Arg Thr Val Asp Glu Val
            1940        1950        1960        1970
          *     *     *     *     *     *     *     *     *
        GTC AGT GGT GGC TCT GAC ATC ATC ATC GTT GGT AGA GGC TTG TTT GGA
        Val Ser Gly Gly Ser Asp Ile Ile Ile Val Gly Arg Gly Leu Phe Gly
        1980        1990        2000        2010        2020
          *     *     *     *     *     *     *     *     *     *
        AAG GGA AGA GAT CCA ACA GTG GAA GGT GAG CGT TAT AGA AAA GCA GGC
        Lys Gly Arg Asp Pro Thr Val Glu Gly Glu Arg Tyr Arg Lys Ala Gly
            2030        2040        2050
          *     *     *     *     *     *
        TGG GAT GCT TAT CTC AAG AGA TGC TCA GCT CAA TAA
        Trp Asp Ala Tyr Leu Lys Arg Cys Ser Ala Gln ***
```

FIG. 11

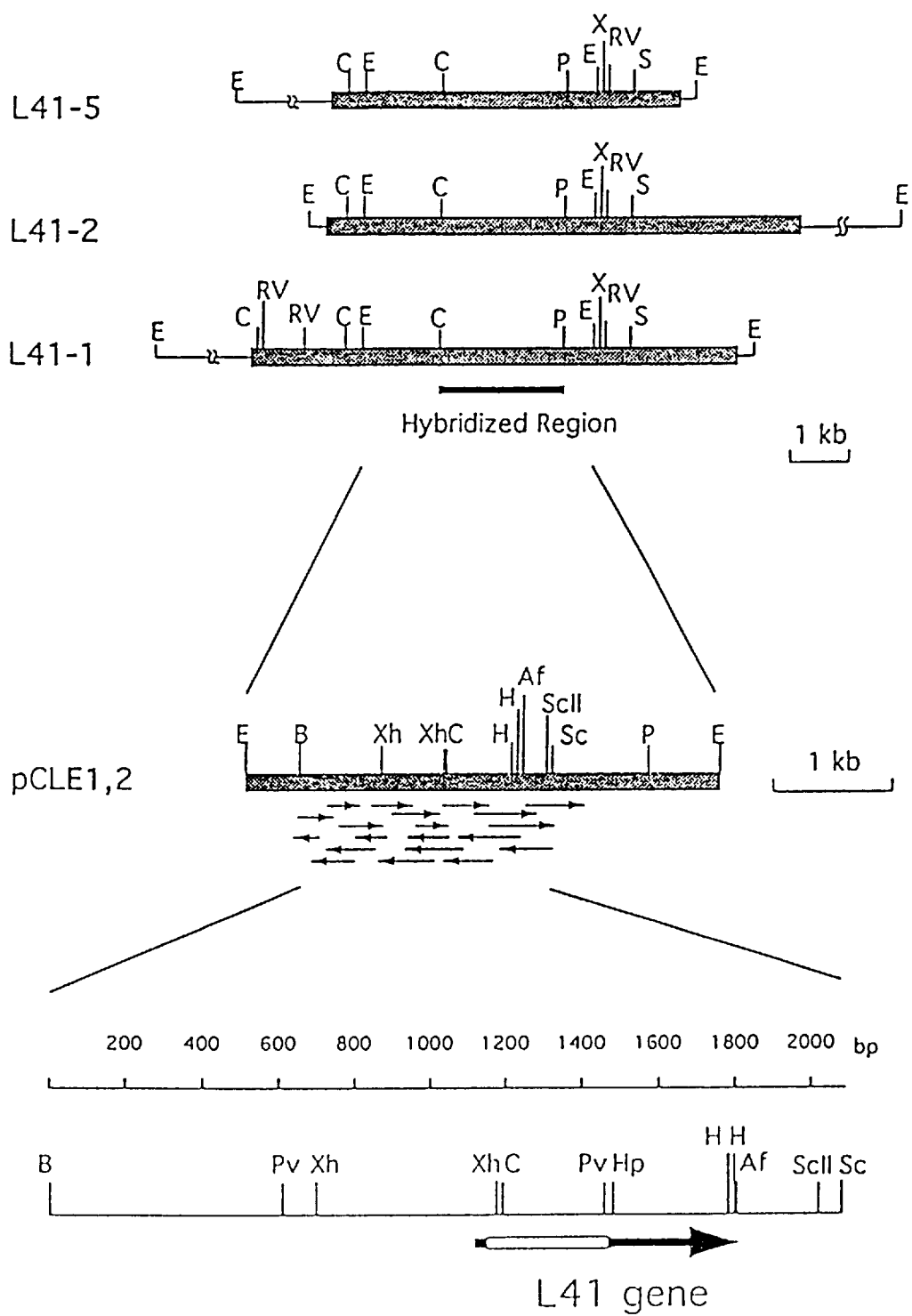
F I G. 12

```
   1 GGATCCAATC GTTGAAAGTG ATCAAGCTGA TTACAAAAGT AAGTATGAAA AGAGCCAATG
  61 TTGAGAGTCT CAGGAACCAC ATCGACTTCT TCGTGCCATC CTCCCACATT CTGAAGCCCA
 121 AGAACCCACA AATCATCAAA CACCAACACG ATGCGGACGC CAACCCGAGT TGTAACGCCA
 181 CAAAGTACGG GTACGACCCT GTTCCAGGAG GGCTCACGCC GCAATCAACA ACCAAAGTCG
 241 CCACGATCAA CGCCAGTATC AAGTAAAAGA AGAATAGCAT CTCCAGTCTT CCGATAGCTG
 301 TGTACTTCGA TCTGACGTTG TAGATGATGA TGATCATGAT CACGAGGGCA CCAATGTTGA
 361 CAAAGGCGTT ACCAATCTGG AATATCACGG TATTGGCAAC GTCTATCGGA CGGGCGTAGC
 421 ACTCAGGGAT GATCCCTTCG TTCAGGTGCG TGAACTGCTC GTTCGTCGTT GCCTTCACAA
 481 CCTGGCACAA CGGGAGCGGC GTGTTGTGGC ATAGCGAGTT GAAATCACCG AATGCCATTG
 541 TGTTTTATCG TTAGGGAGAC CTGTTTGAAG CTGACAGCGG GATGAAGATG AGGAAGGAGA
 601 GCACAACAGC TGAGCGGAAG TCTCTGTGAT GCTTGGTGGA CCGGGTGTAG GTGAATCTC
 661 CCTGGTGAGC GTACTTGCAA CGGTGCTCAG CGACTTCTTC TCGAGAGGAA ACGTAAACAA
 721 AGAGGTTTCA ATGTTGATGT TGATGTGTAT TTTTGTTACA AAAGCAGAAA TTGTAAACAA
 781 AAAGGTATAA TTAGGGCTCT GGTGTAATGA TGGGCACGTG ACGTTACCGT GCTGGTCGAT
 841 TTTAGGGCTA TTGGTTCGCG TCCCGCTGGT GTCCGGGTTA GCGTGTCAAT GTGGCGCCTC
 901 CCGATTATTA CATAAGAAAA CACCCACCCA CGCAACACCT GGTGTCTGGA TGTTGACGCT
 961 TTGTATGCGT GTGTGTGTTT TTCTTCCGT CTTGTTGGGC CACTCTGCGC GAGCGTTGGC
1021 GACTCACCGG TGAAATTTAT CGAAAACTTT CAGGCTCAGG CCCTTTTCAA CACTACCCTT
1081 TGAGATCACA TCAAGCAGTA ATCAAACACA ATGGGTATGT GGGAAACGAC GACGTGTGCG
1141 GTGTGTGAAT GCCATTAGTG GGATATGTGG TAGTCTCGAG CGTGGATATT ATCGATAGGG
1201 ATGGTGCTTG TTCTATACGT CTTGCTGGGA AGGAAGAAAG CGATGAAGTA TGTGGGAAGA
1261 AGGGGTGGTT TAAGAGAGGA AGTAGACATG TAACAAGTGT GTTCAGAGAA CAAGGACGGA
1321 AAATATCACCT ATATGACGTA CACATCACGA ACTGCTCCTG GAGGAAGCGA CAAGATGAAT
1381 ATCAACAGGC ATCATCATAT CTCTACAATG GCTCGTTCCC AAAGCACACG CACAAACAAA
1441 TCCGAGACTT TTGTACTAAC AGCTGTATCT CTGACAAATA GTTAACGTTC CAAAGACCAG
1501 AAGAACCTAC TGTAAGGGTA AGGAGTGCAG AAAGCACACT CAACACAAGG TTACCCAGTA
1561 CAAGGCTGGT AAGGCTTCCC TCTTTGCCCA GGGTAAGCGT CGTTATGACC GTAAGCAATC
1621 CGGTTACGGT GGTCAAACCA AGCCAGTTTT CCACAAAAAG GCTAAAACCA CCAAGAAGGT
1681 TGTTTTGCGT TTGGAGTGTG TTGTCTGCAA GACCAAGGCC CAATTGGCTT GAAGCGTTG
1741 TAAGCACTTC GAGTTGGGTG GTGACAAGAA GCAAAAGGGT CAAGCTTTGC AATTCTAAGC
1801 TTAAGACAAT TGTTGAAAGT TTTATTATTA TCACTACACT GTGTTTTTGA TGTCATCTAA
1861 TGTAAAAGCG TTTATATTAC CACTTGGTTC GGTATCCTGT AGAAGAATAC GGCCTGTAGC
1921 GTAGCATTCC CACAGGAGGA TCACAGCAAC ATAGACCAAA CAATGTCACG CACGGGGATC
1981 GAACGCGGAA CCAAACCTCT CCCTCCTCCC CCTTTCACCG CGGTTATTTT GTTATGGGCA
2041 CACACAGGGG AAGGAAAAAA ATGCACACAC GCACAAAAGC GAGCTC
```

FIG. 13

```
        10         20         30         40         50
         •          •          •          •          •
ATG G GTATGT GGGAAACGAC GACGTGTCCG GTGTGTGAAT GCCATTAGTG
Met Val>
        60         70         80         90        100        110
         •          •          •          •          •          •
GGATATGTGG TAGTCTCGAG CGTGGATATT ATCGATAGGG ATGGTGCTTG TTCTATACGT
       120        130        140        150        160        170
         •          •          •          •          •          •
CTTGCTGGGA AGGAAGAAAG CGATGAAGTA TGTGGGAAGA AGGGGTGGTT TAAGAGAGGA
       180        190        200        210        220        230
         •          •          •          •          •          •
AGTAGACATG TAACAAGTGT GTTCAGAGAA CAAGGACGGA AATATCACCT ATATGACGTA
       240        250        260        270        280        290
         •          •          •          •          •          •
CACATCACGA ACTGCTCCTG GAGGAAGCGA CAAGATGAAT ATCAACAGGC ATCATCATAT
       300        310        320        330        340        350
         •          •          •          •          •          •
CTCTACAATG GCTCGTTCCC AAAGCACACG CACAAACAAA TCCGAGACTT TTGTACTAAC
       360        370        380        390        400
         •          •          •          •          •
AGCTGTATCT CTGACAAATA G TT AAC GTT CCA AAG ACC AGA AGA ACC TAC TGT
                          Asn Val Pro Lys Thr Ser Ser Thr Tyr Cys
       410        420        430        440        450
         •          •          •          •          •
AAG GGT AAG GAG TGC AGA AAG CAC ACT CAA CAC AAG GTT ACC CAG TAC
Lys Gly Lys Glu Cys Arg Lys His Thr Gln His Lys Val Thr Gln Tyr
       460        470        480        490
         •          •          •          •
AAG GCT GGT AAG GCT TCC CTC TTT GCC CAG GGT AAG CGT CGT TAT GAC
Lys Ala Gly Lys Ala Ser Leu Phe Ala Gln Gly Lys Arg Arg Tyr Asp
500        510        520        530        540
  •          •          •          •          •
CGT AAG CAA TCC GGT TAC GGT GGT CAA ACC AAG CCA GTT TTC CAC AAA
Arg Lys Gln Ser Gly Tyr Gly Gly Gln Thr Lys Pro Val Phe His Lys
550        560        570        580        590
  •          •          •          •          •
AAG GCT AAA ACC ACC AAG AAG GTT GTT TTC CGT TTG GAG TGT GTT GTC
Lys Ala Lys Thr Thr Lys Lys Val Val Leu Arg Leu Glu Cys Val Val
600        610        620        630        640
  •          •          •          •          •
TGC AAG ACC AAG GCC CAA TTG GCT TTG AAG CGT TGT AAG CAC TTC GAG
Cys Lys Thr Lys Ala Gln Leu Ala Leu Lys Arg Cys Lys His Phe Glu
       650        660        670        680
         •          •          •          •
TTG GGT GGT GAC AAG AAG CAA AAG GGT CAA GCT TTG CAA TTC TAA
Leu Gly Gly Asp Lys Lys Gln Lys Gly Gln Ala Leu Gln Phe ***
```

FIG. 14

(1)
(2)
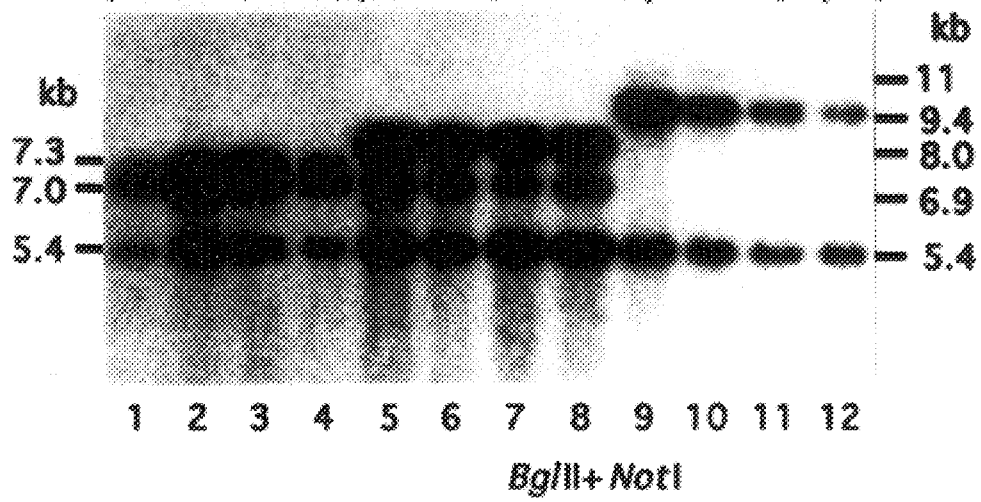
FIG. 21

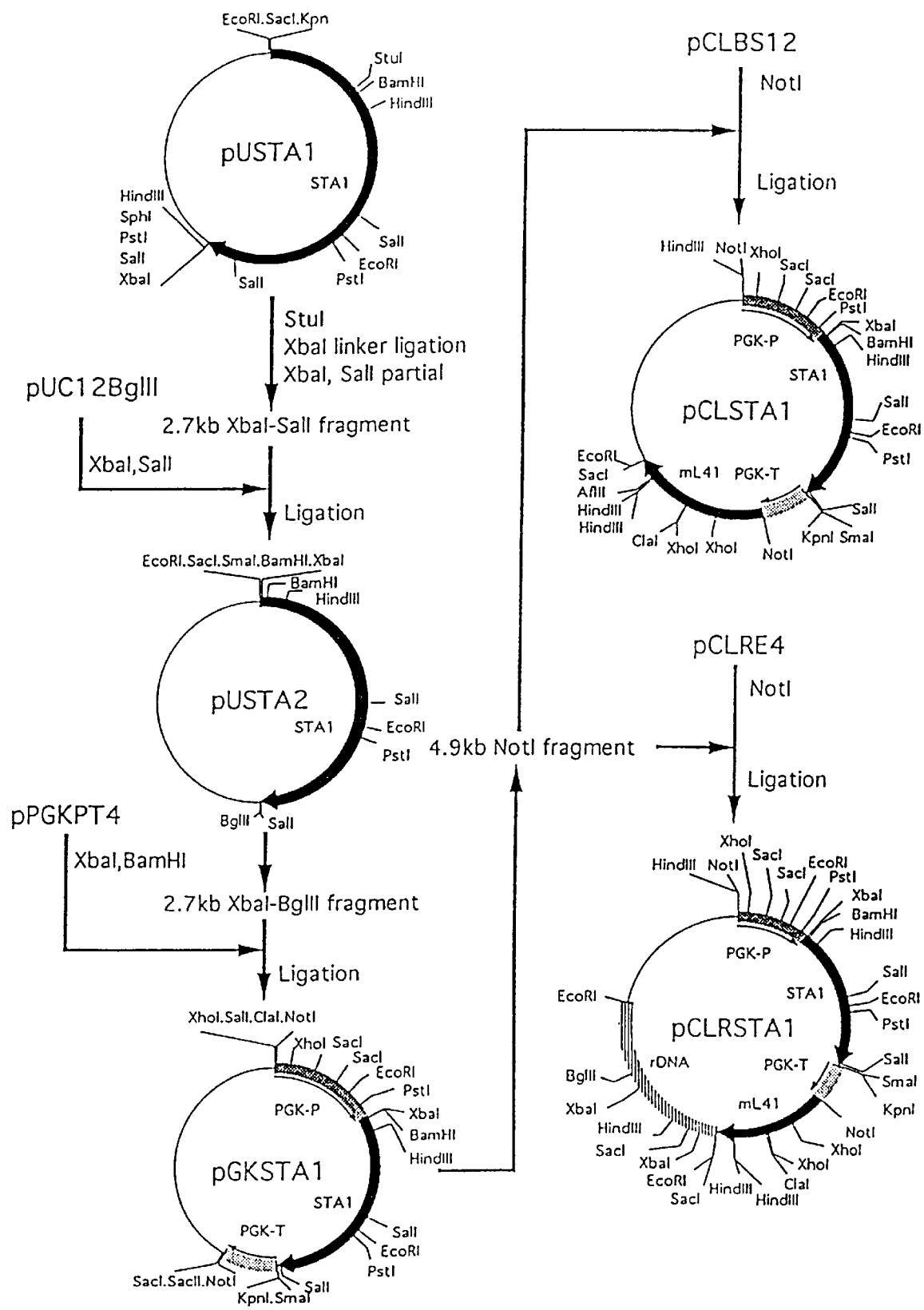
F I G. 23

```
  1 AAGCTTACAG CGAGCACTCA AATCTGCCCT CCGAGCCCTC CGGCCCTCTC TTCAACAAAC
 61 TCGCGCTGCA CTTCGTCGTC AGTGGTGCCA ATCACCCAAC GTGGAGGTAT CAAGAGGTGC
121 TCCAGCCCAC AAAGCGACAT CAAAGACAAC AACCCTGCCG GCCTACGTCC TACACACCCT
181 GGTGATCGCA GACATTGTAC AAGGTGCCAC GCAATAACCT ACAGGCACCG CACATGACGA
241 TGGCCTTGGT TGTGCAACCA GTGACTTCCA CGGTCCACGC AGCAACATGA ACCACACCAC
301 CCAGAATCGA TGCGCGCAAC AACAGTTGTT CCGGTTCACT CAGCCCCACA GCGAGTCGCT
361 GGCAGAACAC GAGCCTGAGG GCGGAAAGAG GGTAGAGGAA AGCGCAAGGA CAGGGGACAA
421 CCTGGCCCAA TTGATGTCAT ATAAACCCTC TCGATCAATT GAGCACACTC ATCCGCCAAT
481 TGACCCTGT TCGCAGCTCC ACGCCCATG TTCCTCGTCC CTGGTGTAGC TTCTCCCCTA
541 AATTCCAGCG CTTGGTTCCG CCCTCCCTGT CTCCCGGGTT TAACGAACGT GTGTACCATC
601 TGATGGTAAT CCGCTCCCGT CCGCGCAACA CAACTCACAA GCAGATCACA CCTGTACACG
661 CCGCTGCTGA TGCGCCCAAT TTAATTTTTT TTCTCTCAAT GTAGGGGAGA AGCCTTGGGA
721 GCTCCCGACT CCCAGTTGGG CACAGCTGCC ACCTCATGAC TTTTCCTGTG TGTGCCTGTC
781 TGACGTTACG TGTGATGTAG TGGCCCCCGT TCGGTGTGTT TTCGCCTGTT GCGCTGTGCC
841 CCCCTTAAAA GTATAAAAGG AAGTGCAATT GCTGTTTGTG TTGATTGTTG ATCCTTGTTT
901 CCTCTGTTTC CTCCTCATCA CACAAGAAAG GTTTCTTCTT TCCAACAGAT ACAAACACA
961 CTTACAAACA ACATA
```

FIG. 30

```
  1 ATTGTATGAC TTTTATTTAT GGGATTACGT TATAAATTAT GATCCTCATG GATTATCTTA
 61 TTAAGTCTCC ATCTTGTAGC TTGTAATATG ATGAACACTC GTGAGTTTTC CAGGTAATTC
121 ACCGTGCCTC GTCCATGCAC TTTTATCAGC CTCGACGTCA TACATTGCAT GGTGAGTAAC
181 TGGAAAACGG CTTTTTACGT TCTGTTGTAT ATGGCTAAAC GCTTCTATGG CACGGCGCTA
241 TTAACCTGTC TGACATTTCA ACCTGGTGTT GATGGCTTAA ACGATAATAC GGTGAGATAT
301 ATAGCTAACA GAATGGGGGT GACGCACTGA TTCCACTGTA TATATAGGCG ATATGTGTTG
361 TTGGATGGAC GTTTCTTTGT CTCCTGATCC ACAATAGTAG CTCAGCTCCG TGCCAACTGG
421 TTCGCTGGTA CGATAGTGAG GGATGAATGA AACCTTTTCG TTTTCTTCTG CGCTTCCACG
481 GAACTGTGTA GATTTCTCTC GTGAATAGCG AGTTAAGCCA CGAGTGGGGT CTGCAATTGA
541 AGGTGTGATA CCAGAGTCAA AAGTTTGGAT GTGATGGAAA CTTCAAAGGC TTCTCGGTGG
601 TATATCAAAC GATTCACAGA GGTAGAAGCG GATCTTGAAG GCCAGAATAT GCATTAAAAC
661 CAGCGTATAT CAGTTTTGCT TTCCCAGAGA GGACTTTTGC ATTATTCTTC AGCTTTATCC
721 CTGGATTTTG GGAGATGAAA CATTGACAAA GCTGGTTCGT GATCCTAAAT ACTTGCCTAC
781 TGACTCCTGA GGTATTACAC GT
```

FIG. 31

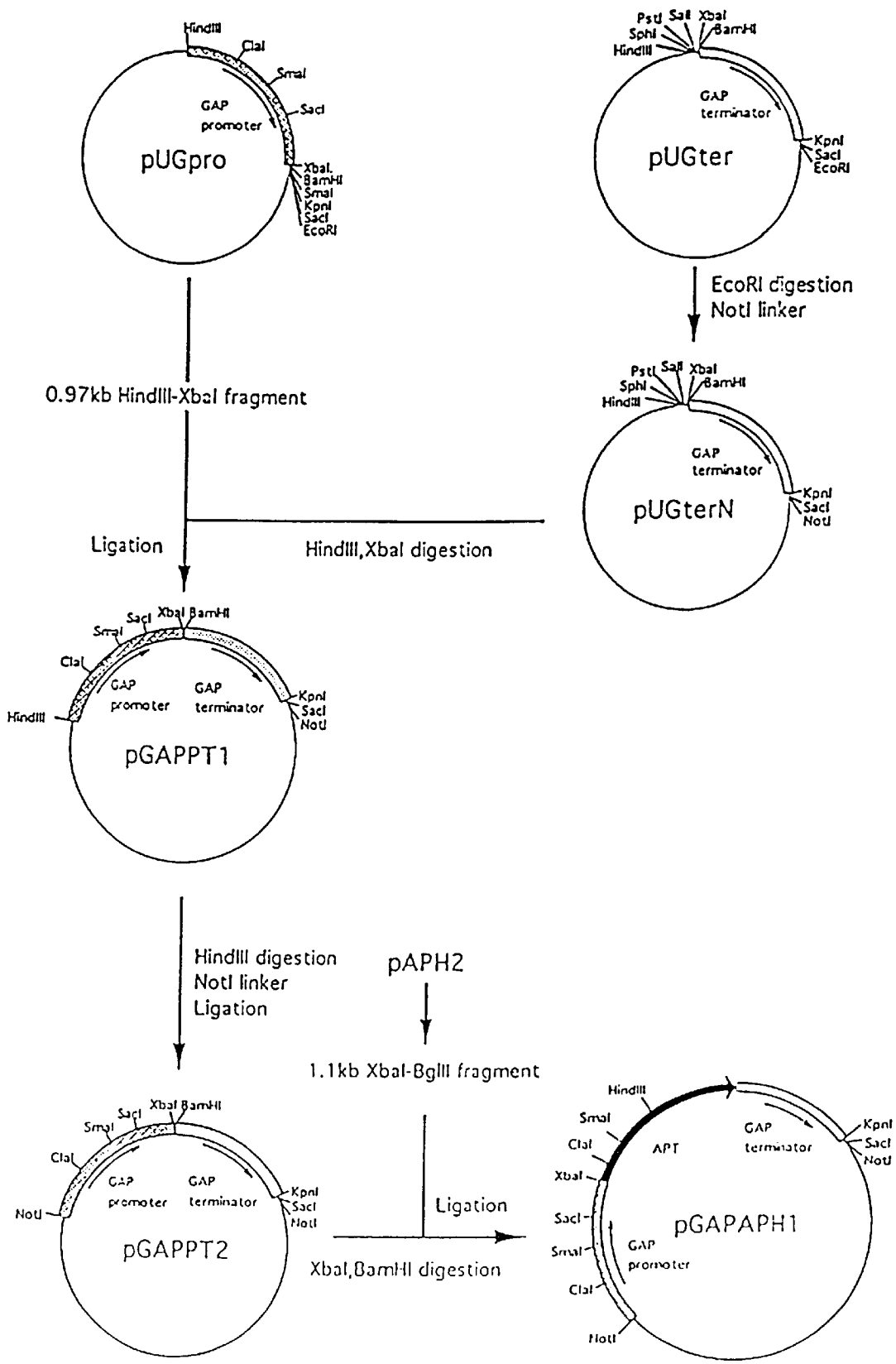
F I G. 32

```
  1 TCTAGAGCTG TCGACGCGGC CGCGGAATTA ACCCTCACTA AAGGGAACGA ATTCGGATCG
 61 GTGTTTTGGG CAGTGGGACC AAATCGATGC CATGTTGTT  TTTTTGTATT TTCGCAACTT
121 TTTCCCCATT CGGTCATACC GAAGGCGGTT CAAGCCTGCA AGAGACAACA ACTATGGCTG
181 CTGTTCTTGG AATGAAAATA AACGCATTTG AAGTTTTGC  AGCCAAAACA GGATGCGTTT
241 TCGCCATTTC GGTGCGGCAT TTCCGGTTTC AGATTTTCGC GAAATTTGTT TTTCCCATCA
301 AATCTGCAAA TTTCGGAAAC GGGCCGCGCT GATTGGCTGC GTCCTGAAGC GGCAATTTTT
361 CTCCCTCTCG TTTGTTGATA CAACCAAGAA TTTCTTTTCG TGCTCTGCGC CAGCGCTATC
421 CAAATGTTTA TAAATCTTGA TGTGATTTCC CGTTTTCTGT CCTTGCTCAT TCTGTCTCTC
481 TGTTGAACCA TTGTTGTTTT ACGAACTCAA GGTCCAATTG AACAGTATG  TGCACTGCCA
541 ATGGAGCATT GAAAGGGTTA TTCGATGTCG TCACCACGTG ATACTAACCA TTGATATAG
```

FIG. 34

```
   1 GCCGCTAATA CCCCTTAGGT TTTCGTTTCA TACATAGAGT GGTTGTTGTT TAACATTTTA
  61 TCGTGATTAA TTTTTAATCG AGTAATATAT TATTGGAAAA GTTTTTAGAC TTTGAAGCGT
 121 AGTATCGGTG GCTTTGCGGA GCTTAGCGCT GTGTCCTTTC TCCGTTGTTT ATGGAGTGTT
 181 GATGTTTTGT GATTTACAGC GATGTCCGGG TTTTTGTGTA CACGCTGCCC TTGAACCAAA
 241 AAAAAAGCTG CTGGGAATCG ATCGAGGGAA AAAACATCAC CAAAAAAAAA ACAAACAGCA
 301 GAAAGTAAAC AAACAACATT ACAAACAACA ACATCACACA GCGGCACGCT TTAAACCAGG
 361 GCGGTAGTGA CGTGACTTGC TTGTTTTCGA TCAGCGAGTG CGGTGTTATC GATATCTTCG
 421 AATCTGCTTA TAGTTCAAGA ACGCCTGGAT CCCAAGCGTA GTGAAGTGTT CTCTTTGTT
 481 TACTTTCTGT TTGTATATT AGTTCGGAAC CCATTAGAAA AGGTTCATCT CTGAGATAAA
 541 GAGCAAAGAC GCACGAGACA ATCAATCATT TGAGATGGGA TCAGTATCAG CGGAGAGTGC
 601 TGATAAGATT GAGGAGAACA GAGCAACTGG GGCTTGTTTG ACATTCTCT CACCACCAAA
 661 GCCTTCGTCA ACGTCCACAC CACCTACAGC GACTGCTGGT GCCATTGGCG GGTCTGGTAA
 721 TGAAACCAGT GACAGCTTCA ATCCTTTTGA GAAGGACTCA CTGGATGAAT CTGCTTCGGT
 781 GTTATCCACA AAGCAACTGC TTGCTGAGGG ACAGGGATCA AATGCCCTGC CATCTGAACT
 841 CGTTGATATC AACTTGGCGA TTAGCGCTCT TAACTTGGAC TTTGACGGTC AAAAACGTGG
 901 ACAAACTACA GCCACTACAG AGCCAGTAGG TGTTTTGAAA GATGGTGCCG AACCTAGTGC
 961 TACAGGATCA GACGACCACC CGCCACCAGC TCTGTATCCA CCAGGTATGA TCCCACAGCA
1021 CATGCCATTT TTCCCGCTAA ACGAATTTGG ACAGCAATG CATGCACCAT TCCCTGGAGA
1081 CCATCCACAT AGTCCAATCC CGTGGGATTC CAAACCTGGA CAGACTCCTT TTGGTTTAAT
1141 GGGATCTCAT GGCCCAAATA TGGATGGGTT ACGCTCACAA ATGGTACC
```

FIG. 35

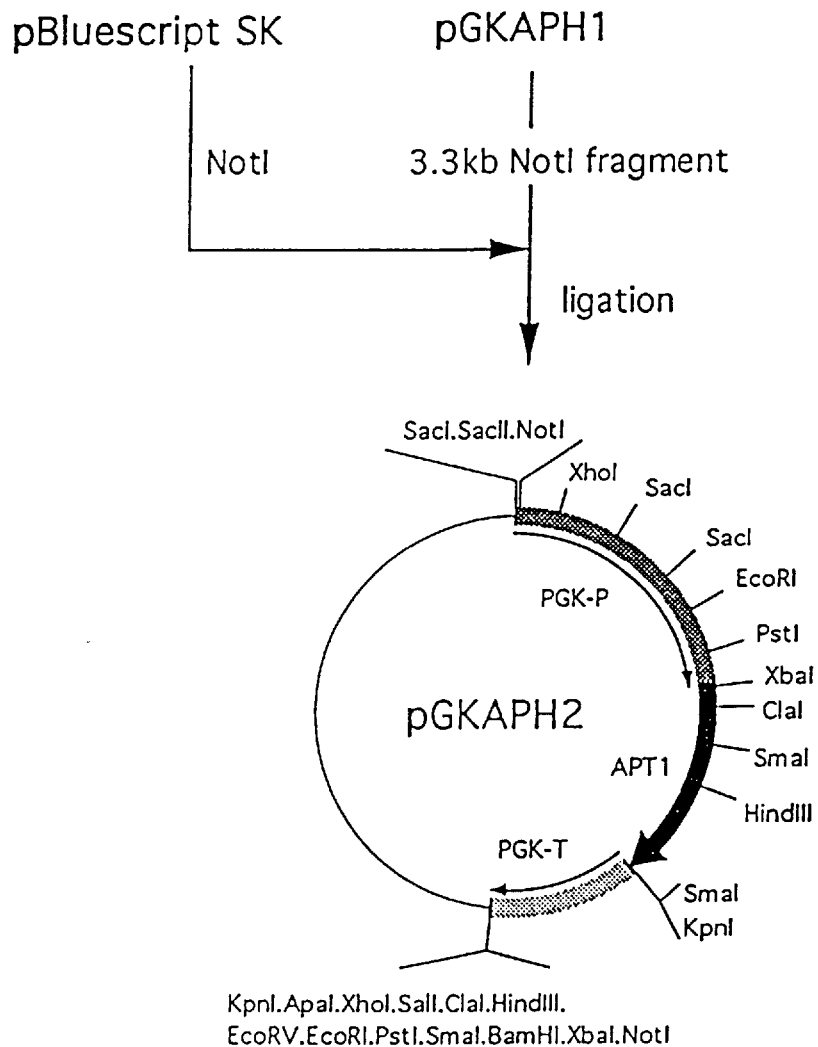
F I G. 37

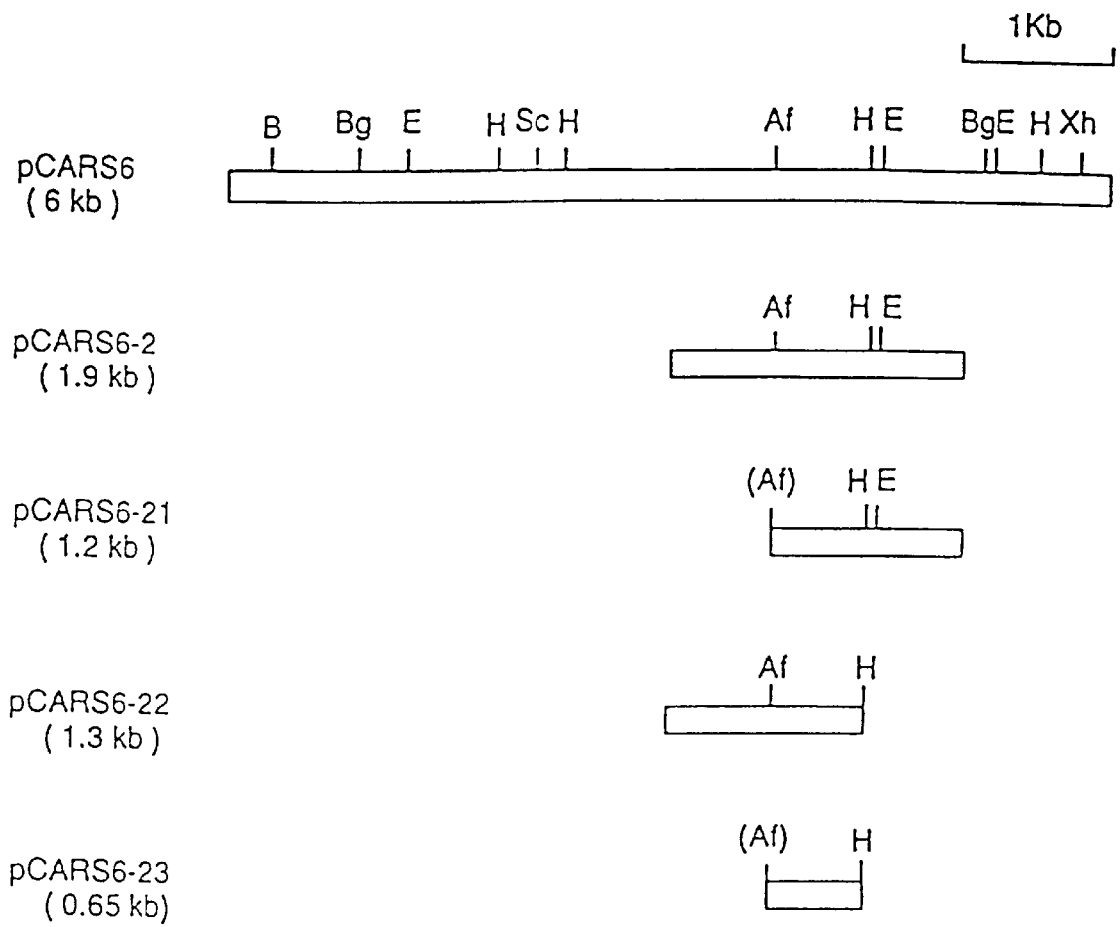
F I G. 39

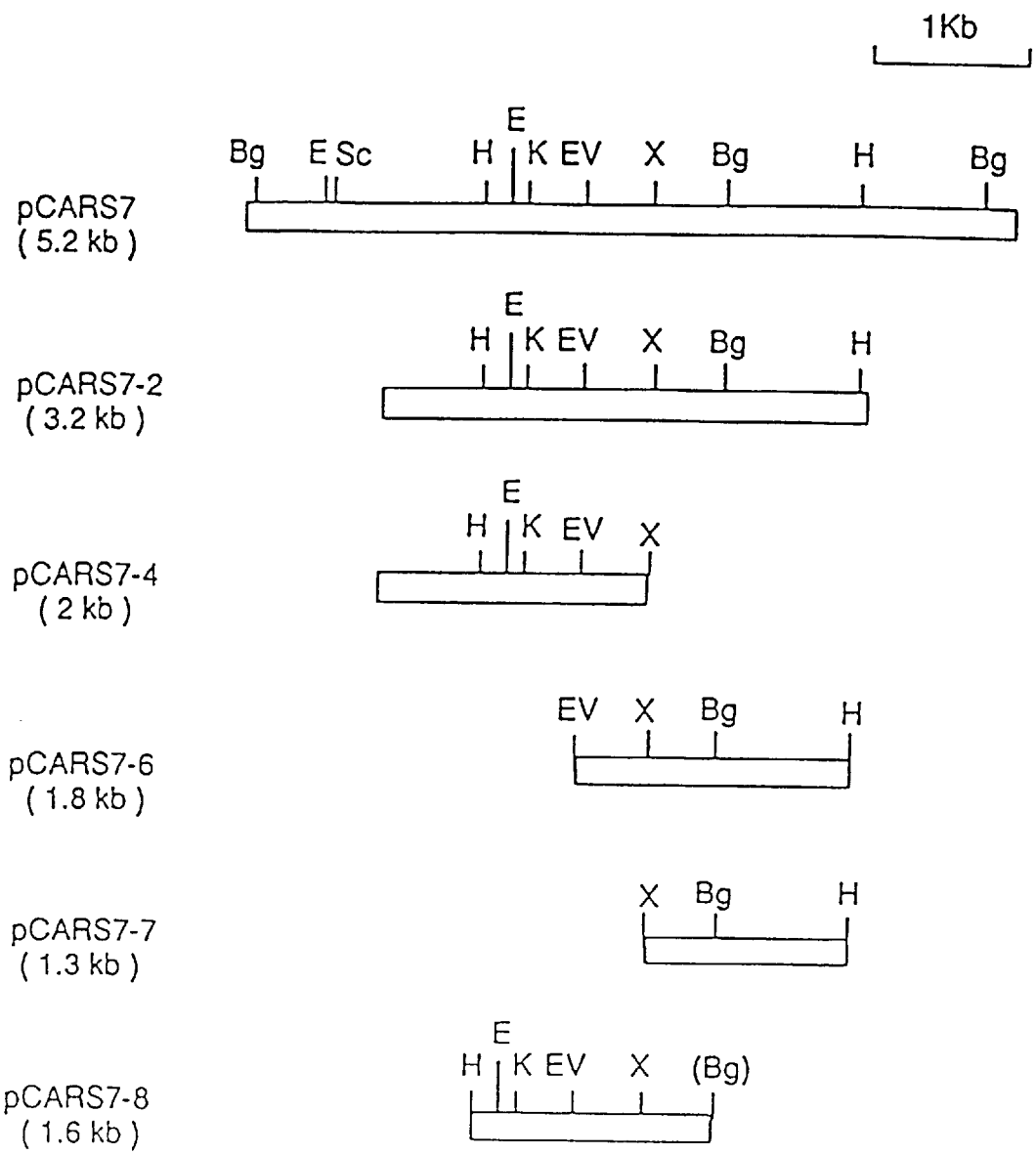
F I G. 40

```
       Sau3AI
     1 GATCATGTTT CGTACAAAAC ACCGCCACTC CGTTATGAGA AAGTCATAGT TATATTTCGG
       CTAGTACAAA GCATGTTTTG TGGCGGTGAG GCAATACTCT TTCAGTATCA ATATAAAGCC

61 GGAAACTTAT GTTGCTTGCA AGGAATAATA GACAGACAAA TGTTTTACGA AACTGAAGGA
       CCTTTGAATA CAACGAACGT TCCTTATTAT CTGTCTGTTT ACAAAATGCT TTGACTTCCT

121 TTAATACAAT TGATGCAAAA AAACAAAAAA AAAAAAAAAA AAAAAAAAAA AAAAAAAACA
       AATTATGTTA ACTACGTTTT TTTGTTTTTT TTTTTTTTTT TTTTTTTTTT TTTTTTTTGT

181 AAAACACAAA AACACAAAGA AAAAAAACAC AAAGAAAAAA AACACAGAAC ATCCAAAACA
       TTTTGTGTTT TTGTGTTTCT TTTTTTTGTG TTTCTTTTTT TTGTGTCTTG TAGGTTTTGT

241 AAACAACAAT ATATATATAT TTGCTAATAC CATCACCCTC CCTCATACAA AAAAAAAAG
       TTTGTTGTTA TATATATATA AACGATTATG GTAGTGGGAG GGAGTATGTT TTTTTTTTC

301 AAAATGGAAG GAGCACGTAT ATCTTTTCTA TGATCTTTGG ATATGGAATA GATAAGCAAC
       TTTTACCTTC CTCGTGCATA TAGAAAAGAT ACTAGAAACC TATACCTTAT CTATTCGTTG

361 CCCTCTAGTG AAGTACACAT CAAGATACTT GGGGAGCAAA CTGAGAGCAC ATGATATACA
       GGGAGATCAC TTCATGTGTA GTTCTATGAA CCCCTCGTTT GACTCTCGTG TACTATATGT

421 CGAAAGCCAC CATATATCAT ATATAAAAAT ATGAAACATG AAAAGTTATT CATCTGTTGG
       GCTTTCGGTG GTATATAGTA TATATTTTA TACTTTGTAC TTTTCAATAA GTAGACAACC

481 ATTCACTTTT ATATGTTTTC ATGCATTGTC TACTCTATGC CTCTGTCTTT TCTCTGTTCC
       TAAGTGAAAA TATACAAAAG TACGTAACAG ATGAGATACG GAGACAGAAA AGAGACAAGG

541 TTTACACTCC TCTATTATCA AATTGAGTGT TTCATTTATC AAAGAAGTTT GAGCTGGATC
       AAATGTGAGG AGATAATAGT TTAACTCACA AAGTAAATAG TTTCTTCAAA CTCGACCTAG

601 AGAACTTTAG ATATTCATTC CTGTTTTCGA TATATCTATA CGATGTTCTA ATATCCACTC
       TCTTGAAATC TATAAGTAAG GACAAAGCT ATATAGATAT GCTACAAGAT TATAGGTGAG
                                                     AflII
   661 TCACTACCAT TGTTAAAAAA AGTTAAAATT ATAGCTGTGT GCCTTAAGGG AATAAAGGAA
       AGTGATGGTA ACAATTTTTT TCAATTTTAA TATCGACACA CGGAATTCCC TTATTTCCTT

721 ATGGATCTTT TGAATGTTAA AAAACGAGAT ACTCTTTTGT AAACCAGAAA ACGATTTTCA
       TACCTAGAAA ACTTACAATT TTTTGCTCTA TGAGAAAACA TTTGGTCTTT TGCTAAAAGT

781 AAACACAAAT TGGTGAATGT CACCAAGCAA AAATTGTATC CTAAAAAAAA TAAATTTATG
       TTTGTGTTTA ACCACTTACA GTGGTTCGTT TTTAACATAG GATTTTTTT ATTTAAATAC

841 AACTAAATTA TCTCTGAACA GACATTTAGT CAACCTTTTC TCCTTGCTCC TCGGTCAAAG
       TTGATTTAAT AGAGACTTGT CTGTAAATCA GTTGGAAAAG AGGAACGAGG AGCCAGTTTC

901 GTTTTTCGTA TAGATATATA TACGGGTTGC TTTTTTGTTT CCACTCGTCT AATCGAGTTT
       CAAAAAGCAT ATCTATATAT ATGCCCAACG AAAAAACAAA GGTGAGCAGA TTAGCTCAAA
       EcoRV
   961 CGATATCAAT GGAGATTTAT TCTTTGGCTT TGATTCCATA ATAATCCATA TCCTAATAAA
       GCTATAGTTA CCTCTAAATA AGAAACCGAA ACTAAGGTAT TATTAGGTAT AGGATTATTT

1021 ACACTTTGAA GCGAATTGAA ACCCCAATAT CTTTCTGGCC ATTAAAACAT TTATAAAGTA
       TGTGAAACTT CGCTTAACTT TGGGGTTATA GAAAGACCGG TAATTTTGTA AATATTTCAT

1081 CTGGATGTTT AAAGAGCTTT GAGAATTGCC TAGCTTCAAA ATATATTTGT CTCCAATTAT
       GACCTACAAA TTTCTCGAAA CTCTTAACGG ATCGAAGTTT TATATAAACA GAGGTTAATA

1141 GATTTTGTAT TTTCCTTTCT TTGTTTTCTG TAGTTATTTA AAATAAGTTC ACTACGTTGT
       CTAAAACATA AAAGGAAAGA AACAAAGAC ATCAATAAAT TTATTCAAG TGATGCAACA

1201 TTTTTGAGGA ACCGTTACTC TATTTACTCA AATTTATTAT CAAAATGTTT TTTTTTCGTT
       AAAAACTCCT TGGCAATGAG ATAAATGAGT TTAAATAATA GTTTTACAAA AAAAAAGCAA

1261 TGATTTATTC AAATGCTGTC GATATGTCCC AGAAATATCA TACAATTCAA ATTTCTAAAG
       ACTAAATAAG TTTACGACAG CTATACAGGG TCTTTATAGT ATGTTAAGTT TAAAGATTTC
```

F I G. 41

```
                     HindIII
1321 CCAGCGTTTA TTATAAAGCT TTGAGTTCTT TCGACTTAAT TACATGTATG TAGCTCAAAC
     GGTCGCAAAT AATATTTCGA AACTCAAGAA AGCTGAATTA ATGTACATAC ATCGAGTTTG
                                                       EcoRI
1381 CAAAGTTACT CTATAATTAT AAAAAGACTA TGAACCAATT CAAGAATTCC CCATTTCCAG
     GTTTCAATGA GATATTAATA TTTTTCTGAT ACTTGGTTAA GTTCTTAAGG GGTAAAGGTC 1441 CAAATTTAGT ATAGCTCAAA TTCACACTGT CATATGCAAA AACCTAAATA AGCAGATCAT
     GTTTAAATCA TATCGAGTTT AAGTGTGACA GTATACGTTT TTGGATTTAT TCGTCTAGTA 1501 TGTAAAGAGC CGGCAGTTGT ATATTCCAGT GGGGCTGAAC TTGTGGTTAG GATTCACAGA
     ACATTTCTCG GCCGTCAACA TATAAGGTCA CCCCGACTTG AACACCAATC CTAAGTGTCT 1561 CATCTTGTTG TCGGATTTCT ATTGATAGAA GCTGTGCCAT TGAAAATGGA AATATAAAAT
     GTAGAACAAC AGCCTAAAGA TAACTATCTT CGACACGGTA ACTTTACCT TTATATTTTA 1621 GGTATTGGGT TGATCATATA TGAATTTCTT ATTACTCATA ATAATAGGAG AAATCATCGA
     CCATAACCCA ACTAGTATAT ACTTAAAGAA TAATGAGTAT TATTATCCTC TTTAGTAGCT 1681 ACATGGAACA TAGATGCTAA TTAAGGTACG TACAGCATCC TGTTCAATAT TTCAACTTTT
     TGTACCTTGT ATCTACGATT AATTCCATGC ATGTCGTAGG ACAAGTTATA AAGTTGAAAA 1741 TAAGTATTAA ATTAGTGAAG AAATGTATTA TGAACCATTG TTCAATAATT CTAATGTGTT
     ATTCATAATT TAATCACTTC TTTACATAAT ACTTGGTAAC AAGTTATTAA GATTACACAA 1801 TTTTGTGGTT TTTTTTTTGG CTTTTGGGAC ATTGTAATTT TTACTCATTT ATTCGATGTC
     AAAACACCAA AAAAAAAACC GAAAACCCTG TAACATTAAA AATGAGTAAA TAAGCTACAG
                                                            Sau3AI
1861 TCTTCAGGTT TTTGTGTTTT TTTTTTTTGT GTTTAATCT TCGCGGAATT GAGATAAGAT
     AGAAGTCCAA AAACACAAAA AAAAAAAACA CAAATTTAGA AGCGCCTTAA CTCTATTCTA

```
                HindIII
  1  AAGCTTATAG AATTTGAAGA TATAAAACA CAACAAAGCT ATGAAAGCAA TGAGGGGACG
  1  TTCGAATATC TTAAACTTCT ATATTTTGT GTTGTTTCGA TACTTTCGTT ACTCCCCTGC 61  ATTTGATGAA CAGAAGGAGC TATTCCCATT AATTTAATAT CTACCAATAG ATATGTCAGT
 61  TAAACTACTT GTCTTCCTCG ATAAGGGTAA TTAAATTATA GATGGTTATC TATACAGTCA 121  CAAACATGTC AGAAGTCATA CTCACTAATT ATATGAGCGG GTGCGTTAGA TATTTATATG
121  GTTTGTACAG TCTTCAGTAT GAGTGATTAA TATACTCGCC CACGCAATCT ATAAATATAC 181  AGTTTGCATC TTTCTACATG GGGCTTTCAA GTAACTGGAA GTAATACAAC TTTTGTTTAA
181  TCAAACGTAG AAAGATGTAC CCCGAAAGTT CATTGACCTT CATTATGTTG AAAACAAATT 241  GTTGATAAAA ACAAAAAACA AAAAAACAAA AAACAAAAAA ACAAAATAA AAAAAAAAAA
241  CAACTATTTT TGTATTTTGT TTTTTTGTTT TTTGTTTTTT TGTTTTTATT TTTTTTTTT 301  AAACAAAAAA AAAAAACAC ACACGCACAC ACACACATAT ACAAACACAT ACAAAAAACT
301  TTTGTTTTTT TTTTTTTGTG TGTGCGTGTG TGTGTGTATA TGTTTGTGTA TGTTTTTTGA 361  TATCATAATT AAGATAAATG AAAGCTATCT AAAATTTCCA GACATTTTCT GAAAAAGTGG
361  ATAGTATTAA TTCTATTTAC TTTCGATAGA TTTTAAAGGT CTGTAAAAGA CTTTTTCACC 421  CTGCCAGCTT TATTGCTTTG CTTTAAATTT ATAAAGAAAA CTTCTTTGAA ATCGAATATG
421  GACGGTCGAA ATAACGAAAC GAAATTTAAA TATTTCTTTT GAAGAAACTT TAGCTTATAC 481  AAACAAGAGG AAACGGATGA AAGGATAAAA CACAAATACA GGAAAACATT ATTACAAATA
481  TTTGTTCTCC TTTGCCTACT TTCCTATTTT GTGTTTATGT CCTTTTGTAA TAATGTTTAT 541  AAGCACCTGT AAGAGATAAA TTTGTTACAT TTAAAGGATT CTACTTACAT ATACAGAGAA
541  TTCGTGGACA TTCTCTATTT AAACAATGTA AATTTCCTAA GATGAATGTA TATGTCTCTT 601  AGCAATTTCA TAGACATAGG GTCTACCGAA CAGTCTTGAT ATTTCAGACT AGTATTTTTG
601  TCGTTAAAGT ATCTGTATCC CAGATGGCTT GTCAGAACTA TAAAGTCTGA TCATAAAAAC 661  TTGTATTATG GGGCTTGGTC GGTATGTTAG TAAAAAGTTC ATTTTAAAAT TTTCCAAGAA
661  AACATAATAC CCCGAACCAG CCATACAATC ATTTTTCAAG TAAAATTTTA AAAGGTTCTT 721  GTGTTTTTAT TGCAGAAAAA TATCCGTGGT TCAAGAGATA ATGGGCTGTA AATTTGTTTT
721  CACAAAAATA ACGTCTTTTT ATAGGCACCA AGTTCTCTAT TACCCGACAT TTAAACAAAA BglII
781  GTACCAAAAA TATCTTAATT AATACAAAGA ATACCTTTTA TGAAGGTAGA TCAAGATCTT
781  CATGGTTTTT ATAGAATTAA TTATGTTTCT TATGGAAAAT ACTTCCATCT AGTTCTAGAA 841  AAATTTCATT ACTCAGAAAT GAATATACTT GAAACTTCCG AAATACTATG TTATGGGGAA
841  TTTAAAGTAA TGAGTCTTTA CTTATATGAA CTTTGAAGGC TTTATGATAC AATACCCCTT 901  CAAATAAGAG GAGCCATTTC ATATTTATTT TGGAAAGATC GTTTTCTATG CGCAGTTGTT
901  GTTTATTCTC CTCGGTAAAG TATAAATAAA ACCTTTCTAG CAAAAGATAC GCGTCAACAA 961  GGAATAGCGA TATTATCATG ACCTTATATT CAGTCAGAGA AAATAGGGTA CGAATTTGAA
961  CCTTATCGCT ATAATAGTAC TGGAATATAA GTCAGTCTCT TTTATCCCAT GCTTAAACTT 1021 AACAATGTTT CAGCTTCAAA GAGGACCTTT AAACGGTCAG GCAAAAGTTG AGGTGTCAGT
1021 TTGTTACAAA GTCGAAGTTT CTCCTGGAAA TTTGCCAGTC CGTTTTCAAC TCCACAGTCA 1081 GTGTATAAAA ATGTTCAATT CATTTTTGGT TGAAAGATGC TTTAAAAGGT TGGTGCAAAG
1081 CACATATTTT TACAAGTTAA GTAAAAACCA ACTTTCTACG AAATTTTCCA ACCACGTTTC 1141 AATCATATAT GTGTATTGGC TAGTTAAAAG TTGCTTTATT AAAAATATAT GCAAACTAAA
1141 TTAGTATATA CACATAACCG ATCAATTTTC AACGAAATAA TTATTATATA CGTTTGATTT 1201 TTGTCTATAC GATTGATAAG GTGAAACTTA GATAAACAAT GAAAAGGAA GGTGCTTTGA
1201 AACAGATATG CTAACTATTC CACTTTGAAT CTATTTGTTA CTTTTCCTT CCACGAAACT 1261 AAACCGACCA GCTTCAAATA AATATGTAAC TATTTTTATG GATGTGAAAA TTAAATGTTG
1261 TTTGGCTGGT CGAAGTTTAT TTATACATTG ATAAAAATAC CTACACTTTT AATTTACAAC
```

FIG. 43

```
                      XbaI
1321  TCGAATCTGC  TGTTTCTAGA  TTTGTAGATG  AAAATGTTGA  CGTGAGAGTT  TTCATTTGTT
1321  AGCTTAGACG  ACAAAGATCT  AAACATCTAC  TTTTACAACT  GCACTCTCAA  AAGTAAACAA

1381  TGTATTTTAT  ATTATGCTTT  GATTACTACT  CATAGCTTGG  GTTTAGCATG  GCCTGAGTAA
1381  ACATAAAATA  TAATACGAAA  CTAATGATGA  GTATCGAACC  CAAATCGTAC  CGGACTCATT

1441  GTAGGAAGAT  CCAATAAATT  GACTGTTGTC  GTTTTGAAAT  TAAATACTGA  AATGAATAAA
1441  CATCCTTCTA  GGTTATTTAA  CTGACAACAG  CAAAACTTTA  ATTTATGACT  TTACTTATTT

1501  AGTTTGACGA  GAAAAGACCT  GAAATATATA  AAATGTTTT  GTATTATTTA  AGTCGGTTAC
1501  TCAAACTGCT  CTTTTCTGGA  CTTTATATAT  TTTACAAAA  CATAATAAAT  TCAGCCAATG

1561  ATTCTCTCAC  TTTATTGTAA  CAACCATTAT  AGTGATGGGG  AAAAAATAAA  ACATAAGCCA
1561  TAAGAGAGTG  AAATAACATT  GTTGGTAATA  TCACTACCCC  TTTTTTATTT  TGTATTCGGT

1621  CATAAGGAGA  TATTGTTCTT  TATTGAAAGG  ATGGAATCAT  TTTCTGGAAA  TGTCAAAAAT
1621  GTATTCCTCT  ATAACAAGAA  ATAACTTTCC  TACCTTAGTA  AAAGACCTTT  ACAGTTTTA

1681  TAAATATTAC  TTGGTTTTTG  ATGAATTGTA  GAAGAAAAAG  TAAATGCTGC  TATTCTCTTT
1681  ATTTATAATG  AACCAAAAAC  TACTTAACAT  CTTCTTTTTC  ATTTACGACG  ATAAGAGAAA
                                                                        EcoRV
1741  CTTTACATTT  GCCATGTTTC  CTGATTCTGG  CTATGTCACT  TTAAGTTGTT  GAGATATC
1741  GAAATGTAAA  AGGTACAAAG  GACTAAGACC  GATACAGTGA  AATTCAACAA  CTCTATAG
```

FIG. 44

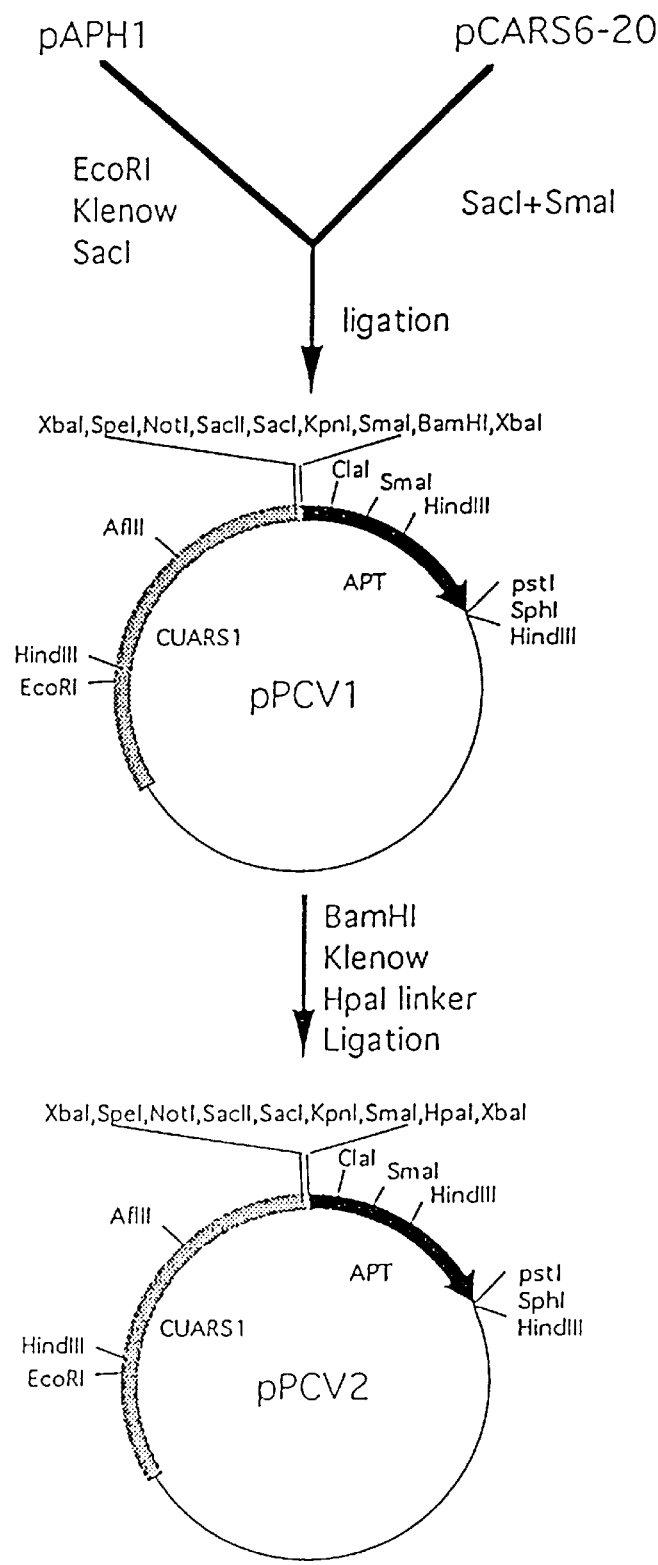
F I G. 47

```
   1 CCACATTTGT TGTACGAGAA GGGCCAACGA CAGCTCTCTT CGAGGAAGAC TTGGAGATAA
  61 GCCTTGCTTG ATTTGTAATC TTCAAGAGAG AGCTCTTTGT AGCTTGTCTT GTTGAGTGTC
 121 TGAGAAGCAT TTGTGCAATG AATATGGGAG AGATGAGATG AGTAGAGAGC AGCACAAGTG
 181 GAATCAAATC ACAATAACAA CTTTAGCCAC AGGGAGGTTA AAAGAGGAGA GAAGGAGTC
 241 CTTTCCAATT GTGGCTAGTG CAGAAGAGAA AATTTGCTTG CTACAATCGT GGTGTGTATG
 301 CAAACCCGTT GTAAAGGTGG TGTCTTTGTA TATGTAGGGT GTGTGGCTTC GTCTCGAGAA
 361 AGCACATAAG CTGTGGCGCA CTTTCTCGGG TAAGTGATTT AATTGCACGT GATCTCAATT
 421 TCTTTTTTTG AAGCCACTAA AGCTTACGTA AGCGACCACG GATCTGGTGT TGGGATGTTT
 481 TGGTTTTGGG AGGGGCAGGG GGTTACATG TTGGCTTTAT CGATTGCGGC GCTTTGTGTT
 541 TGGGGGTGTA TGCCCTAGCG ACCCTGTGGG CCACTGCCCA GGTGCCCAGG TGCGACCAGG
 601 AAAAAAATTT CTTCATCGCT AGAGCTTTCT TCAACCCCCT TTCTTTCCTA ATTCTTTTCA
 661 ACTAACAACA AATAAACACA GTAACAAGAT GTCATCTGAC CTTTCAGACG TTAGACTCTT
 721 TGTCAGACCA CTTCCATTCG ATGTTAACGA AGAGGACTTG AAGAGCTTCT TCTCCCCTAT
 781 TGGTGAAATC ACCGATTTCA TCGTTGCTAG AGGTTATGCC TTTGTTGAAT ACGCTAATGC
 841 AGATTTGGCA AGACAAGCCA TCGCTGAATT GCACCAAAAG CCGTTCGGTG ATGTTCCATT
 901 ATCCTTGGAG TACGCTAAGG CTCAAAAGCC AAGATTCAGA CTTCTTGTTT CTAACATGCC
 961 AGAAGGTGCT GAGTGGCAAG ATCTGAAAGA TTTTGCTCTC CAAAAGGGAT TCGAAGTTAC
1021 CTACGCCAAC GTTTTCCAAA GAGAGAACAA CGGT
```

FIG. 48

(1)
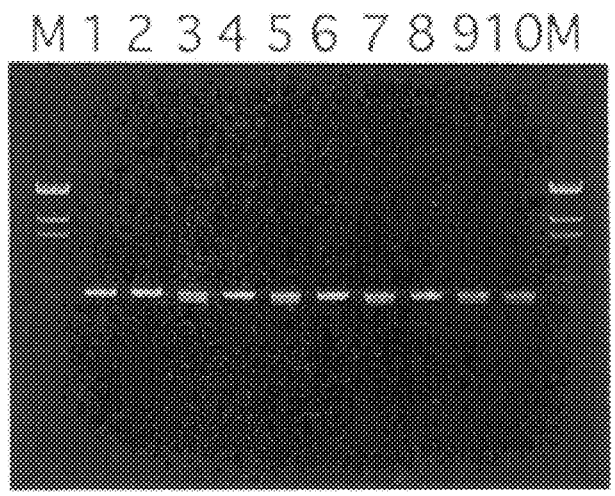
(2)
M; λ EcoT14I
FIG. 50

TRANSFORMATION SYSTEMS FOR THE YEAST *CANDIDA UTILIS* AND THE EXPRESSION OF HETEROLOGOUS GENES THEREWITH

BACKGROUND OF THE INVENTION

1. Field of the Invention

The present invention relates to reproducible transformation systems of *Candida utilis,* more particularly to the transformation of the yeast *Candida utilis* with recombinant DNA, and to the expression of heterologous genes in novel transformants obtained thereby. The present invention also relates to novel DNA sequences which may be used as selectable marker genes for transformation, and to novel DNA sequences which may be used as promoters or terminators for expressing heterologous genes. In addition, the present invention relates to methods for the efficient integration of heterologous genes into yeast chromosomes.

Furthermore, the present invention relates to DNA fragments having the properties of autonomous replication as well as enhancing transformation efficiency in *Candida utilis,* to methods for integrating DNA fragments having no selectable marker gene into chromosome, and to methods for obtaining DNA sequences having promoter activity.

2. Background Art

The development of gene manipulation technology has made it possible to produce useful proteins in a large amount with microorganisms. Prokaryotes such as *Escherichia coli* or *Bacillus subtilis* can be used easily as a host therefor, inter alia, *E. coli* being employed most frequently as a host. However, proteins produced in *E. coli* are often led to insoluble forms and cannot be glycosylated upon secretion, so that these proteins are not satisfactory for a variety of requisitions. In addition, pyrogenic toxic factors produced by *E. coli* must be removed, when proteins thus produced are intended to be used as medicaments.

As compared with the use of these prokaryotic systems, it is interesting to use eukaryotes such as yeast as a host for producing useful proteins. First of all, yeasts of the genus Saccharomyces or the yeast *Candida utilis* have been known to be of a high safety, since Saccharomyces has been long used for the production of fermentation products such as alcoholic products and the yeast *Candida utilis* has been used for the production of feeds. Moreover, yeast can be generally cultured at a cell density higher than bacteria as well as in a continuous mode. Yeast secretes proteins into a medium, and the protein secreted is modified by glycosylation. The production of proteins with yeast is thus of worth when such modification is important for biological activity of the protein.

Yeasts classified in the genus Saccharomyces have been investigated most extensively, and genetic information of them have been accumulated. The yeasts have been investigated as a host for producing a variety of substances. Further, transformation technology for some of yeasts in addition to Saccharomyces such as those in Pichia, Hansenula, Kluyveromyces, Candida genera has been developed, and these yeasts are now examined as a host for producing useful substances. Among them, the yeasts assigned to the genus Candida, inter alia have properties advantageous for practical use which are not found in the yeasts of the Saccharomyces genus such as a wide anabolic spectrum of the carbon source. The yeast of the genus Candida is thus expected to be used for the production of useful substances with recombinant DNA technology.

Among the yeasts of the genus Candida, *Candida utilis* has an excellent anabolic ability to pentoses such as xylose. In addition, *Candida utilis,* different from the yeast of the genus Saccharomyces, does not produce ethanol in culture under aerobic conditions and thus the growth is not inhibited thereby. Therefore, it is possible to produce cells efficiently by the continuous culture of *Candida utilis* under a high cell density. Thus, attention has been paid on *Candida utilis* as a protein source, and the industrial production of the yeast cell has once been conducted with use of a saccharified liquor of broad-leaved trees or a sulfite waste liquor containing a large amount of pentoses. The yeast, *Candida utilis,* as well as *Saccharomyces cerevisiae* and *Saccharomyces fragilis* has been authorized by U.S. FDA (Food and Drug Administration) as a yeast which can be used safely as a food additive. Indeed, *Candida utilis* has been used even now as feeds in many countries involving Germany, United States of America, Taiwan and Brazil, and thus it can be said that the safety of it has been confirmed.

In addition to the use of *Candida utilis* as a microbial protein, it has been used widely in industry as a microbial strain for fermenting pentoses or xylose or a microbial strain for producing ethyl acetate, L-glutamine, glutathione, invertase or the like.

However, any success has not been hitherto described or proved in the transformation of the useful yeast, *Candida utilis.* Failure in the transformation is believed due to the extreme difficulty of obtaining mutant strains to which a selectable marker such as an appropriate nutrient requirement is introduced by mutagenesis treatment with a conventional mutagen such as nitrosoguanidine or ethyl methanesulfonic acid. This difficulty may be because of the fact *Candida utilis* is a polyploid such as at least a diploid. This can be also deduced from the fact that while cloning of the genes such as ADE1 and LEU2 of *Candida utilis,* which have been frequently used in the other yeasts as a selectable marker for transformation, have been reported (Nishiya et al., Japanese Patent Laid-Open Publication No. 66089/1992; Kobayashi et al., Japanese Patent Publication No. 42673/1989), no *Candida utilis* host strain having mutation in the corresponding gene has been described. This means that it is almost impossible to apply to *Candida utilis* a conventional technique for direct selection of a transformant by introducing a complementary gene for the nutritional requirement of a host strain which technique has been used for the development of a transformation system in a variety of yeasts.

Moreover, *Candida utilis* has a high ploidy and no sporulation ability, so that its genetic properties have not been elucidated completely. Thus, the condition of transformation as well as the condition to be satisfied by a vector system remain unknown, so that it is expected extremely difficult to establish the host/vector system.

Ho et al. discloses an examination of preliminary transformation with a drug-resistant marker with respect to *Candida utilis* (Ho, N. W. Y. et al., Biotechnology and Bioengineering Symp., No. 14, 295–301, 1984). This report is incomplete, since the condition of the transformation experiment, or the exprimental data such as Southern blot analysis of the drug resistant transformant which is required for verification of the transformation are not disclosed.

Therefore, it is still desired to establish a reproducible transformation system with respect to *Candida utilis* and a production technology of useful substances with use of the system.

SUMMARY OF THE INVENTION

The present inventors have now obtained successfully transformants from the yeast *Candida utilis* reproducibly, and a variety of information on the expression of heterologous genes in the transformant. The present invention is based on these information.

An object of the present invention is thus to provide a reproducible transformation system of *Candida utilis*.

Another object of the present invention is to provide genes which are useful in the *Candida utilis* transformation system as selectable markers, as target sequences at which plasmid is integrated into chromosome, and as novel DNA sequences such as promoter and terminator required for the expression of heterologous genes.

A further object of the present invention is to provide vector systems which make possible to express heterologous genes in *Candida utilis*.

Another object of the present invention is to provide host/vector system into which the multiple copies of heterologous genes can be stably integrated.

A further object of the present invention is to provide process for expressing heterologous genes in *Candida utilis*.

In addition, the object of the present invention is to provide DNA fragments having an autonomous replicability and a function for enhancing the transformation efficiency, plasmid vectors containing the fragments, a process for integrating a selectable marker gene-free DNA fragment into chromosome with the plasmid vector, as well as a process for obtaining DNA sequences having promoter activity and novel DNA sequences having the promoter activity obtained thereby.

The novel DNA sequences according to the present invention includes a gene encoding the ribosomal protein L41 of *Candida utilis* and its promoter and terminator sequences; a cycloheximide resistance L41 gene; promoter and terminator sequences of the phosphoglycerate kinase (PGK) gene; promoter and terminator sequences of the glyceraldehyde-3-phosphate-dehydrogenase (GAP) gene; promoter and terminator sequences of the plasma membrane proton ATPase (PMA) gene; the URA3 gene and its promoter and terminator sequences; two DNA fragments having an autonomous replicability; sequences having promoter activity; and the ribosomal RNA genes encoding the rRNAs of *Candida utilis*.

The vector which may be used in the transformation system of *Candida utilis* according to the present invention comprises a sequence homologous to the chromosomal DNA of *Candida utilis* and a selectable marker gene, wherein a heterologous gene is capable of being integrated into the chromosomal DNA by homologous recombination, or comprises a DNA sequence having an autonomous replicability in *Candida utilis* and a selectable marker gene, wherein *Candida utilis* is transformed at high frequency.

In addition, the vector which may be used in the transformation system of *Candida utilis* according to the present invention comprises no selectable marker gene and a sequence homologous to the chromosomal DNA of *Candida utilis*, wherein a heterologous gene is capable of being integrated into the chromosomal DNA by homologous recombination. The plasmid can be used in transformation together with a plasmid comprising a DNA sequence having an autonomous replicability and a selectable marker gene.

Furthermore, the selectable marker gene which may be used in the transformation system of *Candida utilis* according to the present invention is a drug-resistant marker which can function in *Candida utilis*, preferably the L41 gene conferring cycloheximide resistance, a gene conferring resistance to G-418, or a gene conferring resistance to hygromycin B.

Furthermore, the process for expressing heterologous genes in *Candida utilis* according to the present invention comprises transforming *Candida utilis* with the vector according to the present invention containing the heterologous gene, culturing the transformant thus obtained, isolating and purifying the expression product of the heterologous gene from the culture.

In addition, the transformant of *Candida utilis* according to the present invention refers to the one obtained by the functional combination of the novel DNA group, the vector systems and the like according to the present invention.

BRIEF DESCRIPTION OF THE DRAWINGS

FIG. 1 illustrates the restriction enzyme map, the strategy for determining the DNA sequence of plasmids containing the phosphoglycerate kinase (PGK) gene, and a process for obtaining the promoter and terminator fragments by PCR;

FIG. 2 illustrates the DNA sequence of a DNA fragment containing the PGK terminator (SEQ ID NO:1);

FIG. 3 illustrates the DNA sequence of a DNA fragment containing the PGK promoter (SEQ ID NO:2);

FIG. 4 illustrates a diagram for constructing expression vector plasmids with the PGK gene promoter and terminator;

FIG. 8 illustrates the strategy for determining the DNA sequence of URA3 gene, and the restriction enzyme map of it;

FIG. 9 illustrates the DNA sequence of a DNA fragment containing the URA3 gene (SEQ ID NO:3);

FIG. 10 illustrates the amino acid sequence (SEQ ID NO:4) deduced from the DNA sequence of the, URA3 gene, and the DNA sequence of the DNA encoding it (bases 1259–2059 of SEQ ID NO:3);

FIG. 11 illustrates the continuation of FIG. 10, which are the amino acid sequence deduced from the DNA sequence (SEQ ID NO:4) of the URA3 gene, and the DNA sequence of the DNA encoding it (bases 1259–2059 of SEQ ID NO:3);

FIG. 12 illustrates the restriction enzyme maps of plasmids containing L41 gene, and the strategy for determining the DNA sequence;

FIG. 13 illustrates the DNA sequence, of a DNA fragment containing L41 gene (SEQ ID NO:5);

FIG. 14 illustrates the amino acid sequence deduced from the DNA sequence of the L41 gene (SEQ ID NO:6), and the DNA sequence of the DNA encoding it (bases 1115–1481 of SEQ ID NO:5);

FIG. 21 illustrates the electrophoresis patterns of the results of the Southern blot analysis of the DNA of ATCC 9950 strains transformed with plasmids pCLRE4, pCLRE5, pCLRE6 and pCLRE7;

FIG. 23 illustrates the construction of plasmids pCLSTA1 and pCLRSTA1;

FIG. 30 illustrates the DNA sequence of the DNA fragment containing the GAP gene promoter (SEQ ID NO:7);

FIG. 31 illustrates the DNA sequence of the DNA fragment containing the GAP gene terminator (SEQ ID NO:8);

FIG. 32 illustrates the construction of expression vector plasmids with the GAP gene promoter and terminator;

FIG. 34 illustrates the DNA sequence of a DNA fragment containing the PMA gene promoter (SEQ ID NO:9);

FIG. 35 illustrates the DNA sequence of a DNA fragment containing the PMA gene terminator (SEQ ID NO:10);

FIG. 37 illustrates the structure of vector pGKAPH2 for cloning of DNA fragments containing ARS;

FIG. 39 illustrates the restriction enzyme maps of insertion DNA fragments of plasmid pCARS6 and four plasmids which contain subcloned DNA fragments of the plasmid pCARS6;

FIG. 40 illustrates the restriction enzyme maps of insertion DNA fragments of plasmid pCARS7 and five plasmids which contain subcloned DNA fragments of the plasmid pCARS7;

FIG. 41 illustrates the DNA sequence of an inserted DNA fragment of the plasmid pCARS6-2 (SEQ ID NO:11);

FIG. 42 is the continuation of the DNA sequences of FIG. 41, which illustrates the DNA sequence of an inserted DNA fragment of the plasmid pCARS6-2 (SEQ ID NO:11);

FIG. 43 illustrates the DNA sequence of an inserted DNA fragment of the plasmid pCARS7-6 (SEQ ID NO:12);

FIG. 44 is the continuation of the DNA sequences of FIG. 43, which illustrates the DNA sequence of an inserted DNA fragment of the plasmid pCARS7-6 (SEQ ID NO:12);

FIG. 47 illustrates the construction of promoter cloning vector pPCV2;

FIG. 48 illustrates the DNA sequence (SEQ ID NO:13) of a DNA fragment having the promoter activity of plasmid pPCRV19;

FIG. 50 illustrates the electrophoresis patterns of the result of the PCR analysis of DNA of the ATCC 9950 strains transformed by the co-transformation method.

DETAILED DESCRIPTION OF THE INVENTION

Yeast *Candida utilis*

Figure 5:
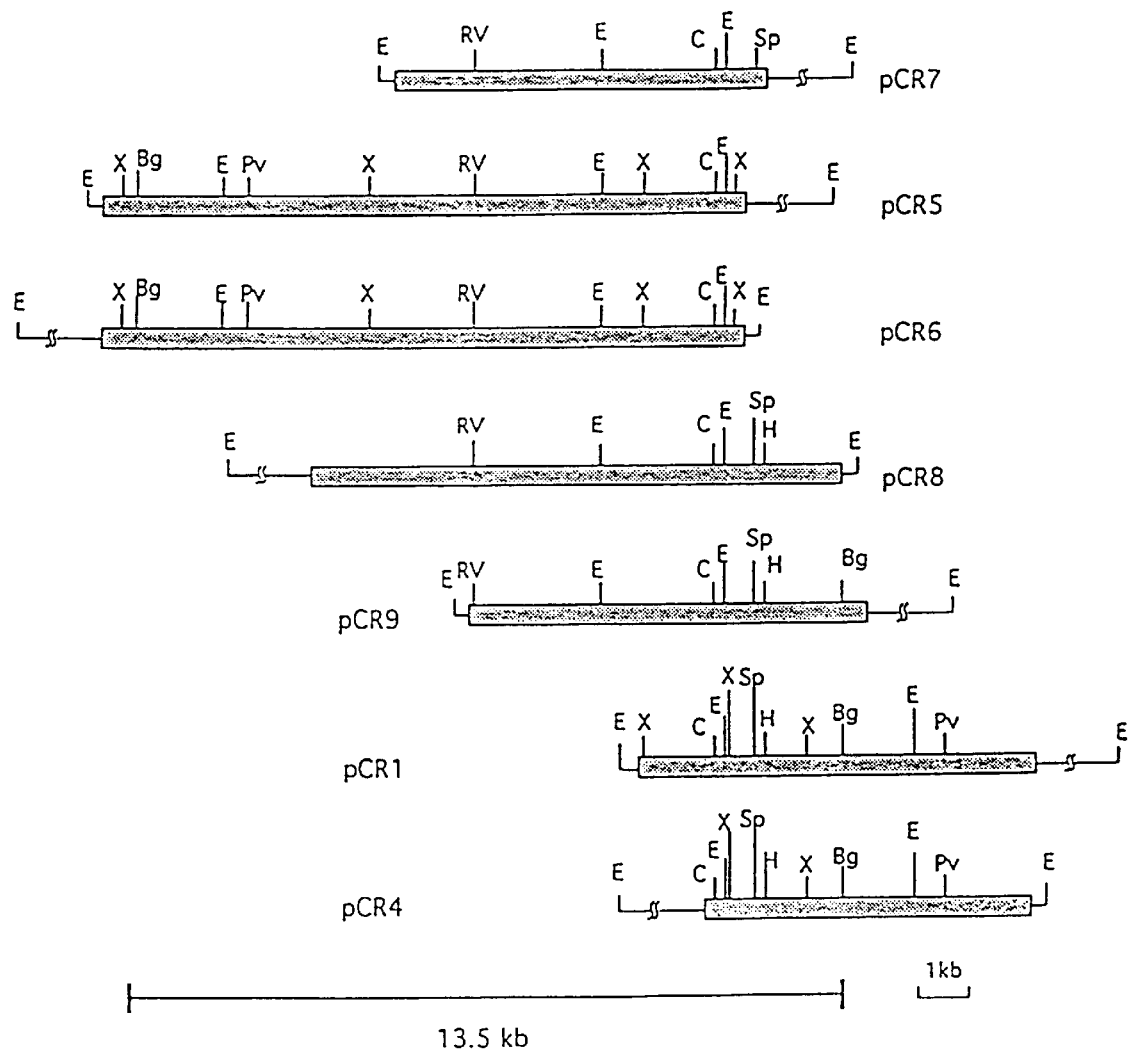
FIG. 5 illustrates the restriction enzyme maps of plasmids containing the ribosomal DNA.

Specific strains of *Candida utilis* to which the transformation system according to the present invention can be applied include for example ATCC 9256 (IFO 0626), ATCC 9226 (IFO 1086), ATCC 9950 (IFO 0988), IFO 0396, IFO 0619, IFO 0639, and KP-2059P.

It has also been reported that electrophoresis pattern of chromosomes varies among the strains of *Candida utilis* and it shows the polymorphism in length of chromosomes [Stoltenburg et al., Curr. Genet., 22, 441–446 (1992)]. It was expected that the transformation system according to the present invention is limited in its application due to its polymorphism. However, transformants were obtained and the expression of heterologous genes were also confirmed with either of the three strains employed in Examples described below, while chromosomal polymorphism was observed in the three strains. It would be anticipated for a person skilled in the art that the transformation system according to the present invention can be applied to *Candida utilis* on the whole.

Transformation System

In order to develop a transformation system of organisms, there are generally required three elements (a) a selectable marker gene to select transformants, and a method for selecting transformants, (b) an autonomously replicable DNA sequence (ARS) required for the presence of a plasmid DNA as an episome in a host cell, or the homologous sequence of an appropriate chromosomal DNA required for efficiently integrating a plasmid into a chromosome (that is, the establishment of a target for integrating the plasmid DNA), and (c) a method for making a host cell capable of taking up an extranuclear DNA. All of the three elements are required for obtaining transformants. It was thus essential to examine and develop all of these elements for establishing the transformation system of *Candida utilis* where few genetic information have been obtained.

(a) Selectable marker genes and selection of transformants

When an auxotrophic mutant obtained by mutation treatment can be used as a host, a gene which can complement the auxotrophy can be used as a selectable marker gene in order to select transformants. In this case, it is possible to select directly transformants in the minimal medium which is free of the nutrient. However, in the case of *Candida utilis*, it was impossible to develop a transformation system using an auxotrophic complementary gene as a selectable marker, since it was very difficult to obtain a mutant strain to which an appropriate selective mark such as an auxotrophy was added.

The present inventors have found that *Candida utilis* is sensitive to drugs such as an antibiotic G418, hygromycin B or cycloheximide, and it is possible to suppress growth by adding these drugs into the medium. The present inventors have thus tried to use a gene which would confer resistance to these drugs.

Thus, when a gene derived from the other organisms such as the G418 resistance gene (aminoglycoside phosphotransferase gene) or the hygromycin B resistance gene (hygromycin B phosphotransferase gene) is used, it is preferred to use transcriptional promoter and terminator sequences which function in *Candida utilis* to ensure the expression of the gene.

In some of the yeasts in the Candida genus such as *Candida albicans*, it has been described that some of the codons are translated in a mode different from that in other organisms (Ohama et al., Nucleic Acids Res., 21, 4039–4045, 1993). Thus, a heterologous gene used as a selectable marker gene may not be always translated into a protein having its function in the host. On the other hand, there has been described the very interesting fact that the sensitivity to cycloheximide is determined by an amino acid residue at 56th position of the ribosomal protein L41 protein [Kawai et al., J. Bacteriol., 174, 254–262 (1992)].

The present inventors have thus obtained a gene of the L41 protein of *Candida utilis* which is sensitive to cycloheximide, converted the gene into the cycloheximide resistance gene by the site specific mutation method, and used it as a selectable marker gene. Since the gene was derived from the host, the gene was directly used with its own promoter and terminator sequences for the expression. Therefore, this embodiment is very advantageous in the point that the gene can be surely anticipated for expression.

Thus, the drug-resistance gene marker used as a selectable marker in the transformation system of *Candida utilis* according to the present invention is preferably a cycloheximide resistance L41 gene. The DNA sequence of a DNA fragment containing the L41 gene as well as the promoter and terminator sequences is shown in FIG. 13 (SEQ ID NO: 5), and the amino acid sequence deduced from the DNA sequence is shown in FIG. 14 (SEQ ID NO: 6). The cycloheximide resistance L41 gene has a sequence shown in FIG. 13 where the 1644th nucleotide C has been converted into A, and the 56th amino acid, Pro, in the sequence shown in FIG. 14 is converted into Gln.

In addition, another preferable drug resistance gene marker which may be used in the transformation system according to the present invention is the aminoglycoside phosphotransferase (APT) gene which confers resistance to the antibiotic G418. As the aminoglycoside phosphotransferase (APT) gene, two APT genes derived from transposon Tn903 and transposon Tn5 have been known in the art, and either of the two may be used in the present invention. It is also possible to use the hygromycin B phosphotransferase gene derived from *E. coli* which confers resistance to the antibiotic hygromycin B in the transformation system according to the present invention. In the case of these heterologous genes such as G418 resistance gene or hygromycin resistance gene, transcriptional promoter and terminator which function in *Candida utilis* for genetic expression are preferably integrated at the 5'-upstream and the 3'-downstream of the heterologous gene, respectively.

The promoter and terminator sequences for transcription are preferably derived from the gene of *Candida utilis*. It is possible to use the promoter and terminator sequences of the phosphoglycerate kinase (PGK) gene, the promoter and terminator sequences of the glyceraldehyde-3-phosphate dehydrogenase (GAP) gene, and the promoter and terminator sequences of the plasma membrane proton ATPase (PMA) gene in *Candida utilis* described hereafter. It is also possible to use DNA sequences having promoter activity obtained with a vector for the cloning of promoters described below.

In addition, the other promoter and terminator sequences which can be used in the above described system include promoter and terminator sequences of the genes in *Candida utilis* homologous to the well-known genes such as ADH, ENO, GAL and SUC in the yeast of the genus Saccharomyces.

Furthermore, drug-resistance genes derived from bacteria which may be used as selectable markers for transformants include, in addition to the above described G418-resistance gene and a hygromycin B phosphotransferase gene, antibiotic-resistance genes such as the chloramphenicol acetyltransferase gene (chloramphenicol-resistance) (Hadfield, C. et al., Gene, 45, 149–158 (1986)), the blasticidin deaminase (blasticidin-resistance) (Izumi, M. et al., Exp. Cell Res., 197, 229–233 (1991)), and the phleomycin-resistance gene (Wenzel, T. J. et al., Yeast, 8, 667–668 (1992)). In addition, well-known drug-resistance genes such as the dihydrofolate reductase gene (methotrexate-resistance) (Miyajima, A. et al., Mol. Cell Biol., 4, 407–414 (1984)), the methyl sulfometuron-resistance gene which is a dominant gene derived from yeast (Casye, G. P. et al., J. Inst. Brew., 94, 93–97 (1988)), the CUP1 gene (copper-resistance) (Henderson, R. C. A. et al., Current Genet., 9, 133–138 (1985)), and the CYH2 gene (cycloheximide-resistance) (Delgado, M. et al., EBC Congress, 23, 281–288 (1991)) may be used. When the marker gene is derived from a heterologous organism such as bacteria or transposon, it is preferred to use promoter and terminator sequences which function in *Candida utilis* described above.

(b) Establishment of targets for integration of plasmid DNA

As described above, since applicable selectable markers such as the cycloheximide-resistance L41 gene have been established according to the present invention, it is anticipated that a variety of sequences derived from *Candida utilis* in addition to those sequences described above can be used as target sequences.

According to the preferred embodiment of the present invention, it has been found that the gene encoding ribosomal RNA (rDNA), the URA3 gene, the L41 gene, and the PGK gene can be preferably used as appropriate chromosomal DNA fragments required for integrating a plasmid into a chromosome.

As for the rRNA gene, it has been described that 100 copies or more of rDNA are present in tandem on the chromosome of *Saccharomyces cerevisiae,* and an autonomously replicating sequence (ARS) is present in the repeating unit (Saffer & Miller, JR. Molec. Cell. Biol., 6, 1148–1157 (1986)). It has been also described that the frequency of integrative transformation can be increased by using the rDNA region as the target for integration of a plasmid (Lopes, et al., Gene, 79, 199–206 (1989)).

The present inventors have found that rDNA is present repeatedly on the chromosome of *Candida utilis.* It has been thus indicated that the rDNA of *Candida utilis* can be used as a target sequence for integration in high frequency, and indeed the rDNA was advantageously used as a recombination target in the transformation system of *Candida utilis.*

It has been interestingly observed that when the yeast of *Candida utilis* was transformed with the vector systems according to the present invention described below which target at chromosome of *Candida utilis* such as the rRNA gene, the URA3 gene, the L41 gene or the PGK gene, a DNA fragment was integrated into the chromosome and retained stably in the yeast. It is thus possible to exclude the problem of instability of a heterologous gene in the case that a heterologous gene is retained as an extrachromosomal plasmid which replicates autonomously.

It has been found as a result of the intensive analysis of the mode of DNA fragments integrated in transformants that the DNA fragments are integrated into the chromosome of *Candida utilis* mainly by homologous recombination. This means that a DNA molecule containing a DNA sequence which has a homology to the chromosomal target sequence of a host may be integrated into any chromosomal target.

Specifically, it is possible to integrate a DNA fragment at any target sequence on the chromosome of *Candida utilis* when the vector containing the DNA fragment is digested at an appropriate restriction site in the DNA sequence homologous to the target sequence to be a linear plasmid DNA. In this case, when cycloheximide-resistance L41 gene is used as a selectable marker, transformants in which a plurality of plasmid molecules have been integrated at the same time are selected efficiently as described below.

It is also possible to use a linear DNA fragment in the form that a selectable marker is contained within a DNA sequence having homology to a chromosomal target sequence.

In the transformation of this embodiment according to the present invention, the DNA fragment is inserted to chromosome and replace the homologous gene on chromosome. Thus, no repetitive sequences of the target sequence is thus formed at upstream and downstream of the DNA fragment inserted. It is expected for the DNA integrated to have higher stability.

In addition, the present invention has indicated that the URA3 gene, the L41 gene, and the PGK gene which are present in only two copies per cell as well as many other genes can be used as targets for integrating a DNA fragment. In general, yeast contains 100 copies or more repetitive DNA unit containing rRNA genes of 18S, 5.8S, 25S and 5S per haploid (Schweizer, E. et al., J. Mol. Biol., 40, 261–277 (1969)). Therefore, the use of the rDNA as a target sequence of recombination is advantageous over the use of the other gene sequences in the points that (1) the frequency of transformation is expected to be increased, and (2) the change in the target sequence by integration is negligible.

The present inventors have showed that the rRNA genes are repetitively present in tandem in a repetitive unit of about 13.5 kb DNA sequence also in *Candida utilis* (described in details below), and that the transformation frequency is increased 10- about 50 times by using the rDNA sequence as the target sequence of recombination as compared to the case of the L41 gene having 2 copies per cell as a target. It has been also shown that DNA fragments in the rDNA locus have high stability and the rDNA sequence is an excellent target for integration.

The use of the rDNA sequence as a target sequence for integrating a DNA fragment in the present invention has brought about the effect for increasing transformation frequency and played an important role for the discovery of a proper transformation condition among the treatment conditions of yeast examined. However, it has been found interestingly that the frequency of transformation is decreased extensively when some of the rDNA regions are used as targets of transformation. It has been indicated that any of the rDNA fragments is not always used as a target for efficiently integrating plasmids.

According to the further preferred embodiment of the present invention, transformants having a plurality of plasmids integrated therein can be obtained efficiently by using cycloheximide-resistance L41 gene as a selectable marker. The reason is considered as follows. Only when plural copies of DNA fragments containing the cycloheximide-resistance L41 genes are integrated, the ratio of ribosome molecules in which the endogenous cycloheximide sensitive L41 proteins are replaced by the corresponding resistant proteins and are not inhibited in functions by cycloheximide is increased. It is thus considered that the transformant can grow in the medium containing cycloheximide. As the target site for integration in this case, basically either of the sequences can be used which is derived from the chromosome of *Candida utilis* such as the URA3 gene locus, the L41 gene locus or the like. It was also shown interestingly that the more DNA fragments tend to be integrated by using the rRNA gene locus inter alia as a target sequence for integration as compared with the other gene loci as target sequences.

(c) Transformation method

As the method of transformation which makes a host cell capable of easily taking up an extracellular DNA, the conventional methods of the transformation of *Saccharomyces cerevisiae* such as the protoplast method, the lithium acetate method, the electric pulse method, and modifications thereof can be employed. While the protoplast method is widely used, it is rather complicated in operation and often causes the problem of background colonies as non-transformants in the selection of transformants based on drug-resistance.

The present inventors have employed the lithium acetate method and the electric pulse method to try the transformation of *Candida utilis* with a plasmid as a combination of the cycloheximide-resistance L41 gene and the rDNA fragment described above, and found the conditions in which transformants can be obtained reproducibly.

The transformation is preferably carried out by the electric pulse method. Cells are grown up to a logarithmic phase, and then washed and suspended into 1M sorbitol. The condition of electric pulse includes the time constant value (period of time for attenuating the voltage to about 37% of the maximum) of about 10–20 milliseconds, and the viable cell ratio after the pulse of about 10–40%. For instance, it has been shown according to the preferred embodiment of the present invention that the above described time constant value and the viable cell ratio were obtained under the conditions of an electric capacitance of 25 μF, a resistance of 600–1,000Ω, and a voltage of 3.75–5 KV/cm, and about 500–1,400 transformants per 1 μg of DNA were obtained.

It has been also found that after electric pulse was applied, a YPD medium containing 1M sorbitol is preferably added to the cell solution, and the mixture is shake cultured. It has been also found that if the cells without culture are directly spread on a selective plate containing cycloheximide, no colony is obtained in some cases. The culturing time is appropriately in the range of about 4–6 hours, and if the cells are cultured further, the growth of the transformants cannot be negligible. Moreover, it is preferred for the transformation according to the present invention to enhance the transformation frequency by adding a carrier DNA such as salmon sperm DNA on the contact of the DNA and the cells or by adding polyethylene glycol.

The lithium acetate method (Ito et al., J. Bacteriol., 153, 163–168, 1983) has been extensively used in the transformation of a yeast of the genus Saccharomyces because of its simplicity and easiness. A variety of modifications have been also described. We have confirmed that *Candida utilis* may be transformed with these methods. In particular, it is preferably to transform *Candida utilis* with the modified lithium method in which ethanol is added (Soni et al., Current Genet., 1993, 24, 455–459). It is also possible to determine the optimal condition for the transformation of *Candida utilis* by the lithium acetate method and to enhance the transformation frequency by using different conditions such as the cell densities on collecting the cells, the lithium concentrations, the kinds and concentrations of polyethylene glycol, and the kinds, forms or amounts of a carrier DNA. These methods are anticipated by a person skilled in the art, since (a) selectable marker genes according to the present invention and (b) targets for integration has been thus defined.

In addition, we have tried to carry out transformation with plasmids containing a combination of eight ARS sequences derived from *Candida utilis* which function in *Saccharomyces cerevisiae* and a G418-resistance gene expressing unit which functions in *Saccharomyces cerevisiae*, but no transformant was obtained. The reproducibility of the transformation of *Candida utilis* described by Ho et al (Ho, N. W. Y. et al., ditto) is thus doubtful because of the result.

Expression Vector Systems and Expression of Heterologous Genes

According to the present invention, there provides expression systems which can be used for the transformation of *Candida utilis*.

An embodiment of the present invention is a plasmid DNA which comprises a sequence homologous to a chromosomal DNA of *Candida utilis* (referred to hereinafter as "homologous DNA sequence"), which makes possible the integration of the plasmid DNA into the chromosome by homologous recombination at this portion, and a selectable marker for the selection of transformants.

The homologous DNA sequence preferably includes the rRNA gene, the URA3 gene, the L41 gene, the PGK gene, the GAP gene, and the PMA gene, which are preferably derived from the chromosomal DNA of *Candida utilis*. It is possible to integrate a heterologous gene into a desired position of a chromosome depending on sequences used. The plasmid is used in the linear form by the digestion at an appropriate restriction site within the homologous DNA sequence of the plasmid molecule. As a result, the plasmid DNA fragment is integrated into the chromosome of *Candida utilis* by homologous recombination.

In addition, according to the preferred embodiment of the present invention, the DNA sequence containing a marker gene and a heterologous gene is inserted at its both terminals between the homologous DNA sequence within the plasmid DNA. In this embodiment, the plasmid DNA is cut at the homologous DNA sequence with restriction enzyme to obtain a DNA fragment comprising a marker gene, a heterologous gene, and the homologous DNA sequence at both terminals of the fragment. The DNA fragment thus obtained can be also integrated into the chromosomal DNA of *Candida utilis* by homologous recombination.

The term "the DNA fragment thus obtained is integrated into the chromosome of *Candida utilis* by homologous recombination" herein, while its embodiment for integration is not limited as far as the DNA fragment is integrated into the chromosome of *Candida utilis*, refers to the meaning containing at least two embodiments as follows. That is, the term refers to either of the meanings (1) an embodiment being integrated into a chromosomal DNA by causing homologous recombination of the DNA sequence of the chromosome of *Candida utilis* and homologous DNA sequence portions at the both terminals of the DNA fragment, which is "inserted" into the cleaved portion; and (2) an embodiment being integrated into a chromosomal DNA by replacing a part of the chromosome of *Candida utilis* with the plasmid DNA fragment by the homologous recombination of the DNA sequence of the chromosome of *Candida utilis* and the homologous DNA sequences provided at the both terminals of the plasmid DNA fragment. In the embodiment of (2), the DNA fragment integrated is anticipated to be present stably in the chromosome, since the repetitive sequences of the target sequence are not formed at the both terminals thus inserted.

It is also preferred to use the above described drug-resistance marker as the selectable marker gene, and more preferred drug-resistance marker includes a gene conferring resistance to cycloheximide such as the cycloheximide-resistance L41 gene, the gene conferring resistance to an antibiotic G418 such as the APT gene derived from a bacterial transposon Tn903, and the antibiotic hygromycin B-resistance gene. When the selectable marker gene is derived from microorganisms, it is preferred to ligate it to a promoter which functions in *Candida utilis* to ensure the expression.

The vector according to another embodiment of the present invention is a plasmid DNA which comprises a sequence homologous to a chromosomal DNA of *Candida utilis* (homologous DNA sequence), which makes possible the integration of the plasmid DNA into the chromosome by the homologous recombination at this portion, but no selectable marker for the selection of transformants. The plasmid is used in the linear form by digestion at an appropriate restriction site within the homologous DNA sequence of the plasmid molecule.

In the plasmid of this embodiment, the plasmid may be constructed so that the DNA sequence containing a heterologous gene is inserted at its both terminals between the homologous DNA sequences. A DNA fragment having at its both terminals homologous DNA sequences is obtained by cutting the plasmid DNA at the homologous DNA sequence with restriction enzyme. The DNA fragment can also be integrated into the chromosomal DNA of *Candida utilis* by the homologous recombination.

The DNA fragment in the linear form is integrated into the chromosome of *Candida utilis* by homologous recombination in the same manner as in the case of plasmid DNA comprising a marker gene. It is also anticipated in the plasmid of this embodiment that the DNA fragment integrated is present stably in a chromosome by the integration according to the embodiment (2) described above.

The homologous DNA sequence includes preferably the rRNA gene, the URA3 gene, the L41 gene, the PGK gene, the GAP gene, and the PMA gene. These genes are preferably derived from the chromosomal DNA of *Candida utilis*. It is also possible to integrate a foreign DNA fragment at a desired position on a chromosome depending on the sequences used.

The vector is used in transformation simultaneously with a plasmid having a DNA sequence containing an autonomously replicating sequence described below and a selectable marker gene. It is possible to select secondarily a strain that the selectable marker gene-free DNA fragment has been integrated in the chromosome among transformants which are selected by having the autonomously replicable plasmid therein. The plasmid present in the selected strain can be dropped out by culturing the cell under a non-selective condition. As a result, a strain which retains only the inserted DNA fragment on the chromosome can be obtained. With this technique, it will be possible to grow for example a strain which retains only a heterologous gene and is free of extra sequences like a drug-resistance gene derived from microorganisms.

Furthermore, a plasmid having a DNA sequence containing the autonomously replicating sequence and a selectable marker gene can be used as a vector for the transformation of the yeast *Candida utilis*. The plasmid tends to be dropped by culturing the cell under a non-selective condition, but a DNA fragment for enhancing stability can be obtained as described below, so that the plasmid can be used in combination with the DNA fragment as a vector.

The vector according to the present invention can be linked to a heterologous gene to form a vector having the heterologous gene retained therewith. By the transformation of *Candida utilis* with the vector, the heterologous gene can be integrated stably into the chromosome of *Candida utilis*. The transformant thus obtained can be cultured in an appropriate medium to give the culture product, from which the expression product of the heterologous gene is isolated and purified by the method suitable for the expression product. That is, the heterologous gene can be expressed *Candida utilis*. The process for expressing a heterologous gene in *Candida utilis* is provided. In this context, the term heterologous gene generally refers to a gene or a DNA as a part thereof which is not originally present on the chromosome of *Candida utilis* as a host.

The heterologous gene is preferably combined with a regulatory region which regulates independently the expression of the heterologous gene or expressed under the influence of the regulatory region of the gene disrupted by the process of transformation. Such sequences should function in *Candida utilis*, and include preferably for example the promoter sequence and the terminator sequence of the PGK gene, the GAP gene and the PMA gene according to the present invention which is described below, and DNA sequences having promoter activity obtained by a vector for cloning the promoter described below.

As apparent from examples described below, heterologous genes such as the glucoamylase gene, the aminoglycoside phosphotransferase gene, the β-galactosidase gene and the hygromycin B phosphotransferase gene have been successfully expressed with the promoter sequence and the terminator sequence of the phosphoglycerate kinase gene according to the present invention. An aminoglycoside phosphotransferase gene has been also successfully expressed with the promoter and terminator sequences of glyceraldehyde-3-phosphate dehydrogenase gene as well as with the promoter and terminator sequences of plasma membrane proton ATPase gene. Among these heterologous proteins, glucoamylase is an secreted protein, and aminoglycoside phosphotransferase and β-galactosidase are intracellular enzymes. This means that a heterologous protein in either of an intracellular or secreted protein can be produced in *Candida utilis*. Furthermore, glucoamylase is also secreted and expressed at a high level, and it can be said that *Candida utilis* is an excellent host for the high production of a heterologous protein.

Furthermore, it has been described that in some of the yeasts of the genus Candida such as *Candida maltosa*, or *C. albicans*, a part of codons are translated in a mode different from that in the other organisms (Ohama et al., Nucleic Acids Res., 21, 4039–4045 (1993)). This is interpreted to be the reason why the expression product of the β-galactosidase gene derived from *E. coli* which has been expressed in *Candida maltosa* as a host exhibits no activity. As apparent from the examples below, a galactosidase gene product derived from *E. coli* which has been produced in *Candida utilis* retained its activity. This shows that *Candida utilis* recognizes codons in normal manner, and that *Candida utilis* is a preferred host in the production of a heterologous polypeptide.

It is also possible to modify the properties of *Candida utilis* by expressing a heterologous gene in *Candida utilis*. Thus, according to the present invention, a process for creating a novel *Candida utilis* strain is provided. For instance, it is possible to improve its fermentation properties for increasing its industrial utility. In particular, a *Candida utilis* strain which is modified to express a glucoamylase gene will have starch digesting ability, i.e., its carbon source spectrum is expanded.

Furthermore, the vector according to the present invention can be used in the transformation of cells other than *Candida utilis*. When a cell other than *Candida utilis* is used as a host, a DNA fragment suitable for the practice of transformation is preferably selected. The DNA fragment includes for example a bacterial plasmid DNA such as pBluescript or pUC19 in the case of *E. coli*. The DNA fragment includes for example a yeast-*E. coli* shuttle vector such as YEp13 or YCp50 (Methods in Enzymology, 194, p. 195–230, Academic Press (1991)) in the case of a yeast of the genus Saccharomyces.

Method for Cloning of DNA Sequences having Autonomous Replicability in the Yeast *Candida utilis*

Furthermore, according to the present invention, a method for cloning the DNA sequence having an autonomous replicability in *Candida utilis* is provided. The DNA used, which may be derived from any organisms, is preferably derived from *Candida utilis*. As a vector for this method, a vector containing a drug-resistance marker gene can be used. Preferred examples include a vector containing the APT gene which is a G418-resistance gene and is expressed by a promoter and a terminator functioning in *Candida utilis*. Specifically, a plasmid having the APT gene which is expressed by the PGK gene promoter is used as a vector to prepare a genomic DNA library of the *Candida utilis* yeast, and *Candida utilis* is transformed with the library DNA. Total DNA is extracted from a transformed yeast selected on the basis of resistance to G418. *E. coli* is transformed with the DNA, so that the plasmid DNA present in the transformed yeast as an extrachromosomal factor can be recovered. Functional sequences as autonomous replicating sequence (ARS) are isolated from the chromosomal DNA fragment derived from *Candida utilis* inserted in the plasmid DNA.

Surprisingly, when a plasmid containing the cycloheximide-resistance L41 gene as a marker of resistance to drug is used as a vector, any DNA sequence having an autonomous replicability could be cloned. In other words, even if the plasmid was urea for preparing a *Candida utilis* yeast genomic DNA library and *Candida utilis* was transformed with the library DNA, no cycloheximide-resistant transformant was obtained. This indicates that the ARS of *Candida utilis* has a feature of producing a low number copies per cell of the plasmid containing it, so that a transformant cannot be selected even if it is combined with the cycloheximide-resistance L41 gene which requires several copies in order to select the transformant. This has been further confirmed by the fact that no transformant was obtained even by transforming *Candida utilis* with a plasmid containing the ARS thus obtained and the cycloheximide-resistance L41 gene. As shown in examples below, it has been clarified by analyzing extensively the properties of the DNA sequence containing the ARS cloned that the plasmid containing ARS is present in only about one copy per cell of the *Candida utilis* yeast. In addition, the ARS thus cloned has also a feature that the plasmid containing it is instable. When the *Candida utilis* yeast was cultured for about 2.5–3.5 generations under a non-selective condition, the ratio of the cells containing the plasmid was lowered to 20–30% of the total number of cells.

Process for Cloning DNA Sequences having Promoter Activity in *Candida utilis*

The process for cloning the DNA sequences having transcriptional promoter activity in *Candida utilis* is provided by using the DNA sequence having the above autonomous replicability. As the vector therefor, a vector having, in addition to the DNA sequence having the autonomous replicability, a drug-resistance gene free of a promoter sequence for transcription may be used. A vector containing the APT gene which is a G418-resistance gene can be preferably used. DNA used may be derived from any organisms, preferably derived from *Candida utilis*. In addition, the DNA has to be converted to small molecules for preparing a library by enzyme treatments with restriction enzymes or DNAase or by mechanical shear with ultrasonic waves. A combination of three restriction enzymes of AluI, HaeIII and RsaI which recognize four nucleotides in length and generate blunt ends is preferably used for the partial degradation of the chromosomal DNA. With this combination, more chromosomal regions are cloned in the library.

More specifically, the *Candida utilis* yeast genomic DNA library is prepared by the conventional method in which about 0.8–1.8 kb DNA fragments which have been partially digested with the above restriction enzymes are linked to the 5' side of the promoter sequence-free APT gene. Further, *Candida utilis* is transformed with the library DNA. The yeast transformed with the plasmid in which the DNA sequence having a promoter activity has been cloned immediately before the APT gene becomes G418 resistant. Thus, the total DNA is extracted from the G418-resistant transformant to transform *E. coli* and the DNA sequence having a promoter activity can be cloned efficiently. In this case, promoter sequences having higher transcriptional activities can be isolated by increasing the concentration of G418 contained in the plate or selecting a strain which forms a relatively large colonies on the plate. The method according to the present invention is advantageous for separating a promoter sequence having a high activity, since the number of copies of the plasmid containing ARS in *Candida utilis* remains about 1 per cell as described above.

Process for Isolating the Other Functional Genes of *Candida utilis*

Furthermore, the process for isolating DNA having a promoter activity in *Candida utilis* according to the present invention also provides a process for isolating DNA sequences having a function for improving the stability of the plasmid containing ARS. An embodiment of the plasmid containing ARS in *Candida utilis* is characterized in that it has a low stability, and on culturing for 3–4 generations under a non-selective conditions the cells retaining the plasmid are decreased to 20–30% of the total cells. Therefore, on the plate containing a selective drug, a strain which retains ARS plasmid containing the drug-resistance gene forms slightly smaller colonies as compared with a strain that the drug-resistance gene has been integrated on chromosome notwithstanding the number of copies per cell being the same. In the present invention, strains which form relatively large colonies were selected for separating promoter sequences having high activity, so that some of the separated DNA having promoter activity, as described in Examples below, have functions which can improve the stability of the plasmid. Moreover, it can be anticipated for a person skilled in the art that the use of this transformation system makes it possible to get DNA sequences having a variety of functions such as a centromere sequence.

Process for Producing a Transformant Free from Drug-resistance Marker Gene

Another process for producing a transformant free from drug-resistance marker gene is provided by using the above DNA sequence having autonomous replicability according to the present invention. Specifically, a transformant free from drug-resistance marker gene can be obtained by the following procedure. First, a plasmid DNA having no selectable marker gene for selecting the transformant and containing a sequence homologous to the chromosomal DNA (homologous DNA sequence) is digested at an appropriate restriction enzyme site in this homologous DNA sequence into a linear form. The linear plasmid DNA thus can be integrated on the homologous DNA sequence of the chromosome of *Candida utilis*. The linear plasmid DNA is used together with a plasmid having DNA sequence containing an ARS and a selectable marker gene for the transformation of yeast. Among the transformants selected by the introduction of the plasmid containing ARS, clones in which the DNA fragment used for the transformation at the same time has been integrated in the chromosome is secondarily selected by trying the expression of heterologous genes contained in the DNA fragment or by confirming the integration of the DNA fragment by PCR or Southern analysis. Furthermore, the autonomously replicable plasmid present in the selected strain can be easily removed by culturing the cells under a non-selective condition. It is thus possible to obtain a strain which is free of a selectable marker gene and retains only the inserted DNA fragment on the chromosome.

Site-specific Mutagenesis of Chromosome of *Candida utilis*

According to another embodiment of the present invention, a site-specific mutagenesis of chromosome of Candida utilis is provided. In this method, a gene fragmentation cassette in which a selectable marker gene has been inserted into a target gene to lose its function is used as a substituent of the chromosomal target gene. The cassette has a linear DNA structure which comprises at the both ends DNA sequences homologous to a chromosomal target gene (homologous DNA sequence) and at least one selectable marker gene between them. It is important that the DNA fragment which can be inserted has the same direction as it is on the chromosome. When yeast is transformed with the cassette, the marker gene and the DNA sequences which are present at its both sides and can be inserted are integrated into the host. As a result of the transformation, the target gene at the integration site is disrupted and a yeast strain having a novel character is obtained. The selectable marker gene is preferably a drug-resistance gene, and the transformants of which the genes have been disrupted can be selected by resistance to the drug. The gene which can be a target of this gene modification is preferably a gene derived from the chromosome of Candida utilis. Specifically, it includes URA3, ADE1, ADE2, or HIS genes, but it is not limited thereto.

For instance, the Candida utilis URA3 gene is split with a selectable marker gene such as the cycloheximide-resistance L41 gene to terminate its function, and then used for transformation. The cycloheximide-resistant transformant thus obtained has two URA3 genes on the chromosome, and one of the two genes has been disrupted. Furthermore, a strain in which both of the URA3 genes have been disrupted is obtained by transforming the strain, in which one of the URA3 genes has been disrupted, with the URA3 gene fragment split with the other selectable marker gene such as a G418-resistance gene. The ura3 variant is known to become resistant to 5-fluoroorotic acid (5-FOA) which is a toxic analogue of an intermediate in uracil biosynthetic pathway. It is thus possible to obtain (as a 5-FOA resistant strain) the ura3 mutant (which has the URA3 genes both of which have lost the function) by the gene substitution of the strain in which one of the two URA3 genes has been disrupted. The ura3 mutant makes it possible to obtain a transformant with the URA3 gene as a selectable marker gene which is not a drug-resistance gene marker. Furthermore, the auxotrophiic mutant thus obtained has an advantage that it is scarcely influenced by the secondary mutation which may be caused in the other gene loci by the chemical mutation method.

L41 Gene

According to the present invention, the ribosomal protein L41 of Candida utilis, a gene encoding it, its promoter and terminator sequences are provided.

The protein L41 of Candida utilis according to the present invention has an amino acid sequence described in FIG. 14 (SEQ ID NO: 6). Thus, the L41 gene according to the present invention encodes the amino acid sequence described in FIG. 14. Moreover, a specific DNA sequence comprising this gene, its promoter and terminator sequences is shown in FIG. 13 (SEQ ID NO: 5).

In addition, according to the present invention, a cycloheximide-resistance L41 protein encoding mutant L41 gene in which the 56th amino acid residue has been converted from proline to glutamine is provided. The cycloheximide-resistance L41 gene can be used as described above not only as a selectable marker gene for the transformation of Candida utilis, but also as a selectable marker gene for the transformation of the other yeasts such as those of Saccharomyces genus. Furthermore, it is needless to say that the promoter and terminator sequences of the gene can be also used in the expression of heterologous genes.

PGK Gene

According to the present invention, the promoter and terminator sequences of the PGK gene is provided.

Specific examples of the promoter sequence include nucleotides 946–1346 of the DNA sequence shown in FIG. 3 (SEQ ID NO: 2) and its partial sequences retaining the promoter activity.

Specific examples of the terminator sequence preferably include the DNA sequence shown in FIG. 2 (SEQ ID NO: 1) and its partial sequences retaining the terminator activity.

An expression vector which may be used in Candida utilis can be obtained by inserting the promoter and terminator sequences into an appropriate plasmid vector. Examples of the plasmid vector include well-known E. coli plasmids such as pBluescript and pUC19, and a yeast-E. coli shuttle plasmid comprising a selectable marker gene such as the cycloheximide-resistance L41 gene and, if necessary, a DNA sequence homologous to a chromosomal target gene. It would be anticipated for a person skilled in the art that these sequences can be used as a promoter or terminator in the other host cells, particularly a yeast of the genus Saccharomyces.

The PGK gene is a gene encoding the enzyme in the glycolytic pathway and is expressed in a large amount together with the other genes encoding the enzymes of the glycolytic pathway in Candida utilis. Thus, it is expected to have a strong promoter. It is revealed in examples described below that the promoter can be advantageously used in the expression of a heterologous gene such as the glucoamylase gene, the aminoglycoside phosphotransferase gene or the β-galactosidase gene with use of the expression vectors prepared.

In addition, it would be obvious for a person skilled in the art that if the expression amount of a gene linked to the PGK gene promoter and terminator sequences according to the present invention is not decreased, the expression vector can be miniaturized by defecting a part of these sequences.

GAP Gene

According to the present invention, the promoter and terminator sequences of the GAP gene are provided.

Specific examples of the promoter sequence include preferably the DNA sequence shown in FIG. 30 (SEQ ID NO: 7) and its partial sequences thereof retaining the promoter activity.

Specific examples of the terminator sequence include preferably the DNA sequence shown in FIG. 31 (SEQ ID NO: 8) and its partial sequences thereof retaining the terminator activity.

An expression vector which can be used in Candida utilis can be obtained by inserting the promoter and terminator sequences to an appropriate plasmid vector. Examples of the plasmid vector include well-known E. coli plasmids such as pBluescript and pUC19, and a yeast-E. coli shuttle plasmid comprising a selectable marker gene such as a cycloheximide-resistance L41 gene and, if necessary, a DNA sequence homologous to a chromosomal target gene can be used. It would be anticipated for a person skilled in the art that these sequences can be used as a promoter or terminator in the other host cells, particularly a yeast of Saccharomyces genus.

The GAP gene is a gene encoding the enzyme in the glycolytic pathway and is expressed in a large amount together with the other genes encoding the enzymes of the glycolytic pathway in *Candida utilis*. Thus, it is expected to have a strong promoter. It is revealed in examples described below that the promoter can be advantageously used in the expression of a heterologous gene such as the aminoglycoside phosphotransferase gene with the expression vector prepared.

In addition, it would be obvious for a person skilled in the art that if the expression amount of a gene linked to the GAP gene promoter and terminator sequences according to the present invention is not decreased, the expression vector can be miniaturized by defecting a part of these sequences.

PMA Gene

According to the present invention, the promoter and terminator sequences of the PMA gene are provided.

Specific examples of the promoter sequence include preferably the DNA sequence shown in FIG. 34 (SEQ ID NO: 9) and partial sequences thereof retaining the promoter activity.

Specific examples of the terminator sequence include preferably the DNA sequence shown in FIG. 35 (SEQ ID NO: 10) and partial sequences thereof retaining the terminator activity.

An expression vector which can be used in *Candida utilis* can be obtained by inserting the promoter and terminator sequences to an appropriate plasmid vector. Examples of the plasmid vector include well-known *E. coli* plasmids such as pBluescript and pUC19, or a yeast-*E. coli* shuttle plasmid comprising a selectable marker gene such as a cycloheximide-resistance L41 gene and, if necessary, a DNA sequence homologous to a chromosomal target gene can be used. It would be anticipated for a person skilled in the art that these sequences can be used as a promoter or terminator in the other host cells, particularly a yeast of Saccharomyces genus.

The GAP gene is a gene encoding the plasma membrane enzyme, it is known in a Saccharomyces yeast to be a primary protein comprising about 10% of plasma membrane proteins. It is thus anticipated for the PMA gene to have a strong promoter. It is revealed in examples described below that the promoter can be advantageously used in the expression of a heterologous gene such as an aminoglycoside phosphotransferase gene with use of an expression vector prepared.

In addition, it would be obvious for a person skilled in the art that if the expression amount of a gene linked to the PMA gene promoter and terminator sequences according to the present invention is not decreased, the expression vector can be miniaturized by defecting a part of these sequences.

DNA Sequences having Promoter Activities

According to the present invention, DNA sequences having promoter activities are provided. The DNA sequences are isolated with use of a vector comprising an autonomously replicable DNA sequence and a drug-resistance marker gene having no transcriptional promoter sequence. Specific examples of the DNA sequence having the promoter activity include preferably a DNA sequence shown in FIG. 48 (SEQ ID NO: 13) and a partial sequence thereof retaining the promoter activity. In addition, as described in examples below, eight DNA sequences were obtained in addition to the DNA sequence of FIG. 48 which has the promoter activity. DNA sequences having promoter activities can be also isolated by replacing the drug-resistance gene having no transcriptional promoter sequence with the other genes such as a hygromycin B-resistance gene. In addition, it is also possible to obtain a promoter in which transcriptional activity is induced under a specific condition by changing the selection conditions such as sugars contained in plate for selecting transformants or the other medium composition. These would be easily understood by a person skilled in the art by referring the disclosure of the present specification.

An expression vector which can be used in *Candida utilis* can be obtained by inserting the promoter and terminator sequences to an appropriate plasmid vector. Examples of the plasmid vector include well-known *E. coli* plasmids such as pBluescript and pUC19, and a yeast-*E. coli* shuttle plasmid comprising a selectable marker gene such as the cycloheximide-resistance L41 gene and, if necessary, a DNA sequence homologous to a chromosomal target gene can be used. It would be anticipated for a person skilled in the art that these sequences can be used as a promoter or terminator in the other host cells, particularly a yeast of Saccharomyces genus.

It is proved in examples described below that the promoter can be advantageously used in the expression of a heterologous gene such as an aminoglycoside phosphotransferase gene with use of an expression vector prepared.

In addition, it would be obvious for a person skilled in the art that if the expression amount of a gene linked to the promoter sequence according to the present invention is not decreased, the expression vector can be miniaturized by defecting a part of the sequence.

rRNA Gene

According to the present invention, an about 13.5 kb DNA fragment comprising the rRNA genes of *Candida utilis* and a DNA sequence comprising the repetition of the fragment are provided.

The about 13.5 kb fragment is represented by the restriction enzyme map shown in FIG. 6(*b*). The locations of 18S, 5.8S and 25S rRNA genes in the DNA sequence are shown in FIG. 6(*b*).

The multiple-copies integration of a DNA fragment into a chromosome is efficiently accomplished by using a partial region of the rRNA genes as a target sequence. Plasmids were constructed with four fragments which have been obtained by dividing the about 13.5 kb DNA fragment into four and used for transformation. It was interestingly observed that the transformation frequencies thus obtained were different depending on the regions used as the target sequence for integration. While transformation frequency was low in the plasmid pCLRE5 comprising a 2.4 kb EcoRI fragment which comprises the 18S rRNA gene, transformants were obtained in high frequencies in the plasmid pCLRE4 comprising a 3.5 kb EcoRI fragment which comprises a part of the 3' side of 18S rRNA gene, the 5.85 rRNA gene and a part of the 5' side of 25S rRNA gene, the plasmid pCLRE6 comprising a 3 kb EcoRI fragment which comprises a 25S rRNA gene, and the plasmid pCLRE7 comprising a 4.7 kb EcoRI fragment which comprises a part of the 5' side of 18S rRNA gene.

URA3 Gene

According to the present invention, the URA3 gene of *Candida utilis* which is complementary to the ura3 mutation of a *Saccharomyces cerevisiae* yeast is provided. The gene can be used as described above as an integration target of a DNA fragment and also used in the creation of a ura3 mutant by disrupting the chromosomal URA3 gene. The ura3 mutant as a host makes it possible to obtain a transformant with the URA3 gene as a selectable marker gene which is not a drug-resistance gene marker. In addition, it is obvious that the promoter and terminator sequences of the gene can be also used for the expression of a heterologous gene.

The URA3 gene encodes the amino acid sequence shown in FIGS. 10 and 11 (SEQ ID NO: 4). The URA3 gene includes a gene comprising the DNA sequence shown in FIG. 9 (SEQ ID NO: 3) or having partial sequences thereof which retain the function complementing the ura3 mutation of the *Saccharomyces cerevisiae* yeast.

Autonomously Replicating DNA Sequence (ARS)

According to the present invention, autonomously replicating DNA sequences which can retain the vector containing the DNA sequence as episomal plasmids in *Candida utilis* and enhance the transformation frequency of the host are provided. The DNA fragment may be derived from any organisms, preferably from *Candida utilis*. Specific examples of ARS include preferably the DNA sequences shown in FIGS. 41 and 42 (SEQ ID NO: 11) and in FIGS. 43 and 44 (SEQ ID NO: 12), and autonomously replicable partial sequences thereof. Apparently from examples below, it is also possible to transform the *Candida utilis* yeast with the plasmids having shortened DNA fragments notwithstanding the frequency being decreased.

A vector which can be present as a plasmid in *Candida utilis* is provided by using ARS and an appropriate selectable marker gene. Furthermore, DNA sequences having promoter activities and DNA sequences having the other functions are isolated by using the vector. It is also possible to create a transformed yeast retaining only a DNA fragment which contains no selectable marker gene but a heterologous gene on a chromosome by using a plasmid containing ARS and an appropriate marker gene and a plasmid comprising a sequence homologous to the *Candida utilis* chromosomal DNA (homologous DNA sequence) and having no selectable marker gene for selecting transformants.

EXAMPLES

The present invention is further specifically described with reference to the following examples, but it is not limited to these examples.

In this disclosure, restriction enzyme sites in the restriction enzyme maps of genes are represented by the following. Aa; AatII, Af; AflIII, Al; AflIII, Ap; ApaI, B; BamHI, Bg; BglII,C; ClaI, E; EcoRI, RV; EcoRV, H; HindIII, Hp; HpaI, K; KpnI, P; PstI, Pv; PvuII, S; SalI, Se; SpeI, Sm; SmaI, Sc; SacI, ScII; SacII, Sp; SphI, X; XbaI, and Xh; XhoI.

The methods used in the following examples are as follows:

1) Deletion mutation treatment with ExoIII nuclease and mung bean nuclease, and determination of DNA sequence After a plasmid (10 μg) was digested with an appropriate restriction enzyme, it was extracted with phenol/chloroform and precipitated with ethanol to recover DNA. DNA was dissolved in 100 μl of an ExoIII buffer solution (50 mM Tris-HCl, pH 8.0, 100 mM NaCl, 5 mM $MgCl_2$, 10 mM 2-mercaptoethanol), 180 units of ExoIII nuclease, and the mixture was incubated at 37° C. A 10 μl portion of the mixture was taken out at every one minute, and two portions were combined and transferred to an ice-cooled tube in which 20 μl of an MB buffer (40 mM Na acetate, 100 mM NaCl, 2 mM $ZnCl_2$, 10% glycerol, pH 4.5) was placed. After five tubes thus obtained were incubated at 65° C. for 10 minutes to inactivate the enzyme, five units of mung bean nuclease was added, and the mixture was reacted at 37° C. for 30 minutes. After the reaction, five DNA fragments having different degrees of deletion was collected by agarose gel electrophoresis. The DNA fragments thus collected were treated with Klenow enzyme to form a blunt end and ligated at 16° C. overnight, and were used for the transformation of *E. coli*.

For insertion fragments of the plasmids thus obtained, the sequencing reaction was carried out with a fluorescent primer cycle sequence kit (Applied Biosystems, K.K.), and the DNA sequence was determined with an automatic DNA sequencer.

2) Hybridization

After agarose gel electrophoresis, DNA was alkali transferred to a Hibond N+filter (Amersham) according to the protocol provided by the manufacturer to prepare a filter for Southern hybridization.

The filter on which DNA was fixed was subjected to prehybridization in a hybridization solution (6×SSC, 5×Denhardt's Solution, 0.2% SDS, 20 μg/ml salmon sperm DNA) at 65° C. for 2 hours. A probe DNA labelled with Megaprime DNA labelling systems and [$\alpha$-$^{32}$P]dCTP (110 TBq/mmol) was added to the hybridization solution, and hybridization was performed at 65° C. for 16 hours. After hybridization, the filter was washed in 1×SSC containing 0.1% SDS at 65° C. for 2 hours and then subjected to autoradiography to detect signals.

3) Composition of medium

The composition of a YPD medium for culturing yeast contains 1% yeast extract, 2% bactopeptone and 2% glucose. Agar was added in an amount of 2% to the medium in the case of a plate form. The composition of a SD medium contains 0.67% yeast nitrogen base without amino acids and 2% glucose. Amino acids were added to the medium depending on the nutritional requirements of the yeast used. In the case of a plate form, agar was added in an amount of 2% to the medium.

4) Treatment with enzyme

Treatments of DNA with enzymes such as a restriction enzyme reaction, Klenow enzyme and T4 DNA ligase were conducted under the conditions recommended by the manufacturers or according to the methods described in Molecular Cloning, 2nd edition, Sambrook et al., Cold Spring Harbor Laboratory Press (1989).

Example 1

Preparation of *Candida utilis* chromosomal DNA

The extraction of *Candida utilis* chromosomal DNA was carried out by the following procedure. ATCC 9950 strain of *Candida utilis* was inoculated in 30 ml of YPD medium and cultured at 30° C. early stationary phase. The cells were collected by centrifugation, washed with sterilized water, and collected again by centrifugation. After the cells were suspended in 3 ml of Zymolyase buffer (0.9M sorbitol, 0.1M EDTA, 50 mM DTT, pH 7.5), 200 μl of 0.9M sorbitol containing 25 mg/ml Zymolyase 100T was added, and the mixture was incubated at 37° C. under shaking. After the formation of protoplast was confirmed by microscopic observation, the protoplasts were collected by centrifugation. After 3 ml of lysis buffer (50 mM Tris-HCl, 50 mM EDTA, pH 8.0) was added and the protoplasts were suspended gently and sufficiently in the buffer, 0.3 ml of 10% SDS was added, and the mixture was incubated at 65° C. overnight. Then, 1 ml of a 5M potassium acetate solution was added, and the mixture was left standing on ice for 1 hour. Precipitates were then removed by centrifugation, 4 ml of cold ethanol was added, and the mixture was centrifuged to precipitate DNA. The precipitate was washed with 50% ethanol, dried, dissolved in 3 ml of an RNase A buffer (10 mM Tris-HCl, 1 mM EDTA, 50 µg/ml RNase A, pH 7.5), and incubated at 37° C. for 30 minutes. Finally, 3 ml of 2-propanol was added and the mixture was centrifuged to remove the supernatant. Precipitates thus obtained were washed with 50% 2-propanol and dried. The precipitate was dissolved in 0.5 ml of a TE buffer and used as a *Candida utilis* chromosomal DNA sample.

Example 2
Cloning of the phosphoglycerate kinase (PGK) gene

After the partial digestion of the *Candida utilis* chromosomal DNA with a restriction enzyme Sau3AI, the digested mixture was layered on a 10–50% sucrose density gradient containing 0.8M NaCl, 20 mM Tris-HCl, 10 mM EDTA (pH 8.0), and centrifuged under 120,000×g for 14 hours to fractionate the DNA fragments. Among these fragments, 10–20 kb chromosomal DNA fragment was ligated overnight with dephosphorylated λ-phage vector DASHTMII (Stratagene Cloning Systems) which had been digested with BamHI, and then subjected to in vitro packaging to construct a *Candida utilis* genomic DNA library.

The PGK gene of *Candida utilis* was cloned by the hybridization using a known PGK gene of the other organism as a probe. Specifically, filters on which about 20,000 plaques of the phage DNA of the above described DNA library were adsorbed was prepared according to the method described in Molecular Cloning, 2nd edition, Sambrook et al., Cold Spring Harbor Laboratory Press (1989). Then, the DNA fragment containing the PGK gene of *Saccharomyces cerevisiae* was cut off as a 2 kb ClaI fragment from plasmid pST2 which retains the PGK gene (Yamano et al., Journal of Biotechnology, 32, 165–171 (1994)). The fragment was then labelled with $^{32}P$ and used as a probe for hybridization. As a result, four positive plaques were cloned. The phage DNAs prepared from each of these plaques were digested with a variety of restriction enzymes and subjected to Southern blot analysis using the same probe as the above. As a result, a 2.6 kb EcoRI fragment and a 2.5 kb SalI fragment hybridized with the probe were isolated.

Example 3
Determination of the DNA sequence of a fragment containing the PGK gene, and characterization of the structural gene and the regulatory regions The 2.6 kb EcoRI fragment thus isolated was inserted into the EcoRI site of a plasmid vector Bluescript IISK+ to construct plasmids pPGKE1 and pPGKE2 of which the inserted fragments are opposite in their directions to the vector. The 2.6 kb SalI fragment was also inserted into the SalI site of the vector Bluescript IISK+ to prepare plasmids pPGKS1 and pPGKS2 of which the inserted fragments are opposite in their directions to the vector (FIG. 1).

From the plasmids pPGKE1 and pPGKE2, plasmids having various deletion mutations were obtained by preparing deletion mutants at restriction enzyme sites such as HindIII, KpnI or SalI sites or by preparing a deletion mutant with ExoIII nuclease and mung bean nuclease and the DNA sequence of a 2530 bp EcoRI fragment was determined.

The analysis of the region where the structural gene was expected revealed a 1248 bp open reading frame. The homology to the PGK gene of *Saccharomyces cerevisiae* was examined on the amino acid sequence deduced from the DNA sequence of the open reading frame. These sequences showed a homology of 86.8% to each other, so that the isolated gene was concluded to be the PGK gene of *Candida utilis*.

The EcoRI fragment contained 401 bp fragment of the upstream of the initiation codon ATG and 880 bp fragment of the downstream of the termination codon TAA as the regulatory regions of the gene expression. The DNA sequence of the 880 bp fragment between the nucleotide next to the termination codon TAA, and the EcoRI site which may contain a transcription terminator is shown in FIG. 2. Further, from the plasmids pPGKS1 and pPGKS2, plasmids having deletion mutations were obtained by preparing deletion mutants with ExoIII nuclease and mung bean nuclease in order to determine the DNA sequence between the HindIII site and the EcoRI site (FIG. 1). The sequence of the 1346 bp fragment between the HindIII site and the nucleotide immediately before the initiation codon ATG which may contain a transcription promoter is shown in FIG. 3.

Example 4
Construction of expression vectors with the PGK gene promoter and terminator In order to express a heterologous gene in *Candida utilis*, a gene expression machinery which functions in *Candida utilis*, that is, a transcription promoter and a terminator are required. Expression vector plasmids having a multicloning site was thus prepared between the PGK gene promoter and the terminator of *Candida utilis*.

Firstly, fragments containing a promoter or a terminator were prepared by Polymerase Chain Reaction (PCR).

As the promoter, a fragment from the SalI site located at the 2.3 kb upstream of the initiation codon to the nucleotide immediately before the initiation codon ATG was prepared using the plasmid PGKS1 as a template. The primers were synthesized with the following sequences in which a XbaI site was created just before the initiation codon at the 3'-end of the promoter fragment.

5'-GGTCGACATATCGTGGTAAGCGCCTT-
GTCA-3' (SEQ ID NO: 14)

5'-TTCTAGACTTTATCCGCCAGTATGTT-
AGTC-3' (SEQ ID NO: 15)

In addition, as the terminator, a fragment from the nucleotide after the termination codon to the EcoRI site at a 880 bp downstream was prepared using the plasmid PGKE1 as a template. The primers were synthesized with following sequences in which a KpnI site was created just after the termination codon at the 5'-end of the terminator fragment.

5'-GGGTACCTAACTGCAAGCTACTTTGTAATT-
AAC-3' (SEQ ID NO:16)

5'-GGAATTCAACATGAATGACACGACGAA-
GGT-3' (SEQ ID NO:17)

The PCR process was conducted 30 cycles with Pfu DNA polymerase (Stratagene Cloning Systems) and attached buffer.

The promoter and terminator fragments synthesized by the PCR process were digested with SalI and XbaI or with KpnI and EcoRI, respectively. The fragments were incorporated sequentially into the SalI—XbaI site and KpnI—EcoRI site in pUC19 to construct a plasmid pPGKPT1 (FIG. 4). After the EcoRI site at the 3'-end of the terminator of the plasmid was treated with Klenow enzyme to form a blunt end and ligated with NotI linkers (5'-AGCGGCCGCT-3': SEQ ID NO: 18), the 0.9 kb PstI—NotI fragment was prepared by digesting the plasmid with PstI. The fragment and the 1.2 kb HindIII—PstI fragment cut out from the plasmid pPGKS1 was inserted between the HindIII site and the NotI site of pBluescript SK− to construct a plasmid pPGKPT2. Furthermore, pPGKPT2 was digested with BglII, treated with Klenow enzyme and recyclized to remove the BglII site in the terminator fragment and to construct a plasmid pPGKPT3. After the HindIII site of pPGKPT3 was then treated with Klenow enzyme to form blunt ends, the fragment was ligated with NotI linkers (5'-AGCGGCCGCT-3': SEQ ID NO: 18) to construct a plasmid pPGKPT4. The plasmid pPGKPT4 was partially digested with KpnI, and the KpnI at the upstream of the promoter was deleted to construct a plasmid pPGKPT5 (FIG. 4).

Example 5
Isolation of the rDNA

A 400 ng portion of 5–10 kb Sau3AI partially digested DNA fragments of Candida utilis ATCC 9950 genomic DNA obtained by the sucrose density gradient centrifugation described in Example 2, and 200 ng of vector plasmid pBR322 digested with BamHI and dephosphorylated were ligated overnight with T4 DNA ligase. E. coli DH5 was transformed with this DNA solution to construct a Candida utilis genomic DNA library.

Filters were prepared for about 10,000 colonies according to the method described in Molecular Cloning, 2nd edition, Sambrook et al., p. 12, 21–23, Cold Spring Harbor Laboratory (1989), and screened with the 1.8 kb $^{32}$P-labelled HindIII—EcoRI fragment containing S. cerevisiae 18S rRNA gene as a probe. The rDNA fragment used as the probe was prepared from a plasmid obtained from a genomic DNA library of Saccharomyces cerevisiae S288C [α, suc2, mal, gal2, CUP1] with a $^{32}$P-labelled oligomer corresponding to the fragment of nucleotides 4–42 at 5'-terminal of the 5.8S rRNA gene as a probe (Sone et al., Japanese Patent Publication No. 14865/1994).

Over 200 positive clones were obtained. Restriction enzyme maps of plasmids from seven clones, pCR1, pCR4, pCR5, pCR6, pCR7, pCR8 and pCR9 were constructed and aligned for comparison. The restriction enzyme maps at the both terminals were accorded (FIG. 5). It has been found from this fact that the region containing the rRNA gene of Candida utilis has an about 13 kb repetitive structure.

Figure 6A:
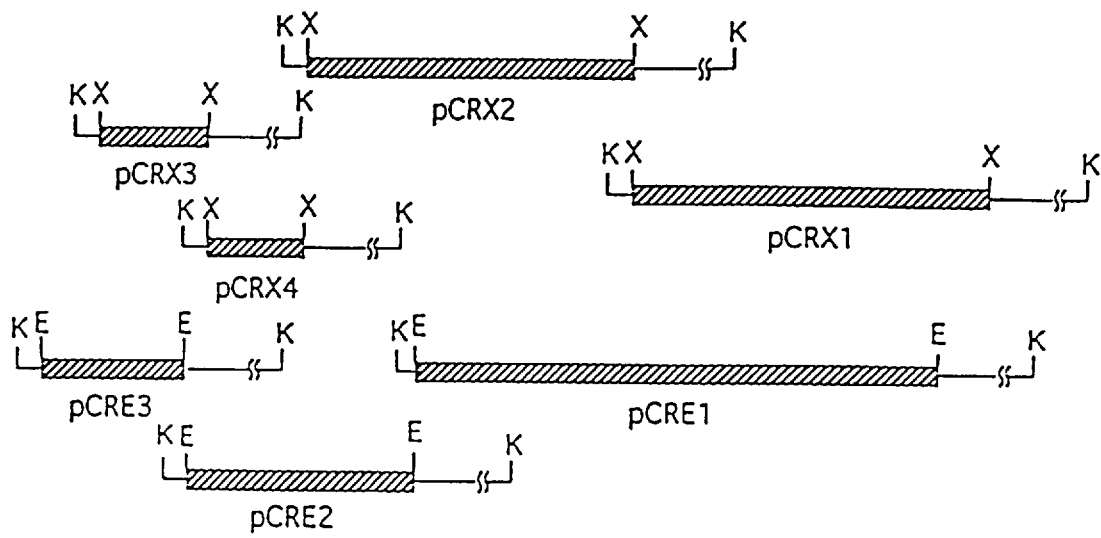
FIGS. 6A and 6B illustrate the structure of the ribosomal DNA, the strategy for determining the DNA sequencing, and the structure of subcloned plasmids, where FIG. 6(*a*) illustrates the structures of the plasmids pCRE1, pCRE2, pCRE3, pCRX1, pCRX2, pCRX3 and pCRX4, and FIG. 6(*b*) illustrates the restriction enzyme map of about 13;5 kb DNA fragment containing the ribosomal DNA of *Candida utilis;*
Figure 6B:
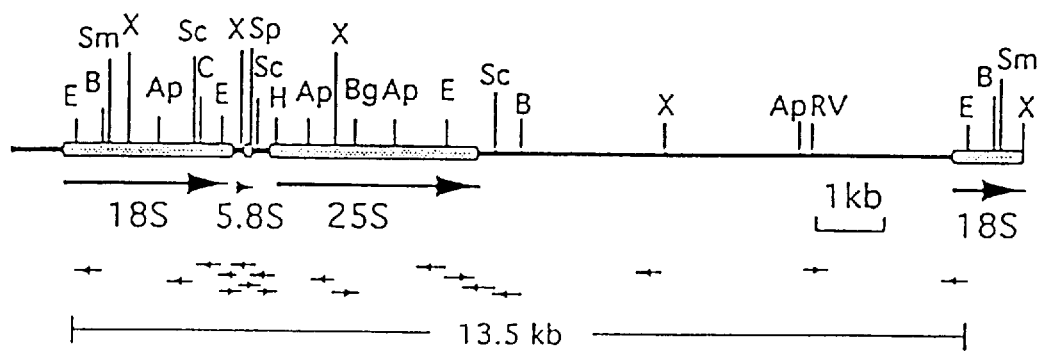

From these plasmids, fragments cut out by digestion with EcoRI or XbaI were subcloned into pBluescript SK− to construct plasmids pCRE1, pCRE2, pCRE3, pCRX1, pCRX2, pCRX3 and pCRX4 (FIG. 6(a)). Furthermore, these plasmids were digested with a variety of restriction enzymes and recyclized to construct a variety of deletion plasmids. DNA sequences were determined on the insertion fragments of these plasmids and the regions where the DNA sequence was determined are shown by arrows in the figure. The analysis of the DNA sequences revealed the presence of the regions which have high homology with the 18S, 5.8S and 25S rRNA genes. Thus, the location and transcriptional direction of the three rRNA genes were determined (FIG. 6(b)).

Example 6
Cloning of the orotidine 5'-phosphate decarboxylase gene (URA3 gene)

A 100 ng portion of 5–10 kb Sau3AI partially digested DNA fragments of Candida utilis ATCC 9950 genomic DNA obtained by the sucrose density gradient centrifugation described in Example 2, and 100 ng of vector plasmid YEp13 (Methods in Enzymol., 194, 195–230, 1991) digested with BamHI and dephosphorylated were ligated overnight with T4 DNA ligase. E. coli DH5 was transformed with this DNA solution to construct a genomic DNA library. After the plasmid mixture was extracted from the transformants, Saccharomyces cerevisiae YPH 500 (αhis3, trp1, leu2, ade2, lys2, ura3) (Stratagene Cloning Systems) which is a ura3-strain was transformed with the plasmid DNA mixture and the transformants which did not require uracil for growth were selected on a minimal medium. Transformation of S. cerevisiae was conducted according to the lithium method described in Methods in Yeast Genetics—A Laboratory Course Manual—Rose M. D. et al., p. 122–123, Cold Spring Harbor Laboratory Press, NY (1990).

Five Ura+ strains were obtained from 10 μg of DNA by this procedure. Plasmid DNA was prepared from each of these transformants according to the method described in Methods in Yeast Genetics—A Laboratory Course Manual—Rose M. D. et al., p. 130, Cold Spring Harbor Laboratory Press, NY (1990). E. coli was transformed with the DNA, and a plasmid DNA was prepared. Restriction enzyme maps were constructed on the plasmids pCURA3-3 containing a 6.1 kb insert and pCURA3-5 containing a 8.1 kb insert at the BamHI site of YEp13, respectively.

Figure 7:
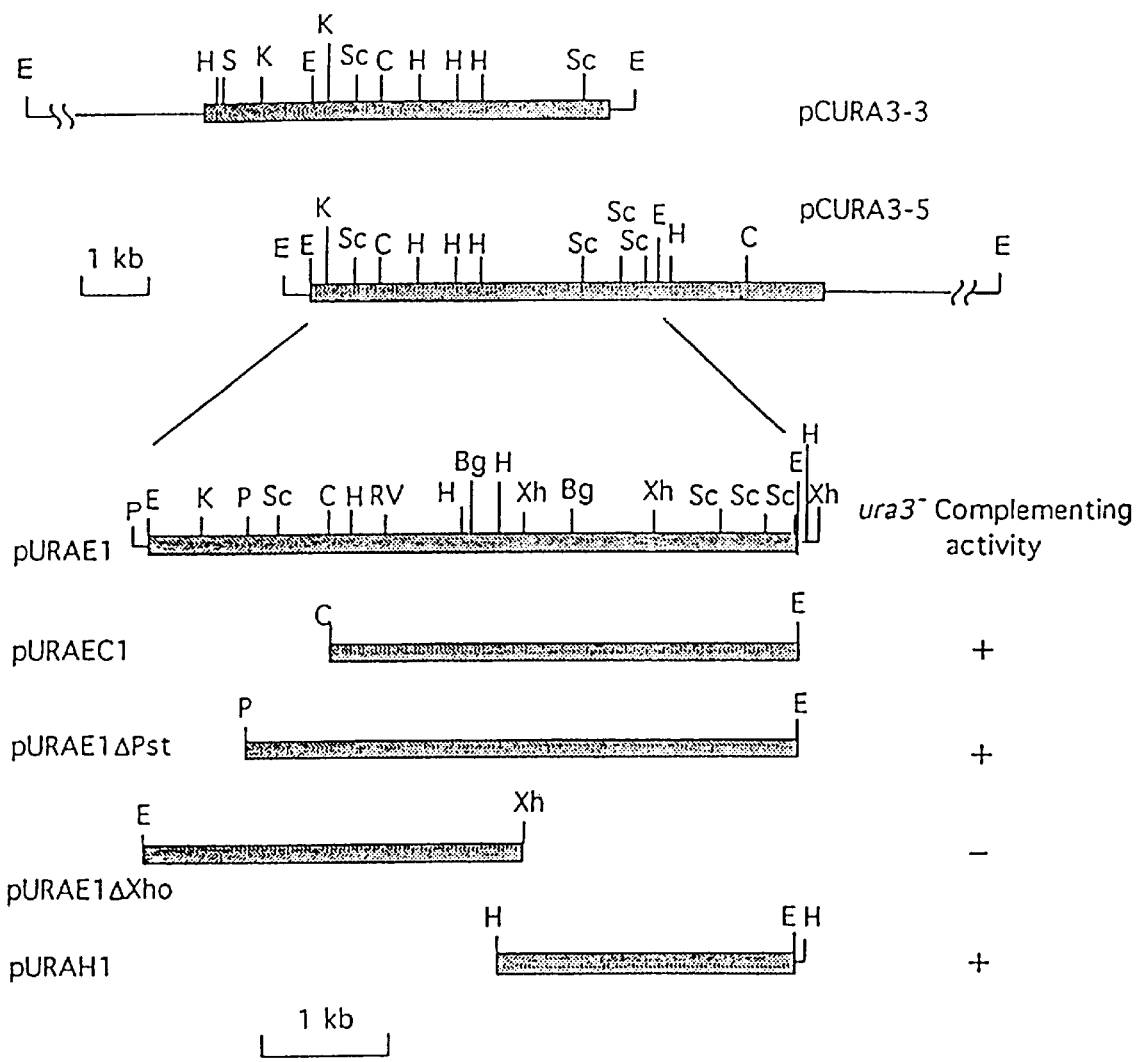
FIG. 7 illustrates the restriction enzyme maps of plasmids containing URA3 gene, and the complementation ability for the *Saccharomyces cerevisiae* ura3-mutation of these plasmids.

Example 7
Characterization of URA3 gene region and determination of DNA sequence In order to characterize the URA3 gene region, a 5 kb EcoRI fragment containing a region common to the plasmids pCURA3-3 and pCURA3-5 was cut out from a plasmid pCURA3-5 and ligated to the EcoRI site of a plasmid pRS314 (Stratagene Cloning Systems) to prepare a plasmid pURAE1 (FIG. 7). The YPH 500 strain was transformed with the plasmid by the lithium method. As a result, URA+ transformants were obtained in high frequency. This indicates that URA3 gene is present in the 5 kb EcoRI fragment, and one copy of the gene can complement the ura3-mutation of Saccharomyces cerevisiae.

Further, the plasmid pURAE1 was digested with XhoI or PstI and recyclized by the T4 ligase reaction to give plasmids pURAE1ΔXho and pURAE1ΔPst.

Furthermore, the 3.5 kb EcoRI-ClaI fragment and the 2.3 kb HindIII fragment cut out from the plasmid pURAE1 were inserted between EcoRI and ClaI sites, or at the HindIII site of the pRS314, respectively, to prepare plasmids pURAEC1 and pURAH1 (FIG. 7).

The YPH500 strain was transformed with five plasmids described above by the lithium method to examine the complementarity of ura3− mutation and thus to examine whether these fragments contain the URA3 gene or not. The result is shown in FIG. 7. The results showed that the URA3 gene is located in 2.3 kb region between the EcoRI and HindIII.

Further, the 2.3 kb HindIII fragment containing the URA3 gene was ligated to the HindIII site of the plasmid pBluescrip SK− to prepare a plasmid pURAH2. By the deletion mutation with ExoIII nuclease and mung bean nuclease from both ends of the inserted fragment, plasmids having deletion mutation were prepared, and the DNA sequence was determined. The restriction enzyme map which has been clarified by the DNA sequence and the sequence strategy are shown in FIG. 8. The 2330 bp DNA sequence thus obtained is shown in FIG. 9, and the deduced amino acid sequence of the polypeptide consisting of 267 amino acid residues is shown in FIGS. 10 and 11.

The amino acid sequence of the polypeptide was compared with that of the URA3 protein of the other yeasts, showing high homologies, for example 73.4% to *Saccharomyces cerevisiae*, 76.3% to *Kluyveromyces lactis*, and 75.1% to *Candida albicans*.

Example 8
Cloning of the L41 gene and determination of the DNA sequence of a DNA fragment containing the L41 gene Filters were prepared for about 30,000 colonies of the library prepared in Example 5 according to the method described in Molecular Cloning, 2nd edition, Sambrook et al., p. 12, 21–23, Cold Spring Harbor Laboratory (1989), and screened with a 1.1 kb $^{32}$P-labelled XbaI—Sau3AI fragment containing *Candida maltosa* L41 gene, RIM-C, as a probe (Kawai et al., J. Bacteriol., 174, 254–262 (1992)).

Five positive clones were thus obtained. Restriction enzyme maps of the three clones, pCL41-1, pCL41-2 and pCL41-5 were constructed and compared with each other. These clones have a 4 kb EcoRI fragment in common (FIG. 12). Southern hybridization analysis of these plasmid DNA has revealed that a region which shows homology to the L41 gene of *Candida maltosa* is present in the 1.4 kb ClaI-PstI fragment within the 4 kb EcoRI fragment.

The 4 kb EcoRI fragment was inserted into the EcoRI site of pBluescript SK⁻ to prepare plasmids pCLE1 and pCLE2 in which the fragment is inserted to an opposite direction with each other. From these two plasmids, a variety of plasmids having deletion mutations were obtained by preparing deletion mutants with HindIII, XhoI or ClaI having a site within the EcoRI fragment or by preparing deletion mutants with ExoIII nuclease and mung bean nuclease in order to determine the 2086 bp DNA sequence from the BamHI site to the SacI site (FIG. 13).

Southern analysis revealed that a 318 bp open reading frame interrupted by a 367 bp intron is present in the region in which the presence of an L41 structural gene is deduced (FIGS. 12 and 14). At the 5' and 3' terminals and in the neighborhood of the 31 terminal in the region which was deduced to be an intron, sequence GTATGT--TACTAAC--AG which is common to intron was observed. Further, the sequences were located at immediately after the initiation codon as well as six L41 genes of the other yeasts described by Kawai et al., J. Bacteriol., 174, 254–262 (1992); Pozo et al., Eur. J. Biochem., 213, 849–857 (1993)). The deduced amino acid sequence of the *Candida utilis* L41 polypeptide was compared with those of the L41 proteins of some other yeasts, showing high homologies, for example 93.4% to *Saccharomyces cerevisiae* L41, 89.6% to *Candida tropicalis* L41, and 85.8% to *Candida maltosa* L41.

Example 9
Preparation of cycloheximide-resistance L41 gene by site-specific mutation The amino acid at 56 position of the L41 protein of a cycloheximide-resistant yeast is glutamine, while the amino acid at the corresponding position in the L41 protein of a cycloheximide-sensitive yeast is proline. It has been reported that the sensitivity to cycloheximide of the yeast is determined by this amino acid residue of the L41 protein (Kawai et al., J. Bacteriol., 174, 254–262 (1992)). In addition, the amino acid at 56 of the L41 protein of a cycloheximide-sensitive *Candida utilis* was proline like that of a cycloheximide-sensitive *Saccharomyces cerevisiae*. The codon encoding the proline at the 56 position of the L41 gene was changed into a glutamine codon by site-specific mutagenesis in order to convert the L41 protein encoded by the gene into a cycloheximide-resistant protein, which as used as a selectable marker of transformation.

Figure 15:
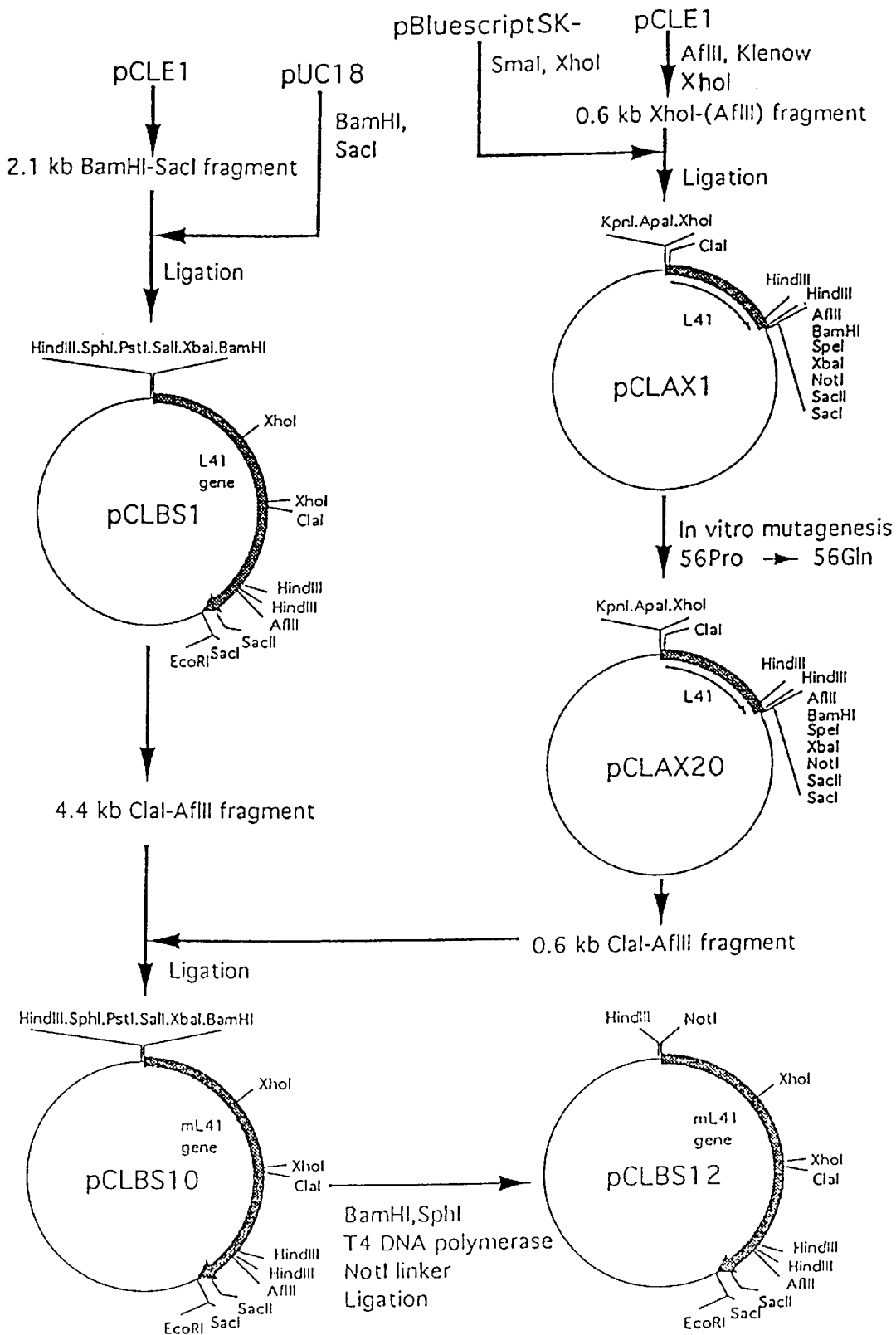
FIG. 15 illustrates the construction of plasmids pLCBS10 and pCLBS12.
Figure 16:
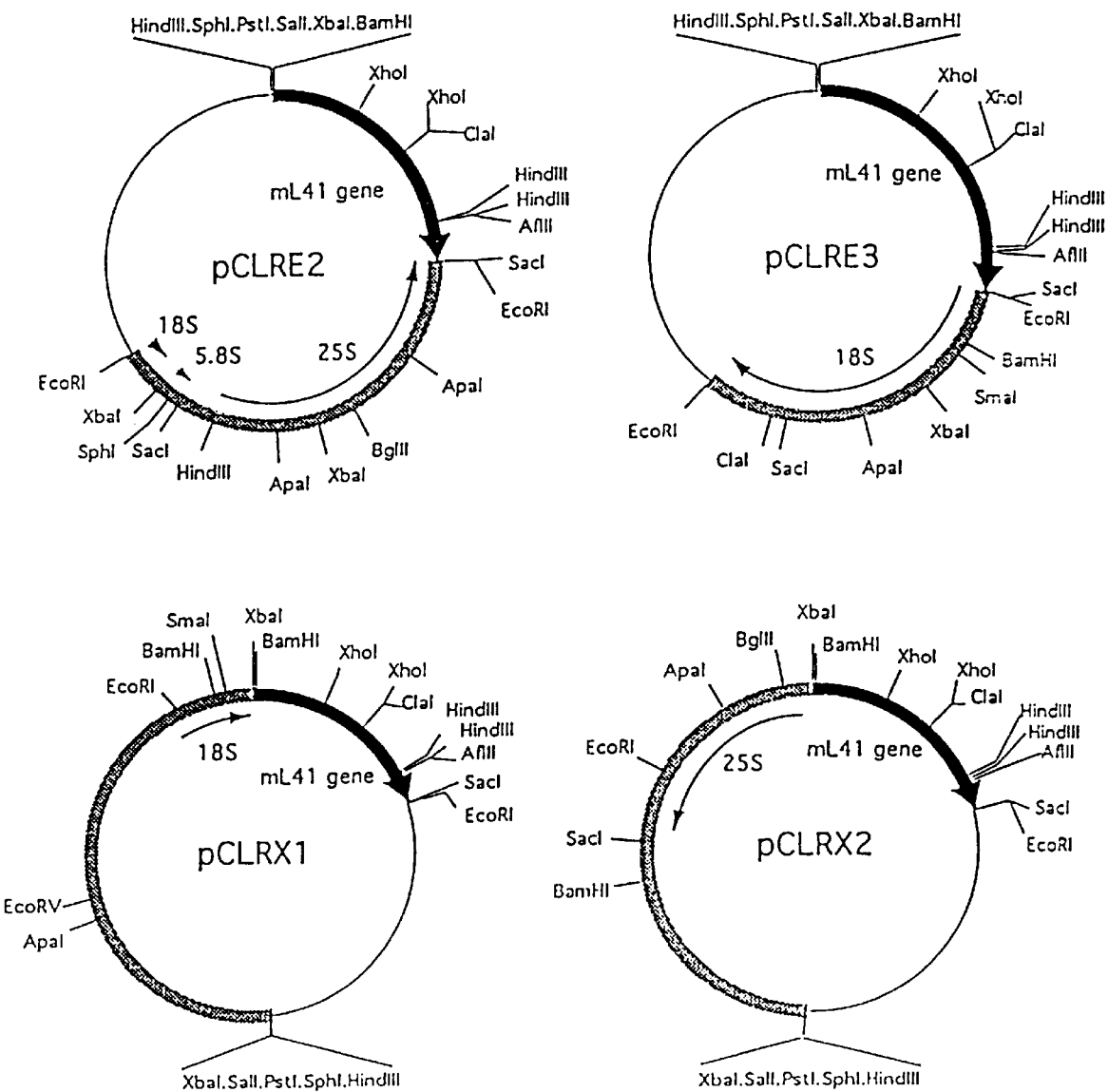
FIG. 16 illustrates the construction of plasmids pCLRE2, pCLRE3, pCLRX1 and pCLRX2.

Firstly, a 2.1 kb BamHI-SacI fragment obtained from the plasmid pCLE1 was inserted between the BamHI and SacI sites of pUC18 to prepare a plasmid pCLBS1 (FIG. 15).

Further, 0.6 kb fragment obtained by digesting the plasmid pCLE1 with AflII, treating with Klenow enzyme to form blunt ends and further digesting with XhoI was inserted between the SmaI and XhoI sites of pBluescript SK⁻ to prepare pCLAX1. In this plasmid, the AflII site is regenerated by the ligation of the blunt AflII end of the 0.6 kb fragment and the SmaI end of a vector. A single stranded DNA was prepared from pCLXA1 with a helper phage, and a mutant plasmid was prepared with a synthetic oligonucleotide 5'-TTG TGG AAA ACT TGC TTG GTT TGA-3' (SEQ ID NO:38) and a Sculptor In Vitro Mutagenesis Kit (Amersham). DNA sequence of the 0.6 kb insertion fragment on the candidate plasmid thus obtained was determined, and a plasmid pCLAX20 in which no mutation in the DNA sequence was found except that the 56th proline codon CCA had been mutated into a glutamine codon CAA was obtained.

A 0.6 kb insertion fragment was cut out as a ClaI-AflII fragment from pCLAX20 and ligated with a 4.4 kb fragment obtained by digesting the plasmid pCLBS1 with ClaI and AflII to construct a plasmid pCLBS10 containing a mutated L41 gene.

The plasmid pCLBS10 was digested with BamHI and SphI, treated with T4 DNA polymerase to form blunt ends, and NotI linkers (5'-AGCGGCCGCT-3', SEQ ID NO: 18) were inserted to prepare a plasmid pCLBS12 (FIG. 15).

It was examined whether the mutated L41 gene thus obtained confers yeast resistance to cycloheximide or not. A 2.1 kb BamHI-SacI fragment containing the mutated L41 gene which was obtained from the plasmid pCLBS10 was inserted between the BamHI and SacI sites of YEp13K a YEp vector (Sone et al., Appl. Environ. Microbiol., 54, 38–42 (1988)) to prepare a plasmid pYECL10. On the other hand, a 2.1 kb BamHI-SacI fragment containing the wild type L41 gene obtained from pCLBS1 was cloned into the YEp13K to prepare a plasmid pYECL1 as a control.

A Saccharomyces yeast strain YPH 500 was transformed with these plasmids according to the lithium acetate method described in Methods in Yeast Genetics—A Laboratory Course Manual—Rose M. D. et al., p. 122–123, Cold Spring Harbor Laboratory Press, NY (1990). Leucine non-requirement strains were selected as transformants. These transformants were grown on YPD plate containing cycloheximide. As a result, the strain retaining pYECL10 grew on the YPD plate containing cycloheximide. On the contrary, the strain retaining pYECL1 did not grow on the YDP plate containing cycloheximide. It was thus proved that the mutated L41 gene thus prepared conferred resistance to the cycloheximide-sensitive yeast.

Example 10
Construction of plasmids for transformation and determination of the conditions of transformation in *Candida utilis*

Firstly, transformation of *Candida utilis* ATCC 9950 strain was tried with plasmids containing the expression cassette of a G418-resistance gene (aminoglycoside phosphotransferase (APT) gene) which had been proved to function in *Saccharomyces cerevisiae*. The expression cassette was prepared by ligating a 1.1 kb G418-resistance gene which was cut out as a XhoI-PstI fragment from a plasmid pUC4K (Pharmacia) and converted into the one having blunt ends between the 1.0 kb promoter region of the glyceraldehyde-3-phosphate dehydrogenase gene and the 0.4 kb terminator region of the phosphoglycerate kinase gene described by Yamano et al., J. Biotechnol., 32, 165–171 (1994). Some plasmids were used, i.e., (1) a plasmid in which the above cassette was ligated to YEp13 K as a YEp vector; (2) A DNA library in which San3AI partially digested chromosomal DNA fragments (5–10 kb) of the *Candida utilis* ATCC 9950 strain described in Example 2 were inserted into the BamHI site of a plasmid pGPDAPH1 which was constructed by the above expression cassette was ligated to plasmid pBluescript SK⁻, and (3) eight plasmids of pGPDAPH1 containing ARS sequences which function in *Saccharomyces cerevisiae*. The plasmids in (3) were isolated from yeast colonies which were obtained by transformation of *Saccharomyces cerevisiae* YPH 500 strain with the library in (2). The transformation of *Candida utilis* ATCC 9950 strain was carried out with these plasmids or library DNA by the electric pulse method with various combinations of resistance and voltage or the lithium acetate method. However, no colonies exhibiting resistance to G418 were obtained.

As the next stage, four rDNA fragments cut out from the plasmids pCRE2, pCRE3, pCRX1 and pCRX2 described in Example 5 (FIG. 6) with EcoRI or XbaI were inserted into the EcoRI site or the XbaI site in the plasmid pCLBS10 described in Example 9 (FIG. 15) to construct plasmids pCLRE2, pCLRE3, pCLRX1 and pCLRX2.

Transformations of *Candida utilis* ATCC 9950 strain were carried out by the electric pulse method with various combinations of resistance and voltage and the lithium acetate method with four plasmids having a cycloheximide-resistance gene as a selectable marker, and a library DNA which was prepared by inserting the Sau3AI partially digested DNA fragments (5–10 kb) of the chromosomal DNA of *Candida utilis* ATCC 9950 strain into the BamHI site in the plasmid pCLBS10. However, when these plasmids were used in the cyclic form, no transformants were obtained. During this transformation experiment, the appearance of pseudo-resistant colonies which exhibited low resistance to cycloheximide or resistance to G418 was observed. The pseudo-resistant colonies refer to those which are often observed in the selection of transformants on the plate having antibiotics such as G418 or cycloheximide added thereto and spontaneously acquire resistance regardless of the presence of the drug-resistance gene of a selectable marker.

In this experiment, when cycloheximide was used for the selection of transformants, it was revealed that the appearance of pseudo-resistant colonies was suppressed by setting the concentration of cycloheximide in the plate at 40 μg/ml and incubating the plate at a temperature of 28° C. but not 30° C. Thus, the transformation experiments were conducted with the plasmids pCLRE2, pCLRX1 and pCLRX2 which had been digested with BglII, EcoRV and BglII, respectively, at the restriction enzyme sites within the rDNA region of the plasmid DNA in order to promote the integration of the DNA into the chromosome. As a result, cycloheximide-resistant clones were successfully obtained with use of the BglII digested plasmids pCLRE2 and pCLRX2 under the condition of electric capacitance of 25 μF, resistance of 600Ω and voltage of 5 KV/cm. These resistant strains have sizes obviously larger than those of a small pseudo-resistant strains obtained only seldom in a control experiment that no plasmid DNA was added, and were provided to be the transformants from the result of Southern analysis shown in Example 12.

Figure 17:
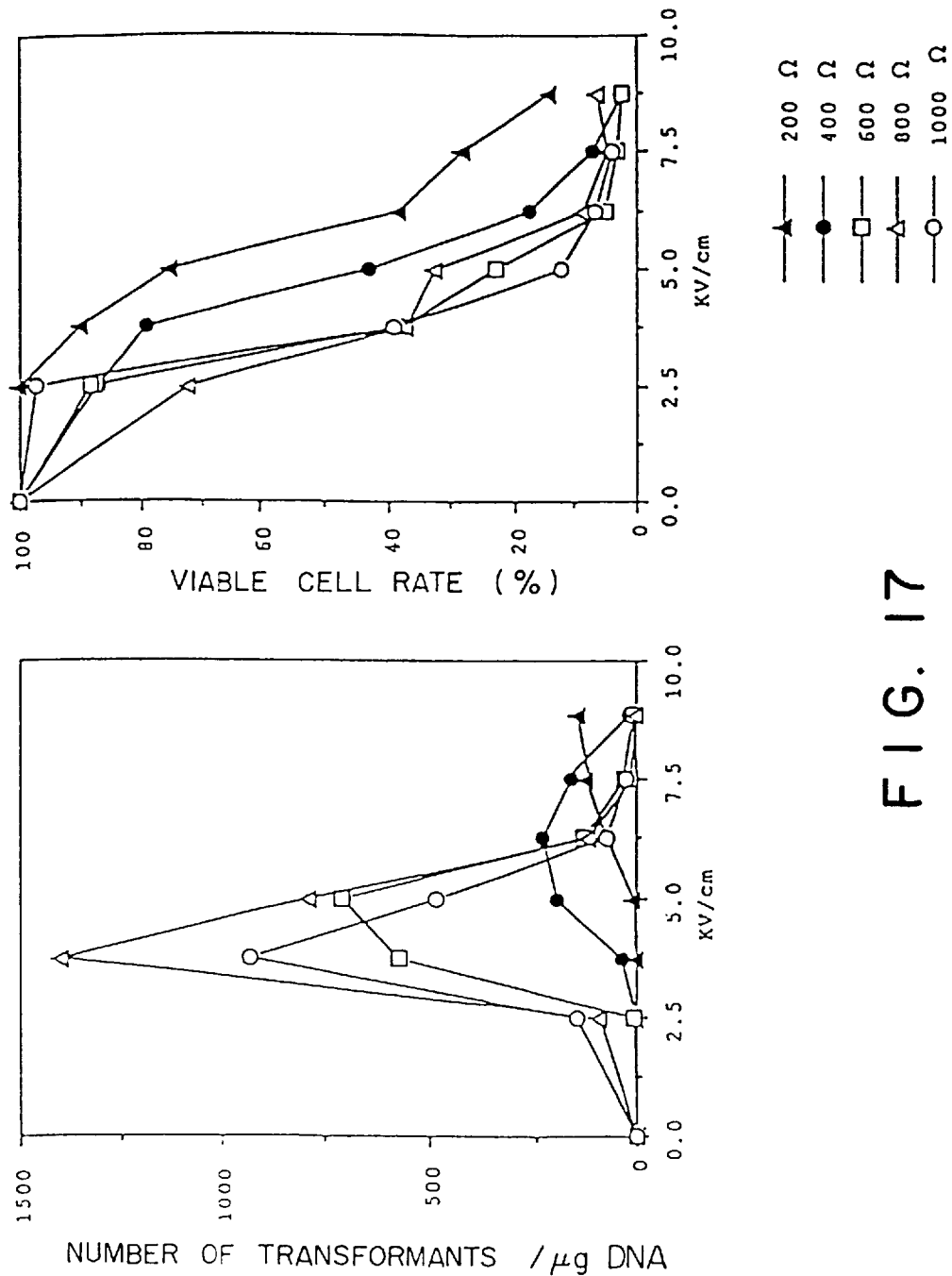
FIG. 17 illustrates the results of examining the viable cell ratio and the number of transformants of ATCC 9950 under a variety of electric pulse conditions.

In order to find the optimal condition of transformation, electric pulse experiments were conducted with the BglII digested plasmid pCLRE2 under conditions at a fixed electric capacitance at 25 μF with various combinations of resistance and voltage. The results are shown in FIG. 17, in which the post-pulse viable cell ratio and the number of cycloheximide-resistant transformants thus obtained are shown.

It has been found from the results that transformants are obtained in a high frequency of about 500–1,400 cells per 1 μg DNA under the conditions of electric capacitance of 25 μF, resistance of 600, 800 or 1,000Ω, and voltage of 3.75 or 5 KV/cm. The post-pulse viable cell ratio was about 10–40% under these conditions. The viable cell ratio was 40% or less in some conditions of resistance of 200 or 400Ω, but high frequencies of transformation were not obtained. At the resistance of 200 or 400Ω, time constant (time required for the attenuation of voltage to about 37% of the maximum) was in the range of 10 milliseconds or less. Further, under the conditions of the resistance of 600, 800 or 1,000Ω and the post-pulse viable cell ratio of about 10–40%, time constant was in the range of about 10–20 milliseconds. These results suggested that it is important for obtaining a high transformation frequency to apply the electric pulse to cells so that the post-pulse viable cell ratio is in the range of about 10–40% and the time constant is in the range of 10 milliseconds or more.

Moreover, it is preferred to add YPD medium containing 1M sorbitol to the cell solution and culture it with shaking after the electric pulse was applied. If the cells were directly spread on the selective plate containing cycloheximide without culture, no colonies were obtained.

In addition, the variations of the number of viable cells and the number of transformants were examined with the passage of time, and their rates of increase were compared to determine the optimal culturing time.

As a result, it was found that the rate of increase of transformants was higher than that of the number of viable cells during 6 hours of culture, but the number of viable cells and the number of transformants increase at the same ratio after 6 hours of culture. It was thus revealed that culture time of 6 hours was optimal.

The standard method for transformation of *Candida utilis* ATCC 9950 strain by electric pulse is described in Example 11.

Example 11

Method for transformation of *Candida utilis* ATCC 9950 strain by electric pulse After the colony grown on YPD plate is cultured with snaking in 5 ml of YPD liquid medium at 30° C. for about 8 hours, it is inoculated in 200 ml of YPD liquid medium at a concentration of $OD_{600}$=0.0024 and cultured with shaking at 30° C. for about 16 hours. After the cells have grown to logarithmic growth phase ($OD_{600}$=2.5), cells are collected by centrifugation at 1,400×g for 5 minutes. The cells are washed once with 100 ml of ice-cooled sterilized water, once with 40 ml of ice-cooled sterilized water, and once with 40 ml of ice-cooled 1M sorbitol. After the cells are suspended into 10 ml of 1M sorbitol, they are transferred in sterilized polypropylene tube and centrifuged again at 1,100×g for 5 minutes. After the supernatant is removed, the cells are suspended in an ice-cooled 1M sorbitol so as the volume of the final cell solution to be 2.5 ml.

The experiment of transformation by electric pulse is carried out with a Gene Pulser (Bio-rad). After 50 μl of the cell solution is mixed with 5 μl of a DNA sample, the mixture is placed in a 0.2 cm disposable cuvette, and electric pulse is applied under an appropriate condition. After the application of pulse, 1 ml of ice-cooled YPD medium containing 1M sorbitol is added, and the mixture is transferred in a sterilized polypropylene tube and cultured with shaking at 30° C. for about 6 hours. After the culture, the cell mixture was spread on the YPD selectable medium containing 40 μg/ml of cycloheximide and maintained at 28° C. for 3 or 4 days to obtain the colonies of the transformants.

Example 12

Detection of the plasmid DNA in the transformants by Southern analysis

Figure 18:
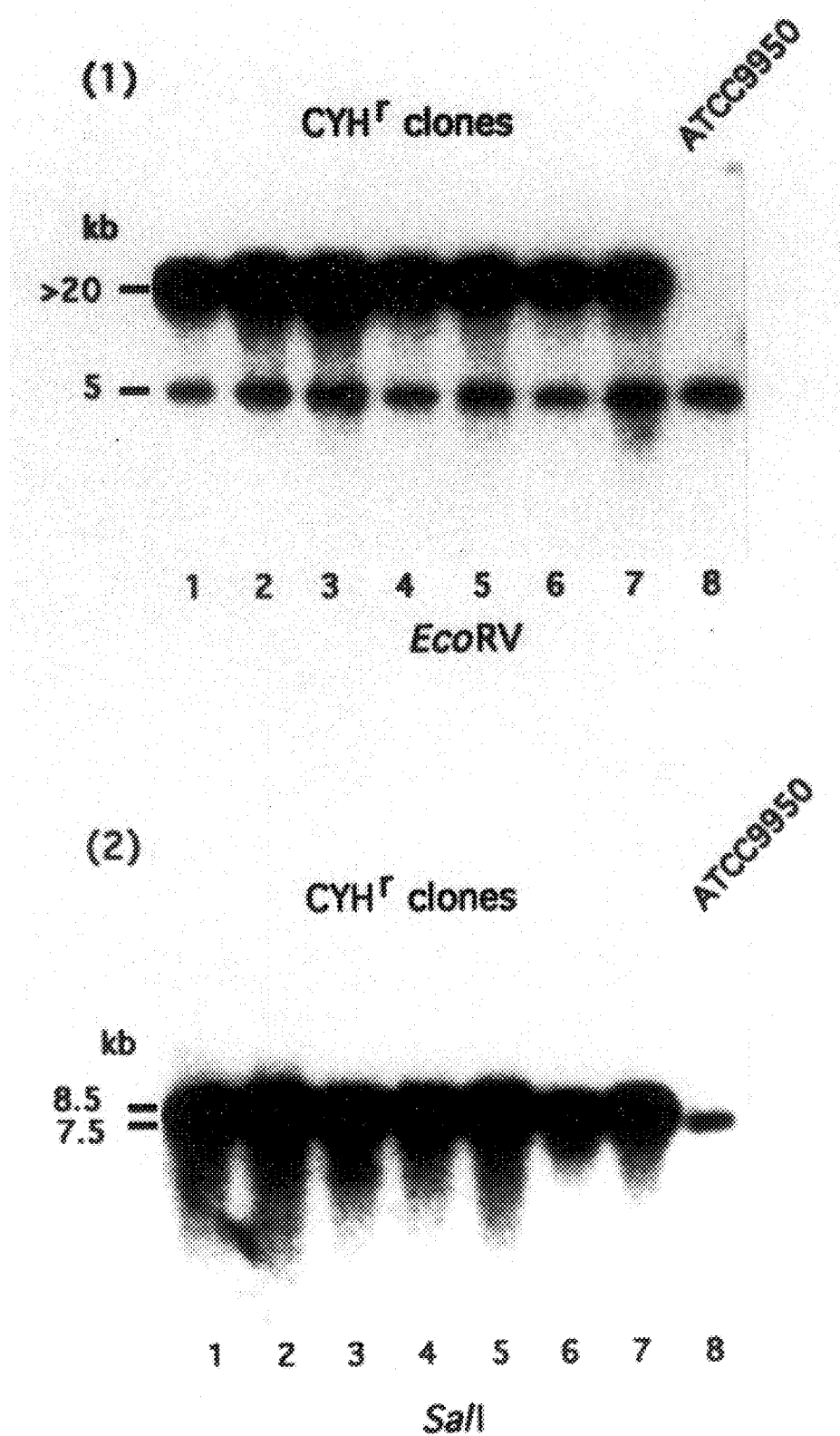
FIG. 18 illustrates the electrophoresis patterns of the results of the Southern blot analysis of the DNA of the ATCC 9950 strain transformed with plasmid pCLRE2.

Seven strains among the cycloheximide-resistant colonies obtained in Example 10 were analyzed by the Southern blot technique to examine whether these clones retained the plasmid DNA or not. Chromosomal DNA was prepared according to the method described in Methods in Yeast Genetics—A Laboratory Course Manual—Rose M. D. et al., p. 131–132, Cold Spring Harbor Laboratory Press, NY. The DNA thus prepared was digested with EcoRV or SalI and hybridized with a 1.8 kb $^{32}$P-labelled BamHI-HindIII fragment containing the L41 gene (FIG. 12) as a probe (FIG. 18).

As a result, in addition to the 5 kb band derived from the endogenous L41 gene, the band over 20 kb was detected by digestion with EcoRV. EcoRV cuts the rDNA locus but not the plasmid pCLRE2. It was thus considered that the detection of the over 20 kb band was due to the integration of the plasmid into the chromosome. Southern analysis in Example 15 proved that there are 2 copies of the L41 gene in one cell of *Candida utilis*. In consideration of the result of densitometric analysis, it was revealed that the number of copies of integrated plasmid DNA was in the range from about 6 copies (lane 7) to 15 copies (lane 2).

On the other hand, SalI cuts the plasmid pCLRE2 at one position. When the chromosomal DNA was digested with SalI, a 8.5 kb band corresponding to the length of the plasmid pCLRE2 was detected in addition to the 7.5 kb band derived from the endogenous L41 gene. The 8.5 kb band was considered to be generated by SalI digestion of vicinal plasmids due to tandem integration of plural plasmids in the chromosome.

In addition, when Southern analysis was conducted on 10 or more cycloheximide-resistant strains, the presence of the plasmid DNA was confirmed in all of the clones. The cycloheximide-resistant strains obtained in the transformation experiments in Example 10 were proved to be the transformants.

Example 13
Transformation of the other *Candida utilis* strains

It has been reported that *Candida utilis* has different chromosomal electrophoresis patterns depending on strains and exhibits the polymorphism of chromosomal length (Stoltenburg et al., Curr. Genet., 22, 441–446 (1992). Because of the anticipation of difference in genetic properties or transformation frequency depending on strains, transformation by the electric pulse method described in Example 11 was examined also on ATCC 9226 and ATCC 9256 strains in addition to the ATCC 9950 strain.

Pulse was applied under the condition of electric capacitance of 25 $\mu$F, resistance of 1,000$\Omega$ and voltage of 2.5–6.25 KV/cm. As the plasmid DNA, 2 $\mu$g of pCLRE2 digested with BglII was used.

The result are shown in Table 1. While the frequency was different depending on strains, cycloheximide-resistant colonies were obtained in any of the strains.

TABLE 1

| Transformation with plasmid pCLRE2 | | |
|---|---|---|
| Voltage Condition | Number of transformants per 2 $\mu$g of DNA | |
| (KV/cm) | ATCC 9226 | ATCC 9256 |
| 2.50 | 22 | 0 |
| 3.75 | 145 | 8 |
| 5.00 | 128 | 18 |
| 6.25 | 94 | 7 |

With respect to eight cycloheximide-resistant strains in total, i.e., four strains derived from ATCC 9226 and four strains derived from ATCC 9256 as well as two cycloheximide-resistant strains derived from ATCC 9950 as controls, chromosomal DNAs were prepared and digested with BglII. Southern analysis of the DNA was conducted with a $^{32}$P-labelled 1.8 kb BamHI-HindIII fragment containing the L41 gene (FIG. 12) as a probe.

Figure 19:
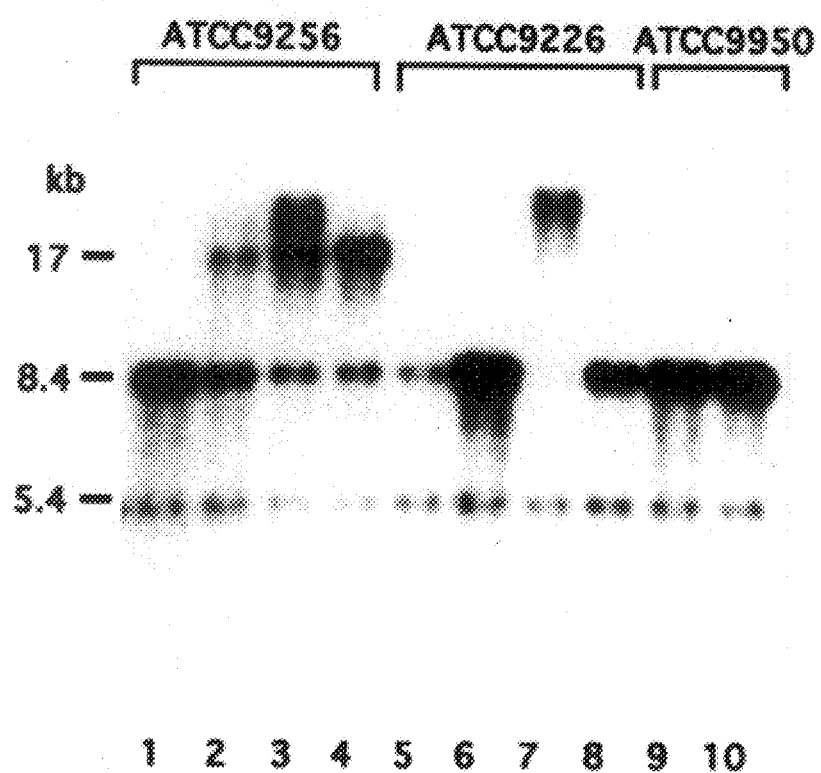
FIG. 19 illustrates the electrophoresis patterns of the results of the Southern blot analysis of the DNA of ATCC 9226, ATCC 9256 and ATCC9950 strains transformed with plasmid pCLRE2.

The results are shown in FIG. 19. A band derived from the plasmid DNA was observed in addition to the 5.4 kb band derived from the endogenous L41 gene on the chromosome in either of the strains. This indicates that these resistant strains are transformants retaining the plasmid DNA.

In some of the transformants derived from ATCC 9226 and ATCC 9256 strains, bands were observed in higher molecular weight in addition to the 8.4 kb band having the same size as plasmid DNA (lanes 2–4 and 7). This indicates that when the rDNA sequence on the plasmid is not identical to the rDNA sequence on the chromosome as the integration target, the BglII site at the ends of the plasmid DNA molecule integrated in the chromosome is sometimes deleted.

It has been proved by the Southern analysis in Example 15 that the number of copies of the L41 gene per cell of *Candida utilis* is two. The number of copies of the integrated plasmid was calculated by comparing the strength of the bands on the assumption that the 5.4 kb band corresponds to the two copies of the L41 gene. The densities of the bands were measured with an Imaging Analyzer BAS 2000 (Fuji Film).

As a result, the number of copies of the plasmid pCLRE2 was calculated to be in the range from 7 copies (lane 1) to 25 copies (lane 3) in the ATCC 9256 strain, from 3 copies (lane 5) to 11 copies (lane 6) in ATCC 9226 strain. On the other hand, the number of copies was calculated to be 11 copies (Lanes 9 and 10) in the ATCC 9950 strain.

These results indicate that transformants can be obtained with the cycloheximide-resistance L41 gene in ATCC 9226 and ATCC 9256 strains as well as the ATCC 9950 strain, and that a plurality of plasmids are integrated at the same time.

Example 14
Transformation of *Candida utilis* by the lithium acetate method and the modified method thereof The lithium acetate method (Ito et al., J. Bacteriol., 153, 163–168 (1983)) has been extensively used for the transformation of yeasts in Saccharomyces genus because it is simple and easy in operation. Thus, *Candida utilis* ATCC 9950 strain was tried to be transformed with the plasmid pCLRE2 which was digested to be linear with BglII according to the lithium acetate method and the modified lithium acetate method in which ethanol or DMSO was added (Soni et al., Current Cenet., 1993, 24, 455–459). In the modified lithium acetate method, ethanol was added after 10 minutes of the initiation of heat shock to the cell suspension so that the final concentration is 10%, and the mixture was incubated further for 10 minutes. DMSO was also added together with a polyethylene glycol solution to the cell suspension so that it has a final concentration of 10%. After the cells were suspended in YPD solution and cultured with shaking at 30° C. for 4 hours, cells were spread on the selectable plate containing cycloheximide and incubated at a temperature of 28° C. for 6 days.

As a result, 5 clones of the cycloheximide-resistant strains were obtained with 2 $\mu$g of DNA of the plasmid DNA by the modified lithium acetate method in which ethanol DNA was added. Southern analysis was conducted with chromosomal DNA prepared for 2 clones according to the method described in Example 13. Bands derived from the plasmid were observed and these clones were proved to be the transformants. The result indicates that *Candida utilis* treated with lithium acetate also has an ability to integrate DNA, although the transformation frequency is rather low as compared with the electric pulse method.

The experiment was conducted according to the method described by Soni et al., but it is also possible to improve the transformation frequency by further examining the treatment conditions.

Example 15

Transformation with a target of different rDNA region

1) Construction of plasmids pCLRE4 and pCLRE5 were constructed by inserting the 3.5 kb EcoRI fragment obtained from pCRE2 (FIG. 6), and the 2.4 kb EcoRI fragment obtained from pCRE3 (FIG. 6) into the EcoRI site of the plasmid pCLBS12 (FIG. 15) described in Example 9, respectively.

In addition, the 3 kb EcoRI-XbaI fragment and the 4.5 kb EcoRI-XbaI fragment cut out from pCRE1 (FIG. 6) in which a 7.5 kb EcoRI fragment containing rDNA was cloned were ligated between the EcoRI and XbaI sites of pBluescriptSK⁻, respectively. The XbaI site of each plasmid was converted into the EcoRI site by inserting EcoRI linkers (5'CCAAGCTTGG3' SEQ ID NO:39) to construct plasmids pCRE6 and pCRE7. The 3 kb and 4.5 kb EcoRI fragments cut out from these plasmids pCRE6 and pCRE7, respectively, were inserted into the EcoRI site of a plasmid pCLBS12 to construct plasmids pCLRE6 and pCLRE7, respectively.

Figure 20:
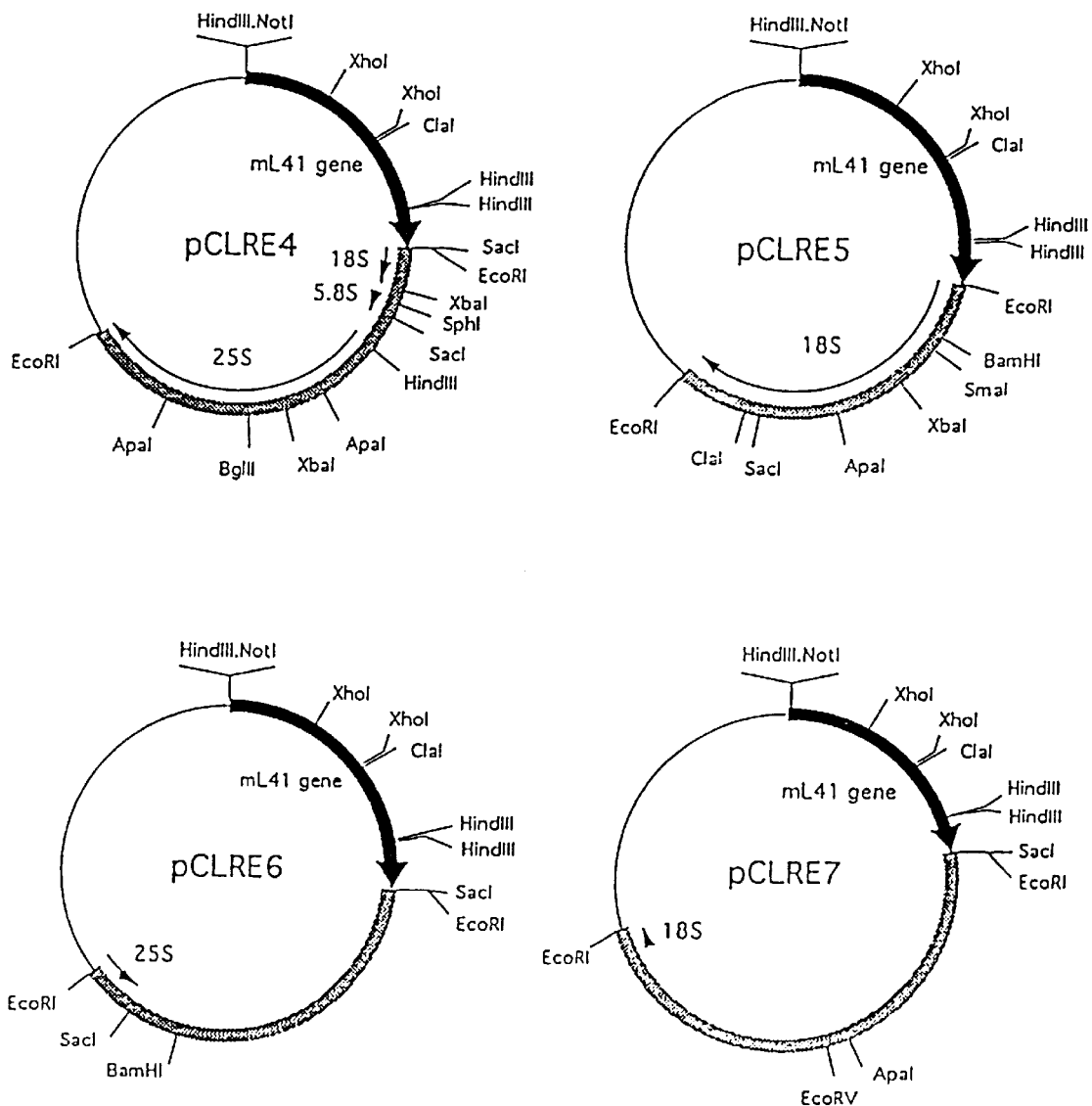
FIG. 20 illustrates the construction of plasmids pCLRE4, pCLRE5, pCLRE6 and pCLRE7.

The structures of the plasmids pCLRE4, pCLRE5, pCLRE6 and pCLRE7 are shown in FIG. 20.

2) Transformation

Each of the plasmids pCLRE4, pCLRE5, pCLRE6 and pCLRE7 prepared was digested with a restriction enzyme into a linear DNA. The ATCC 9950 strain was transformed with 1 µg of the DNA by the electric pulse method described in Example 11. Transformations were conducted under the pulse condition of electric capacitance of 25 µF, voltage of 5 KV/cm and resistance of 800Ω with post-pulse culture time for 18 hours. Restriction enzymes which were able to cut sites found in rDNA fragments were employed. That is, the plasmid pCLRE4 was digested with BglII, pCLRE5 with BamHI or XbaI, pCLRE6 with BamHI, and pCLRE7 with ApaI or EcoRV, respectively. The plasmid pCLRE4 was also digested at the ClaI site in the L41 gene to compare the difference of transformation frequencies due to the difference of integrated target genes.

Two runs of the experiment were conducted. The results are shown in Table 2.

TABLE 2

Transformation with plasmids pCLRE4, pCLRE5, pCLRE6 and pCLRE7

| Plasmid | Number of transformants per 1 µg of DNA | |
|---|---|---|
| | First | Second |
| pCLRE4 (BglII) | 786 | 593 |
| pCLRE4 (ClaI) | 87 | 11 |
| pCLRE5 (BamHI) | 0 | 0 |
| pCLRE5 (XbaI) | 1 | 18 |
| pCLRE6 (BamHI) | 301 | 775 |
| pCLRE7 (ApaI) | 409 | 754 |
| pCLRE7 (EcoRV) | 577 | 640 |

Digestion in the rDNA fragment of the plasmids pCLRE4, pCLRE6 or pCLRE7 provided a high transformation frequency, and several hundred transformants were obtained per 1 µg DNA in either of the plasmids. On the other hand, by the digestion of the plasmid pCLRE5 with either of BamHI or XbaI, transformation frequency was very low as compared with the cases of the other plasmids. This indicates that transformation frequency varies largely depending on the fragments used as targets of transformation even in the rDNA region.

In addition, digestion of the plasmid pCLRE4 at the ClaI site in the L41 gene, gave the transformation frequency at about 1/10- about 1/50 as compared with the digestion at the BglII site in the rDNA. Furthermore, Southern analysis described below indicates that the plasmid molecule was integrated in the L41 gene locus when it was digested at the ClaI site, and in the rDNA locus when it was digested at the BglII site, respectively.

It has been revealed from these results that the use of the rDNA having multiple number of copies in the chromosome as a target leads to a high transformation frequency.

3) Southern analysis

Cycloheximide-resistant strains were prepared with pCLRE4 which had been digested with BglII or ClaI, pCLRE5 which had been digested with XbaI, pCLRE6 which had been digested with BamHI, and pCLRE7 which had been digested with ApaI. Four strains were obtained with respect to each plasmid. From these strains, chromosomal DNAs were prepared. The DNA samples prepared were digested with BglII or with BglII and NotI, and subjected to Southern analysis with a $^{32}$P-labelled 1.8 kb BamHI-HindIII fragment containing the L41 gene (FIG. 12) as a probe (FIG. 21).

With respect to the strain in which the plasmid pCLRE4 was integrated, by the digestion with BglII a 8.4 kb band having the same size as the plasmid DNA which was generated by the cut at the BglII site in the plasmid DNA molecule was observed in addition to the 5.4 kb band derived from the endogenous L41 gene (FIG. 21(1), lane 1–8). Further, with respect to the strain in which the plasmid digested with ClaI was integrated, 7.4 kb and 6.4 kb bands were observed in addition to the two bands as just described (lane 1–4). The two bands were generated from the presence of; the BglII sites in the plasmid molecules at both ends of the integrated plasmid molecule and generated by insertion of the plasmids at one of the chromosomal L41 genes locus; and BglII sites in the L41 gene. This indicated that the plasmid molecules have been integrated into the L41 gene locus by homologous recombination. The results indicated that the plasmid molecules have been integrated in the L41 gene locus when it was digested at the ClaI site, and in the rDNA locus when it was digested at the BglII site, respectively. This reveals that the positions for integrating the plasmid can be selected depending on the cutting site. Furthermore, since in lanes 1–4, 5.4 kb, 7.4 kb and 6.4 kb bands have almost the same density, the presence of 2 copies of the L41 gene in the chromosome was proved.

In the strains in which the plasmids pCLRE5, pCLRE6 and pCLRE7 have been integrated, by BglII and NotI digestion, some bands derived from the plasmids integrated in the chromosome were observed in addition to the 5.4 kb band derived from the endogenous L41 gene (FIG. 21(2)). Among them, bands having the same size with the plasmids were observed, i.e. the 7.3 kb band for pCLRE5 (lanes 1–4), the 8.0 kb band for pCLRE6 (lanes 5–8), and 9.4 kb band for pCLRE7 (lanes 9–12). These bands are generated from the vicinal plasmids which have been integrated in tandem by digestion with NotI which has only one cutting site in these plasmid. Moreover, the 7 kb band in pCLRE5 (lanes 1–4), the 6.9 kb band in pCLRE6 (lanes 5–8), and the 11 kb band in pCLRE7 (lanes 9–12) were also observed. These sizes are the same as the lengths of the fragment from the BglII site in the rDNA locus to the NotI sites in the plasmid DNAs obtained by BglII+NotI digestion when the plasmid DNAs have been integrated in the rDNA locus by homologous recombination. This indicates that the plasmid DNAs have been integrated at the cut sites in the chromosome by homologous recombination.

The number of copies of the integrated plasmid was obtained by comparing the densities of bands on the assumption that the 5.4 kb bands in lanes 1–4 in FIG. 21(1) correspond one copy of the L41 gene, the 5.4 kb bands in lanes 5–8 in FIG. 21(1) and in lanes 1–12 in FIG. 21(2) correspond to two copies of the L41 gene. The density of bands was measured with an Imaging Analyzer BAS200 (Fuji Film).

It was revealed that from three copies (lane 4) to five copies (lanes 1 and 3) of the plasmid pCLRE4 were inserted in the L41 gene locus, and from two copies (lane 8) to eight copies (lane 5) in the rDNA locus. From this result, it was observed that strains in which the plasmid DNAs have been integrated in the rDNA locus with a higher copy number tend to be selected. It is also suggested by the fact that in the strains of Example 12 in which the plasmid pCLRE2 has been integrated in the rDNA locus, the number of copies of the plasmid DNA integrated were 6 to 15, while in the strain of Example 16 in which the plasmid pCLRE2 has been integrated in the URA3 gene locus, the number of the plasmid DNA integrated were about 3 to 4.

It was also revealed that from three copies (FIG. 21(2), lane 4) to five copies (lane 2) of the plasmid pCLRE5, from three copies (lane 8) to six copies (lanes 5 and 6) of the plasmid pCLRE6, and from three copies (lane 12) to five copies (lane 9) of the plasmid pCLRE7 have been integrated, respectively.

Example 16

Integration of plasmid into the URA3 gene locus

Plasmid pCLURA1 was constructed by inserting the 5 kb EcoRI fragment containing the URA3 gene (FIG. 7) into the EcoRI site of the plasmid pCLBS12 (FIG. 15). The plasmid was cut at the PstI site in the URA3 gene locus. The ATCC 9950 strain was transformed with this plasmid according to the electric pulse method described in Example 11. Pulse was applied under the condition of an electric capacitance of 25 $\mu$F, a resistance of 800$\Omega$ and a voltage of 5 KV/cm. Thus, forty cycloheximide-resistant colonies per 1 $\mu$g DNA were obtained thereby.

Chromosomal DNAs were prepared for four clones among the cycloheximide-resistant strains thus obtained. The DNA thus prepared was digested with BglII or with SalI+NotI and subjected to Southern analysis. As probes, the 1.8 kb BamHI-HindIII fragment containing the L41 gene (shown in FIG. 12) for the DNA digested with BglII and the 2.3 kb HindIII-EcoRI fragment containing the URA3 gene (shown in FIG. 8) for the DNA digested with SalI+NotI were used after labelled with $^{32}$P.

Figure 22:
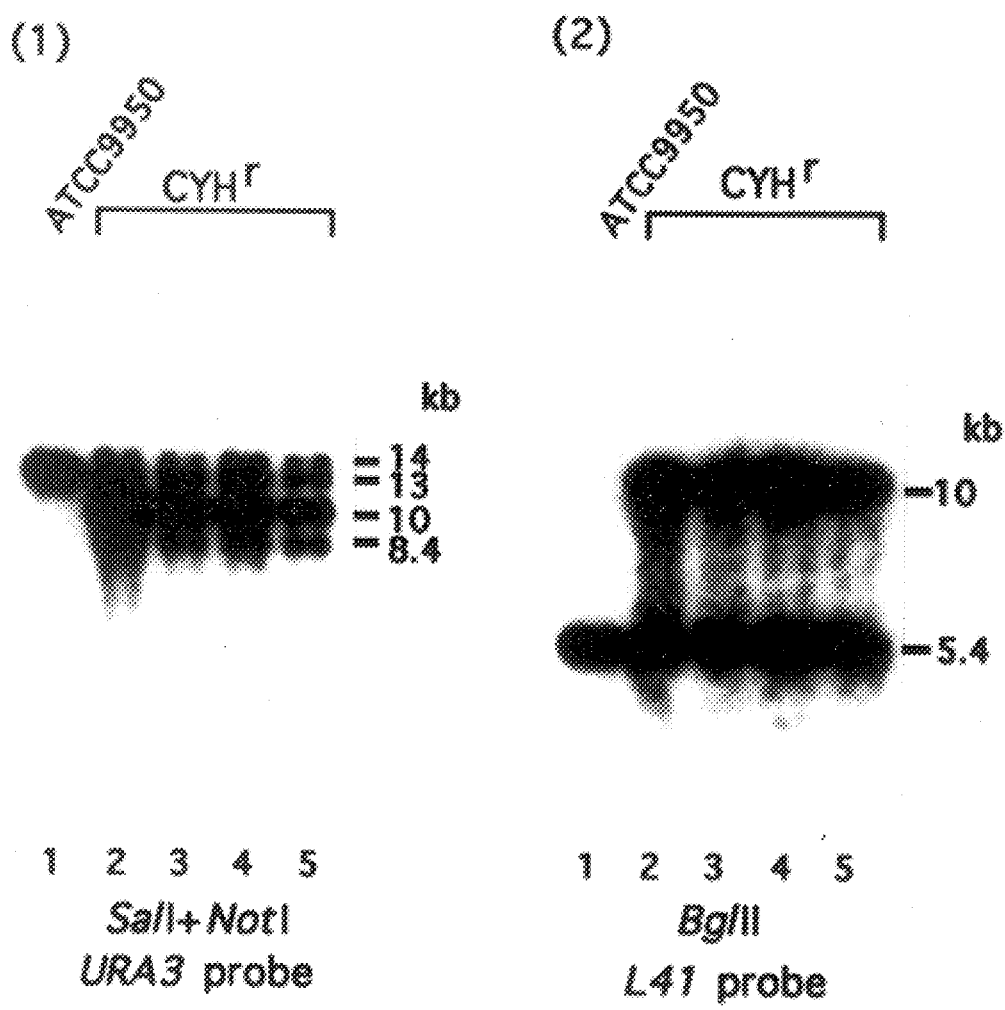
FIG. 22 illustrates the electrophoresis patterns of the results of the Southern blot analysis of the DNA of ATCC 9950 strain transformed with plasmid pCLURA1.

The results are shown in FIG. 22. With respect to the parent strain ATCC 9950, when the URA3 gene was used as a probe for the DNA digested with SalI+NotI, a 13 kb band derived from the endogenous URA3 gene was observed (FIG. 22(1), lane 1). On the other hand, with respect to the resistant strain, in addition to the 13 kb band, a 10 kb band generated from the NotI digestion of plural plasmids tandemly integrated, and 8.4 kb and 14 kb bands generated by the insertion of the plasmids at one of the URA3 genes on chromosome were observed (lanes 2–5). These two bands were generated from the presence of; the NotI sites in the plasmid molecules at both ends of the integrated plasmid molecules; and the SalI site in the URA3 gene region. This indicated that the plasmid molecules have been integrated in the URA3 gene locus by homologous recombination.

Furthermore, in the transformants, the 13 kb band derived from the endogenous URA3 gene and the 8.4 kb and 14 kb bands derived from the plasmid molecules integrated in the chromosome have almost the same densities. This revealed that the number of copies of the URA3 gene is two copies per cell like the L41 gene, and that one copy in the transformants has been disrupted by the insertion of the plasmids. It has been also revealed by comparing these four bands (14 kb, 13 kb, 10 kb and 8.4 kb) that the number of the plasmid integrated were three copies (lanes 3 and 5) or four copies (lanes 2 and 4).

When the L41 gene is used as a probe for the DNA digested with BglII, a 5.4 kb band derived from the endogenous L41 gene was observed in the parent strain ATCC9950. In addition to the 5.4 kb band, a 10 kb band having the same size of the plasmid DNA was observed in the resistant strains (lanes 2–5).

Example 17

Expression of a heterologous gene, glucoamylase gene, in *Candida utilis*

(1) Construction of plasmids for expressing the glucoamylase gene (STA1 gene)

A plasmid for expressing the STA1 gene was constructed according to the procedure illustrated in FIG. 23.

The STA1 gene was first cloned from a genomic DNA library of *Saccharomyces diastaticus* 5106-9A (a leu2, arg4, STA1) (Yamashita and Fukui, Agric. Biol. Chem., 47, 2689–2692) according to the following procedure. Chromosomal DNA was prepared from the 5106-9A cell, partially digested with Sau3AI and subjected to agarose gel electrophoresis to prepare about 20–30 kb DNA fragments. The DNA fragments and $\lambda$-phage vector EMBL3 digested with BamHI and then dephosphorylated (Stratagene Cloning Systems) were ligated with T4 ligase. The ligated mixture was in vitro packaged with GigapackII Gold Packaging Extract (Stratagene Cloning Systems) to construct the genomic DNA library of the chromosomal DNA.

Two oligonucleotides:

5'ACCACTATTACCACTACGGTTTGCT-
    CTACA3'            (SEQ ID NO: 19), and

5'GACACATCTCTGACGAGCATGACTT-
    GGTTG3'            (SEQ ID NO: 20)

which had been synthesized on the basis of the described DNA sequence of a STA1 gene (Yamashita et al., J. Bacteriol., 161, 567–573, 1985) were $^{32}$P-labelled at the end with T4 kinase and used as a probe for screening about 20,000 plaques of the genomic DNA library. As a result, a clone which was positive to either of the two probes was obtained.

From the phage clone containing the STA1 gene, a 4 kb BglII-HpaI fragment containing the STA1 gene was cloned between the BamHI and HindIII of pUC19 to construct the plasmid pUSTA1 (FIG. 23).

Further, the plasmid pUSTA1 was cut with a StuI site present 5 bp downstream of the initiation codon ATG, and the following synthetic adapter (SEQ ID NO. 21) containing a XbaI site and an initiation codon:

5'-CTAGATGGTAGG-3'

3'-TACCATCC-5' was ligated. Then, partial digestion of the plasmid with SalI gave the STA gene as a 2.7 kb XbaI-SalI fragment.

Furthermore, pUC12 was digested with PstI and HindIII, treated with T4 DNA polymerase, and BglII linkers were ligated to construct a plasmid pUC12BglII. The 2.7 kb XbaI-SalII fragment containing the STA1 gene was inserted between the XbaI and SalII of the plasmid pUC12BgII to construct a plasmid pUSTA2.

The 2.7 kb XbaI-BglII fragment was cut out from the plasmid STA2 and inserted between the XbaI and BamHI sites of the expression vector pPGKPT4 to construct a plasmid pGKSTA1.

Furthermore, a 4.9 kb NotI fragment containing the PGK gene promoter, the STA1 gene and the PGK gene terminator was cut out from the plasmid pGKSTA1. The fragment was inserted into the NotI site of the plasmid pCLBS12 to construct a plasmid pCLSTA1, and into the NotI site of the plasmid pCLRE4 to construct a plasmid pCLRSTA1, respectively.

(2) Transformation of *Candida utilis* and glucoamylase expression

ATCC 9950, ATCC 9226 and ATCC 9256 strains were transformed with the plasmid pCLRSTA1 digested with BglII according to the electric pulse method described in Example 11. Pulse was applied under the condition of electric capacitance of 25 $\mu$F, resistance of 1,000$\Omega$, and voltage of 3.75 KV/cm or 6.25 KV/cm.

Cycloheximide-resistant colonies were obtained in either of the strains although frequencies were different depending on strains.

Glucoamylase activity was examined for two strains of each of the transformants on a plate containing starch as a substrate (3% Soluble starch (Katayama), 2% polypeptone, 1% yeast extract, 3.3×10$^{-3}$% Bromocresol purple, 2% Bacto agar). As a result, for all of the transformants derived from the three strains halos due to secreted glucoamylase were observed. Thus, the expression of the gene were confirmed. In addition, the ATCC 9950 strain was transformed with an AflII digested plasmid pCLSTA1. When the expression of the glucoamylase gene integrated at the L41 gene locus was further examined, the formation of halos was observed as well.

Furthermore, the glucoamylase activities of these transformants were measured. The cells were cultured in YPD liquid medium overnight, and the supernatant was used as a crude enzyme solution. The reaction was conducted in 500 $\mu$l of a reaction solution containing 400 $\mu$l of the crude enzyme solution, 0.5% soluble starch and 100 mM sodium acetate (pH 5.0) at 50° C. for 20 minutes. After reaction, the enzyme was inactivated by heat treatment at 100° C. for 5 minutes, and the concentration of glucose generated was determined with a commercially available kit (Glucose B-Test (Wako Pure Chemical Industries, Ltd.)).

The activity of glucoamylase was defined as 1 unit when the amount of glucose isolated under the reaction condition is 100 $\mu$g. The values of the activity per 1 ml supernatant of the culture are shown in Table 3.

TABLE 3

Glucoamylase activities of the *Candida utilis* yeasts transformed with plasmids pCLSTA1 or pCLRSTA1

| Plasmid | Glucoamylase activity (units/ml) | | |
|---|---|---|---|
| | ATCC 9256 | ATCC 9266 | ATCC 9950 |
| pCLRSTA1(BglII) | 11.3 | 7.9 | 8.3 |
| pCLRSTA1(BglII) | 10.5 | 6.6 | 8.5 |
| pCLSTA1(AflII) | — | — | 7.6 |

TABLE 3-continued

Glucoamylase activities of the *Candida utilis* yeasts transformed with plasmids pCLSTA1 or pCLRSTA1

| Plasmid | Glucoamylase activity (units/ml) | | |
|---|---|---|---|
| | ATCC 9256 | ATCC 9266 | ATCC 9950 |
| pCLSTA1(AflII) | — | — | 8.8 |
| -DNA | 0.0 | 0.0 | 0.0 |

Activities were measured on two independent transformed strains.
—: no measurement.

It was revealed that the signal sequence of glucoamylase protein was recognized and the enzyme was secreted into medium in the ATCC 9950, 9226, and 9256 strains, although glucoamylase is a heterologous protein derived from *Saccharomyces diastaticus*.

Figure 24:
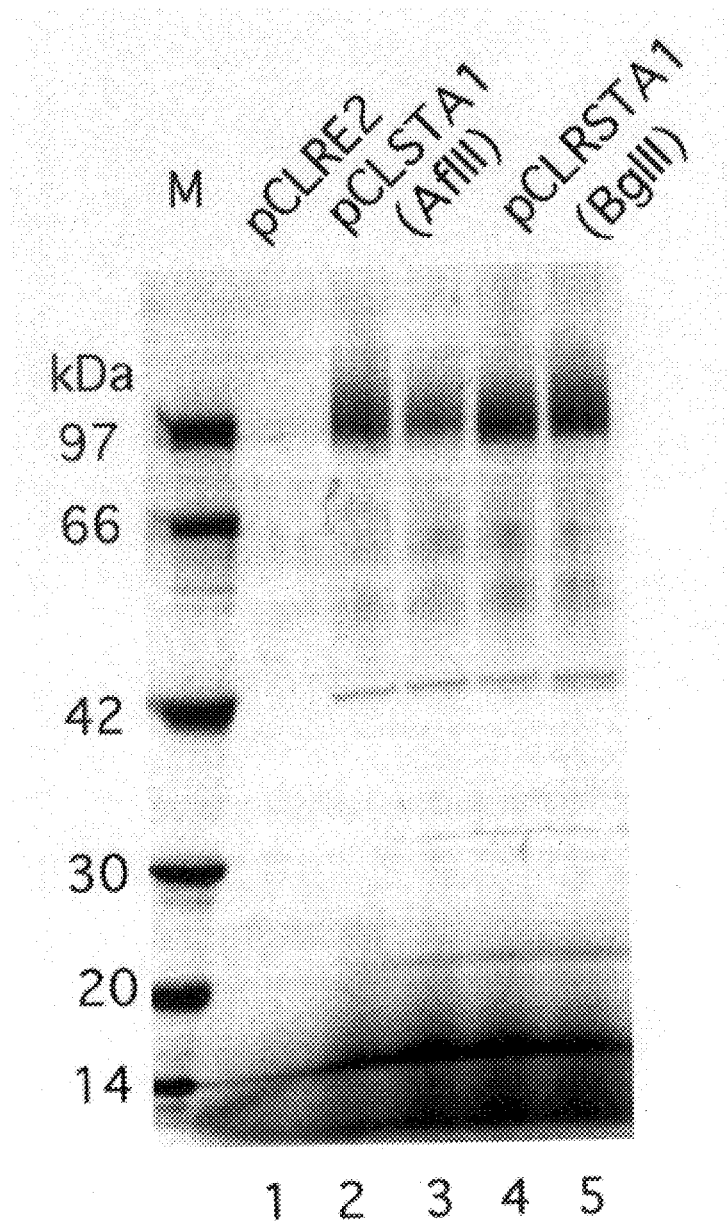
FIG. 24 illustrates the result of the SDS polyacrylamide gel electrophoresis of the supernatant of the culture of the ATCC 9950 strain transformed with plasmid pCLRSTA1.

Moreover, Two ATCC 9950 strains transformed with each of the plasmid pCLSTA1 digested with BglII or the plasmid pCLSTA1 digested with AflII were cultured in YPD liquid medium containing 40 $\mu$g/ml cycloheximide and 5% glucose at 30° C. for 4 days. A 10 $\mu$l portion of the cultured medium was subjected on 4–20% SDS polyacrylamide gel electrophoresis to analyze the proteins in the culture (FIG. 24). The gel was stained with Coomassie brilliant blue. As a control, culture medium of the strain transformed with the BglII digested plasmid pCLRE2 was analyzed (lane 1). An about 100 kDa protein corresponding to glucoamylase was observed in either cultures, and the amount of the protein was estimated at about 2–5 $\mu$g from the densities of the stained bands. This indicates that the glucoamylase gene has been expressed at a high level and has been secreted in the medium. It has been thus revealed that *Candida utilis* can be used as an appropriate host/vector system for producing secretory proteins.

Example 18

Expression of a heterologous gene, (lacZ gene), in *Candida utilis*

(1) Construction of plasmids for expressing lacZ gene

Figure 25:
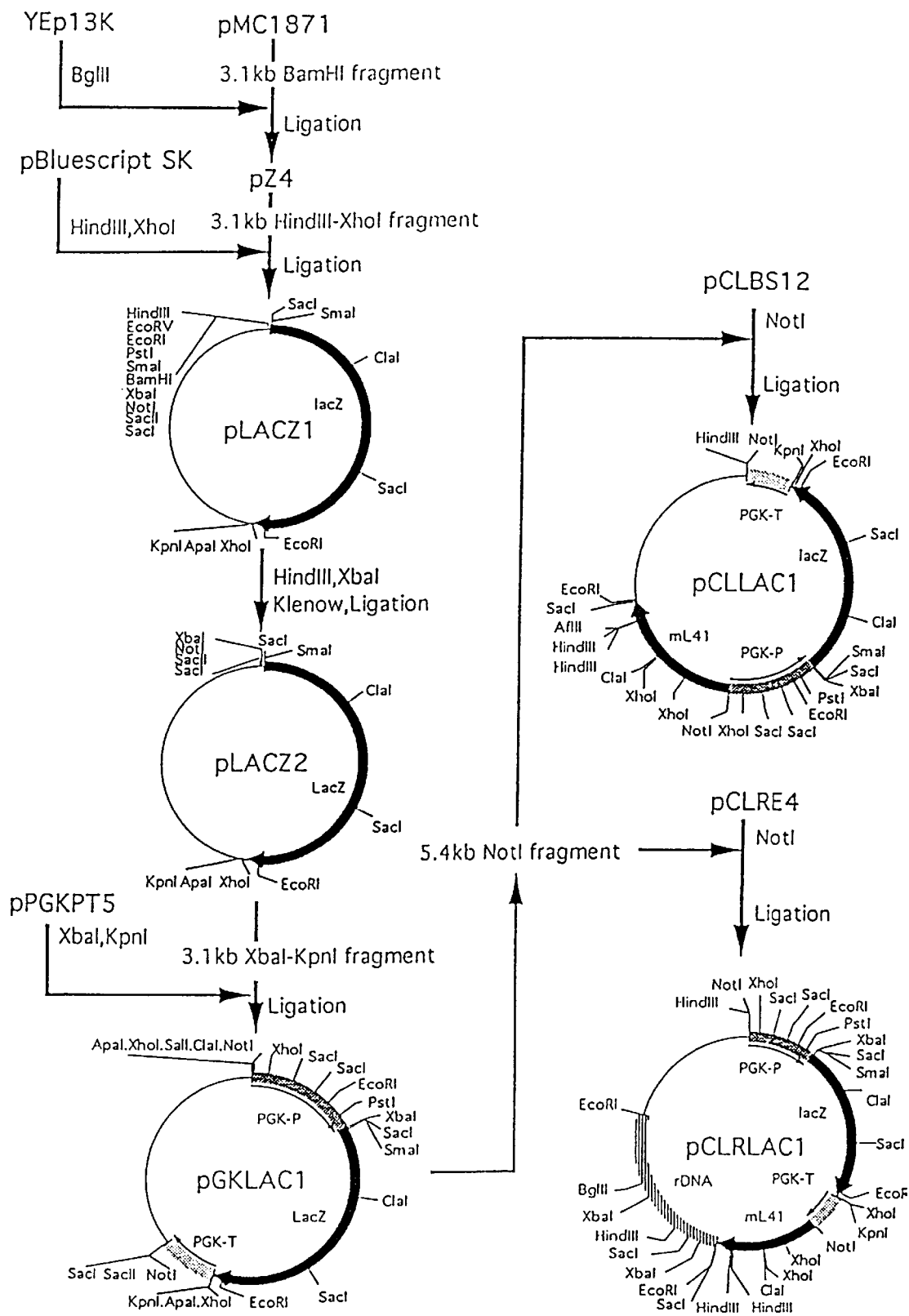
FIG. 25 illustrates the construction of plasmids pCLLAC1 and pCLRLAC1.

Plasmids for expressing the lacZ gene were constructed according to the procedure illustrated in FIG. 25.

Firstly, the lacZ gene encoding $\beta$-galactosidase was cut out as a 3.1 kb BamHI fragment from plasmid pMC1871 (Pharmacia). The fragment was ligated to the BglII site of a plasmid YEp13K (Sone et al., Appl. Environ. Microbiol., 54, 38–42 (1988)) to select a plasmid pZ4 having a HindIII site at the 5' side of the gene.

A lacZ gene having an initiation codon ATG was cut out as a 3.1 kb HindIII-XhoI fragment from the plasmid. The fragment was then ligated between the sites of HindIII and XhoI in pBluescript SK⁻ to construct a plasmid pLACZ1.

This plasmid was digested with HindIII+XbaI, subjected to Klenow treatment, and recyclized to construct a plasmid pLACZ2.

Furthermore, the lacZ gene was cut out as a 3.1 kb XbaI-KpnI fragment from the plasmid, and ligated between the sites of XbaI and KpnI in the plasmid pPGKPT5 (FIG. 4) to construct a plasmid pGKLAC1.

In addition, a 5.4 kb NotI fragment containing the PGK gene promoter, the lacZ gene and the PGK gene terminator was cut out from the plasmid pGKLAC1, and inserted into the NotI site of the plasmid pCLBS12 and the NotI site of the plasmid pCLRE4 to construct plasmids pCLLAC1 and pCLRLAC1, respectively.

(2) Transformation of *Candida utilis* and the confirmation of $\beta$-galactosidase activity The ATCC 9950 strain was transformed with the plasmid pCLRLAC1 digested with BglII or the plasmid pCLLAC1 digested with AflII by the electric pulse method described in Example 11. Two strains of each of the transformed ATCC 9950 strains were cultured up to logarithmic growth phase ($OD_{600}$=about 2–3) in 5 ml of YPD liquid medium for 6 hours. β-Galactosidase activity was measured according to the method described in Methods in Yeast Genetics—A Laboratory Course Manual—Rose, M. D. et al., p. 155–159, Cold Spring Harbor Laboratory Press, NY (1990). Specifically, after the collected cells were suspended in 1 ml of Z buffer, 3 drops of chloroform and 2 drops of 0.1% SDS were added, and the mixture was vortexed for 10 seconds. After incubation at 28° C. for 5 minutes, 0.2 ml of ONPG solution was added, and the mixture was incubated for further 10 minutes. Then, 0.5 ml of $Na_2CO_3$ solution was added to stop the reaction. After the measurement of $OD_{420}$, the β-galactosidase activity was calculated according to the equation. The β-galactosidase activity was defined as 1 unit when ortho-nitrophenol is produced in an amount of 1 nmol at 28° C. for 1 minute. The activities of the cells obtained per $OD_{600}$ are shown in Table 4.

TABLE 4

β-galactosidase activities of the ATCC 9950 strains transformed with the plasmids pCLLAC1 or pCLRLAC1

| Plasmid | β-galactosidase activity (units/$OD_{600}$) |
| --- | --- |
| pCLLAC1 (AflII) | 6.4 |
| pCLLAC1 (AflII) | 6.7 |
| pCLRLAC1 (BglII) | 6.8 |
| pCLRLAC1 (BglII) | 7.0 |
| -DNA | 0.1 |

From the result, it was confirmed that both of the ATCC 9950 strains transformed with the plasmids pCLRLAC1 or pCLLAC1 showed the activity, indicating the lacZ gene derived from *E. coli* was expressed and active β-galactosidase was produced in *Candida utilis*. It has been known that the leucine codon CUG is translated into serine in some yeasts of the Candida genus such as *Candida maltosa* or *C. albicans* (Ohama et al., Nucleic Acids Res., 21, 4039–4045, 1993), so that the lacZ gene derived from *E. coli* is not translated into an active β-galactosidase (Sugiyama et al., Yeast, 11, 43–52 (1995)). In this Example, active β-galactosidase is produced in *Candida utilis*, and it has been shown in Example 17 that glucoamylase is produced in a high amount. It is thus believed that *Candida utilis* can be used as a host for expressing heterologous genes.

Example 19
Expression of a heterologous gene (APT gene) in *Candida utilis*

(1) Construction of plasmids for expressing the APT gene

Figure 26:
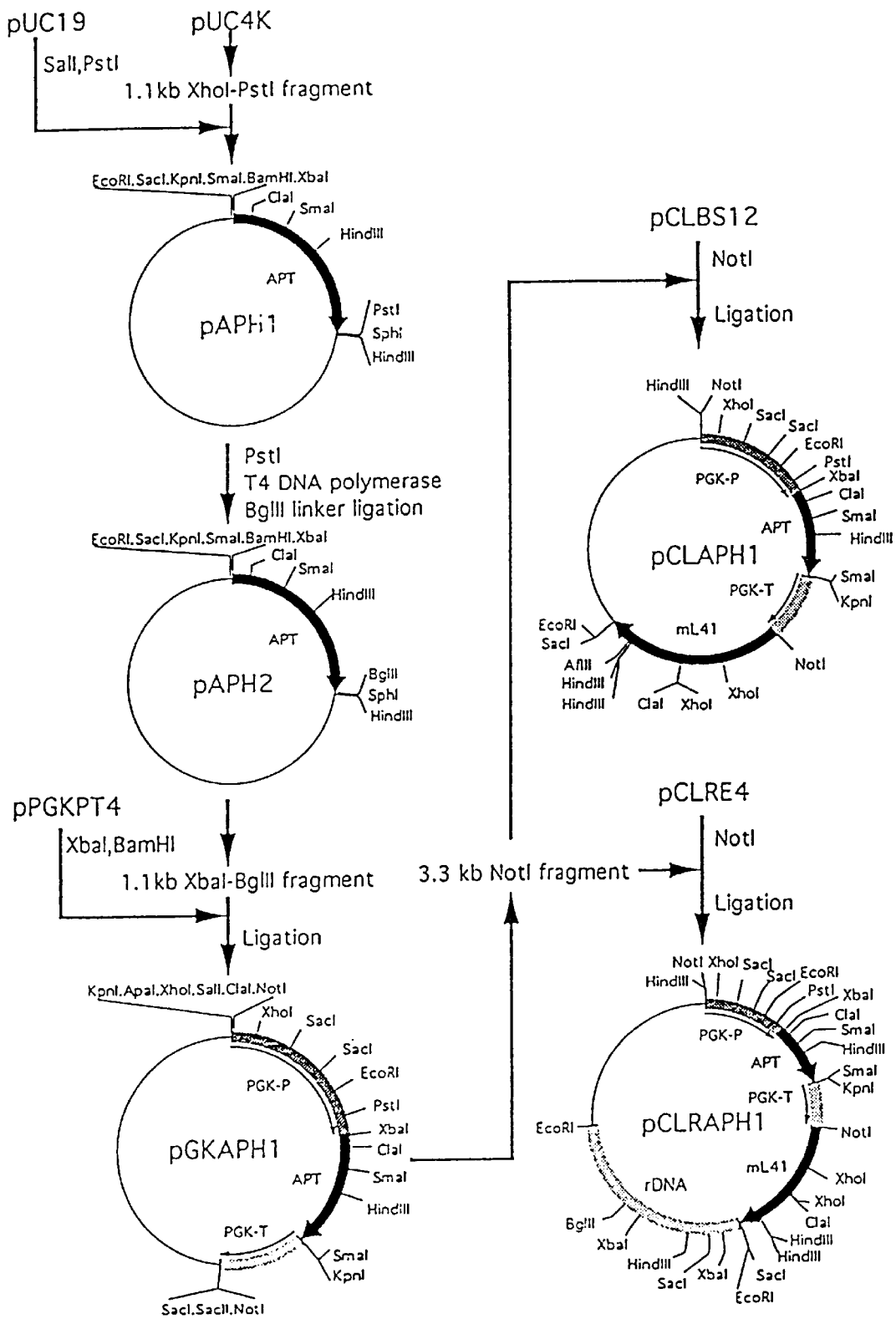
FIG. 26 illustrates the construction of plasmids pCLAPH1 and pCLRAPH1.

Plasmids for expressing the APT gene were constructed according to the procedure illustrated in FIG. 26.

Firstly, a 1.1 kb XhoI-PstI fragment was cut out from plasmid pUC4K (Pharmacia) containing aminoglycoside phosphotransferase derived from transposon Tn903 (APT gene) and inserted between SalI and PstI of pUC19 to construct a plasmid pAPH1.

After the plasmid pAPH1 was digested with PstI and treated with T4 DNA polymerase to form blunt ends, BglII linkers (5'CAGATCTG3') were inserted to form a plasmid pAPH2.

Furthermore, the APT gene was cut out as a 1.1 kb XbaI-BglII fragment from the plasmid pAPH2 and inserted between the XbaI and BamHI sites of the expression vector pPGKPT4 (FIG. 4) to construct a plasmid pGKAPH1.

In addition, a 3.3 kb NotI fragment containing the PGK gene promoter, the APT gene and the PGK terminator was cut out from the plasmid pGKAPH1. This fragment was then inserted into the NotI site of the plasmids pCLBS12 and pCLRE4 to construct plasmids pCLAPH1 and pCLRAPH1, respectively.

(2) Transformation of *Candida utilis* and confirmation of resistance to G418

ATCC 9950, ATCC 9226 and ATCC 9256 strains were transformed with the plasmid pCLRAPH1 digested with BglII according to the electric pulse method described in Example 11. Pulse was applied under the condition of electric capacitance of 25 μF, resistance of 1,000Ω, and voltage of 3.75 KV/cm or 6.25 KV/cm.

As a result, cycloheximide-resistant colonies were obtained in either of the strains although frequencies were different depending on strains. The growth of cells was examined for two strains of each of the transformants on YPD plates containing various concentrations of G418. As a result, the growth of the transformants was confirmed for all of the three strains of *Candida utilis*, and it indicates that the APT gene has expressed in these transformants.

In addition, the ATCC 9950 strain was transformed with an AflII digested plasmid pCLAPH1 in order to examine the expression of genes integrated at the L41 gene locus. As a result, the growth of transformants was confirmed for the strain, and expression was also confirmed on the APT gene integrated at the L41 gene locus.

(3) Stability of the integrated plasmid

The stability of the integrated plasmid DNA was examined in the following procedure for two ATCC 9950 strains transformed with each of the plasmid pCLRAPH1 digested with BglII or the plasmid pCLAPH1 digested with AflII. The transformant was first cultured up to the stationary phase in 5 ml of YPD liquid medium containing 40 μg/ml cycloheximide. The generation number at the time was referred to as zero. Then, a 5 μl portion of the cell culture was inoculated in 5 ml of YPD liquid medium and cultured up to the stationary phase. The generation number at the time was referred to ten. The procedure was repeated to culture the cells up to the 20th generation. The stability of the plasmid was calculated by spreading the diluted the cell suspension on YPD plate and YPD plate containing 40 μg/ml cycloheximide, culturing the plate at 30° C. for 2 days and counting the colonies The results are shown in Table 5.

TABLE 5

Stability of plasmid DNA integrated in the chromosome of ATCC 9950

| Plasmid | Retention rate (%) |
| --- | --- |
| pCLRAPH1 (BglII) | 91.3 |
| pCLRAPH1 (BglII) | 87.8 |
| pCLAPH1 (AflII) | 99.5 |
| pCLAPH1 (AflII) | 98.6 |

It has been confirmed from the result that the DNA fragments inserted in an rDNA locus and in the L41 gene locus are stable.

Example 20
Selection of *Candida utilis* transformants using the G418-resistance as a selectable marker The plasmid pCLRAPH1 contains the mutated L41 gene conferring resistance to cycloheximide and the APT gene conferring resistance to G418 as selectable markers for transformants. Since the APT gene has been confirmed to be expressed by the PGK gene promoter, direct selection of transformants by resistance to G418 was tried.

The plasmid pCLRAPH1 was digested with BglII to form a linear plasmid. The ATCC 9950 strain was transformed with the linearized plasmid by the electric pulse method described in Example 11. Pulse was applied under the condition of electric capacitance of 25 μF, resistance of 1,000Ω, and voltage of 5 KV/cm. The cells were cultured in YPD medium containing 1M sorbitol for 6 hours, and spread on YPD plate containing cycloheximide and on YPD plate containing 150 μg/ml G418.

The results are shown in Table 6.

TABLE 6

Selection of ATCC 9950 transformants with the plasmid pCLRAPH1 by different drug-resistance markers

| Plasmid | G418 | | Cycloheximide | |
|---|---|---|---|---|
| | 1,000 Ω | 800 Ω | 1,000 Ω | 800 Ω |
| pCLRAPH1 (BglII) | 100 | 111 | 7 | 18 |
| -DNA | 0 | — | 0 | — |

* Number of transformants per 0.1 μg DNA;
* The concentration of G418 and cycloheximide was set as 150 μg/ml and 40 μg/ml, respectively.
—: not measured.

It is shown from the result that the number of colonies selected by resistance to G418 is 10 times larger than that selected by resistance to cycloheximide.

Figure 27:
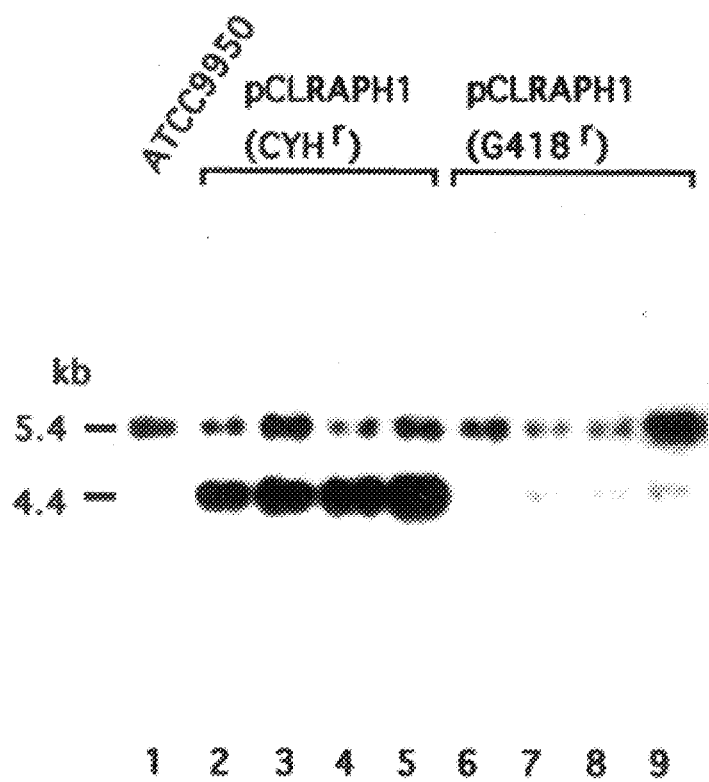
FIG. 27 illustrates the electrophoresis patterns of the results of the Southern blot analysis of the DNA of ATCC 9950 strain transformed with plasmid pCLRAPH1 selected with different drug-resistant markers (CYH$^r$: cycloheximide-resistant; G418$^r$: G418-resistant)

Chromosomal DNA was prepared for 4 colonies selected by resistance to G418 and 4 colonies selected by resistance to cycloheximide. The DNA thus prepared was digested with BglII+NotI, and subjected to Southern analysis with the $^{32}$P-labelled 1.8 kb BamHI-HindIII fragment containing the L41 gene as a probe (FIG. 27). As a result, a 4.4 kb band derive from the plasmid was observed in addition to the 5.4 kb band derived from the endogenous L41 gene. The densities of bands were measured with an Imaging Analyzer BAS 2000 (Fuji Film). The number of copies of the integrated plasmid was calculated by comparing the band derived from the plasmid with the band derived from the endogenous L41 gene (2 copies/cell). It has been indicated that the plasmids were present from four (lane 2) to seven copies (lane 5) in the strains selected by resistance to cycloheximide. It has been also calculated that the plasmids were present in one copy (lanes 6–9) in all of the four strains selected by resistance to G418. These results indicate that strains in which a plurality of plasmids have been integrated can be easily obtained, while the frequency of transformation becomes low when the mutated L41 gene was used as a marker for selecting the transformants.

Furthermore, the plasmid pGKAPH1 was digested with NotI and divided into two fragments. That is, the plasmid was divided into a fragment containing the PGK gene promoter, the APT gene and the PGK gene terminator, and a vector fragment. With these fragments, ATCC 9950 strain was transformed. Pulse was applied under the condition of electric capacitance of 25 μF, resistance of 1,000Ω, and voltage of 5 KV/cm. When transformants were selected on YPD plate containing 200 μg/ml G418, 156 transformants were obtained on the basis of 1 μg of DNA. This indicates that in the *Candida utilis* yeast, the transformation by gene replacement is also observed in addition to the transformation by gene insertion with the plasmid pCLRAPH1 linearized by the digestion with BglII. It is also revealed that transformation by gene replacement happens efficiently, since the frequency of transformation was relatively high.

Example 21
Shortening of PGK gene promoter and identification of minimal functional region The PGK gene promoter used in Examples 17–20 was tried to be shortened for identifying the minimal functional region of the promoter.

First, five fragments containing PGK gene promoters different in length, the APT gene and the PGK gene terminator were obtained with use of the restriction enzyme sites in the PGK gene promoter fragment of the plasmid pGKAPH1 described in Example 19. That is, the plasmid pGKAPH1 was digested with NotI, SacI, EcoRI+SacI or PstI+SacI to prepare four fragments. The plasmid pGKAPH1 was digested with SphI, and treated with T4 DNA polymerase to form blunt ends. BamHI linkers (5'CCGGATCCGG3': SEQ ID NO: 22) were added, and digestion with BamHI and NotI was conducted to obtain another fragment.

Figure 28:
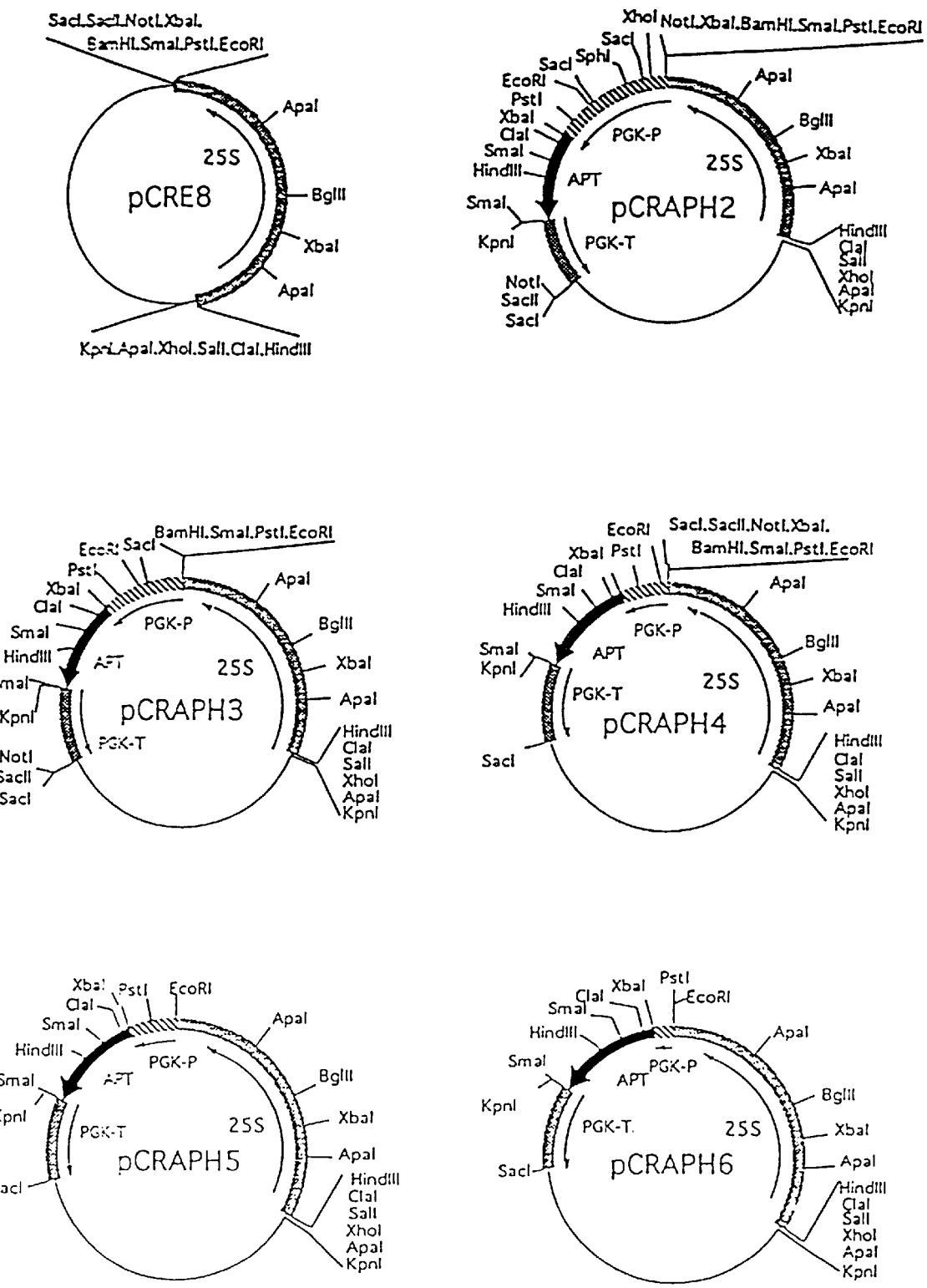
FIG. 28 illustrates the construction of plasmids pCRE8, pCRAPH2, pCRAPH3, pCRAPH4, pCRAPH5 and pCRAPH6.

Of the 0.7 kb and 5.8 kb fragments obtained by digesting the plasmid pCRE2 described in Example 5 with HindIII, the 5.8 kb fragment was recyclized by ligation to form a plasmid pCRE8 (FIG. 28). The plasmid pCRE8 was digested with NotI, BamHI+NotI, SacI, EcoRI+SacI or PstI+SacI, ligated with the above described fragments to construct plasmids pCRAPH2, pCRAPH3, pCRAPH4, pCRAPH5 and pCRAPH6 (FIG. 28). The PGK gene promoter fragment contained in each of the plasmid had a length of 1.35 kb in pCRAPH2, 0.83 kb in pCRAPH3, 0.46 kb in pCRAPH4, 0.40 kb in pCRAPH5 and 0.16 kb in pCRAPH6.

After each of the plasmids pCRAPH2, 3, 4, 5 and 6 thus constructed was linearized by digestion with BagIII, they were used for transformation of the ATCC 9950 strain according to the electric pulse method described in Example 11. Pulse was applied under the condition of electric capacitance of 25 μF, resistance of 1,000Ω, and voltage of 5 KV/cm.

Transformants were selected on a YPD plate containing 200 μg/ml G418. When the plasmids pCRAPH2, pCRAPH3, pCRAPH4 and pCRAPH5 were used, about 300 transformants were obtained on the basis of 1 μg of DNA with each plasmid. However, no transformant was obtained with the plasmid CRAPH6. This indicates that the fragment containing the region from the nucleotide immediately in front of the initiation codon ATG of the PGK gene to the PstI site at 169 bp upstream of 5' end has no function as a transcriptional promoter, but the fragment containing up to the EcoRI site at 401 bp upstream and further longer region has a function as a transcriptional promoter. Therefore, in the 1346 bp sequence containing the PGK gene promoter shown in FIG. 3, the 401 bp sequence from the 946th EcoRI site to the 1346th nucleotide immediately in front of ATG contains a sequence required for the promoter function.

Figure 29:
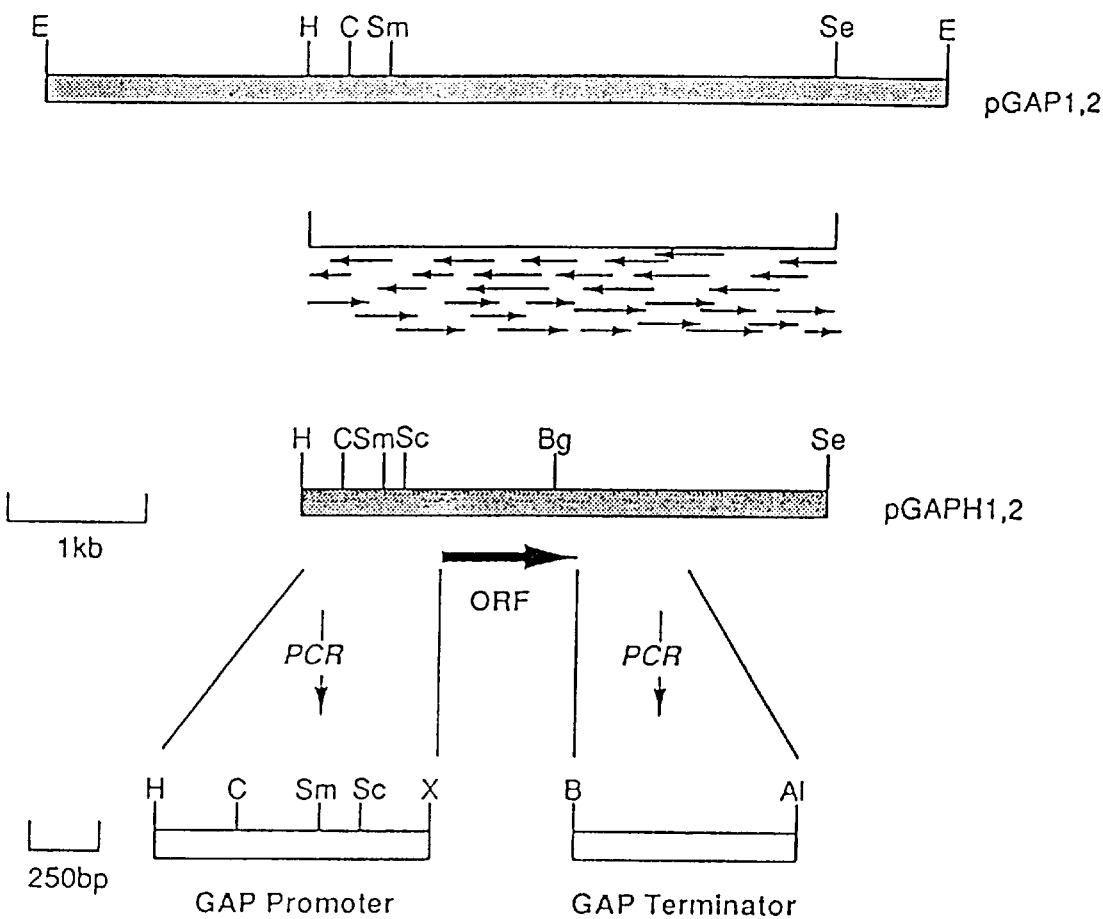
FIG. 29 illustrates the restriction enzyme maps of the plasmids containing glyceraldehyde-3-phosphate dehydrogenase (GAP) gene, the strategy for determining the DNA sequence, and the process for obtaining the promoter and terminator fragments with PCR.

Example 22
Cloning of the glyceraldehyde-3-phosphate dehydrogenase (GAP) gene and sequencing the DNA sequence of a DNA fragment containing the GAP gene The cloning of glyceraldehyde-3-phosphate dehydrogenase (GAP) gene in *Candida utilis* was conducted with the genomic DNA library of *Candida utilis* constructed in Example 2 as a DNA library by the hybridization method with a known GAP gene of the other organisms as a probe. Filters having adsorbed phase DNA of about 20,000 plaques of the above described library thereon were prepared according to the method described in Molecular Cloning, 2nd edition, p. 2, 95–121, Cold Spring Harbor Laboratory (1989). On the other hand, an about 1 kb AsuII-AflIII fragment was cut out from a derivative plasmid of pUC18 which retains a 2.1 kb HindIII fragment containing the GAP gene of *Saccharomyces cerevisiae* (Yamano et al., Journal of Biotechnology, 32, 165–171 (1994)) as a fragment comprising almost of the GAP gene. The fragment was $^{32}$P-labelled, and hybridization was conducted with the labelled fragment as a probe. Three positive plaques were isolated. A phage DNA prepared from one of these plaques was subcloned and a 6.5 kb EcoRI fragment contained in the phage DNA was isolated. The fragment was then inserted in the EcoRI site of the plasmid vector pBluescript IISK+ to construct plasmids pGAP1 and 2 (FIGS. 29).

The isolated 6.5 kb EcoRI fragment was digested with restriction enzymes HindIII, ClaI, SmaI or SpeI alone or in combination, and Southern hybridization was conducted on the resulting fragments with the GAP gene of *Saccharomyces cerevisiae* as a probe. Strong hybridization was observed with the 3.8 kb HindIII-SpeI fragment. The 3.8 kb HindIII-SpeI fragment was inserted between the sites of HindIII and SpeI of plasmid vectors pBluescript IISK+ or pBluescript IIKS+ to prepare plasmids pGAP1 and pGAP2, respectively. Deletion mutants at the restriction enzyme sites such as HindIII, ClaI or SmaI of these plasmids were prepared, and continuous deletion mutants were prepared with ExoIII and mung bean nuclease in order to prepare plasmids having a variety of deletion mutations and the sequence of the 3749 bp HindIII-SpeI fragment was determined (FIG. 29).

When the expected structural gene region was analyzed, a 1005 bp open reading frame was observed. With respect to the amino acid sequence of a gene product deduced from the frame, homology to the GAP gene product of *Saccharomyces cerevisiae* was examined. These sequences showed 79.6% of homology to each other, so that the isolated gene was concluded to be the GAP gene of *Candida utilis*. Further, the fragment contains a 975 bp sequence upstream of the initiation codon and a 1769 bp sequence downstream of the termination codon as a regulatory region. The 975 bp sequence ranging from the HindIII site to immediately in front of the initiation codon ATG which is anticipated to contain the transcriptional promoter is shown in FIG. 30. Further, the 802 bp sequence ranging from immediately behind the termination codon TAA to the AflIII site which is anticipated to contain the transcriptional terminator is shown in FIG. 31.

Example 23

Construction of expression vectors with the promoter and terminator of the GAP gene DNA fragments containing either of the promoter or the terminator were obtained from the GAP gene regulatory regions of *Candida utilis* by the PCR method (FIG. 29).

As the promoter, a fragment ranging from the HindIII site to immediately in front of the initiation codon ATG was obtained with the plasmid pGAP1 as a template. As the primers, the two sequences:

5'-CCAAGCTTACAGCGAGCACTCAAATCT-
    GCCC-3' (SEQ ID NO: 23), and

5'-CCTCTAGATATGTTGTTTGTAAGTGTGTTTT-
    GTATC-3' (SEQ ID NO: 24)

were used. The promoter was synthesized to have the XbaI site which was located immediately in front of the initiation codon at the 3' downstream side.

Further, as the terminator, a fragment from immediately after the termination codon to the SpeI site was obtained from the plasmid pGAP1 as the template. As the primers, the sequences:

5'-GGGATCCATTGTATGACTTTTATTTAT-
    GGG-3' (SEQ ID NO: 25), and

5'-GGACTAGTGAGATGACTCTAGGCATC-
    TTCT-3' (SEQ ID NO: 26)

were used. The terminator was synthesized to have the BamHI site which was immediately after the termination codon at the 5' side.

The PCR process was conducted 30 cycles with a Pfu DNA polymerase (Stratagene). The promoter fragment synthesized by the PCR process was digested with HindIII and XbaI, inserted between the sites of HindIII and XbaI of a pUC19 vector to construct a plasmid pUGpro (FIG. 32). On the other hand, the terminator fragment was digested at the AflIII site of the about 0.8 kb downstream of the termination codon, treated with Klenow enzyme to form blunt ends, and digested with BamHI. The 0.8 kb fragment thus obtained was inserted between the BamHI and SmaI sites of the pUC19 vector to construct a plasmid pUGter (FIG. 32).

After the EcoRI site at the downstream end of the GAP terminator of the plasmid pUGter was treated with Klenow enzyme to form blunt ends, NotI linkers (5' AGCGGC-CGCT3': SEQ ID NO: 18) were isolated to construct a plasmid pUGterN. Further, a 0.95 kb GAP promoter fragment was cut out from the plasmid pUGpro with HindIII and XbaI, and inserted between the sites of HindIII and XbaI of the pUGterN to construct an expression plasmid pGAPPT1. Moreover, the HindIII site at the upstream end of the promoter was treated with Klenow enzyme to form blunt ends, and ligated to NotI linkers (5'AGCGGCCGCT3': SEQ ID NO: 18) to construct a plasmid pGAPPT2 (FIG. 32).

In order to confirm that the expression plasmid pGAPPT2 thus constructed functions practically in *Candida utilis*, a 1.1 kb APT gene fragment cut out with XbaI and BglII from the plasmid pAPH2 described in Example 19 was inserted between the sites of XbaI and BamHI of the plasmid pGAPPT2 to construct a plasmid pGAPAPH1 (FIG. 32).

After the plasmid pGAPAPH1 thus constructed was digested with NotI, it was used for transformation of the ATCC 9950 strain by the electric pulse method under the pulse condition of electric capacitance of 25 μF, resistance of 1,000Ω, and voltage of 5 KV/cm. Transformants were selected on a YPD plate containing 200 μg/ml G418. About 40 transformants were obtained with 0.1 μg of DNA. This indicated that the promoter and terminator of the GAP gene were active.

Example 24

Cloning of the plasma membrane proton ATPase (PMA) gene and sequencing the DNA sequence of a DNA fragment containing the PMA gene Cloning of the plasma membrane proton ATPase (PMA) gene in *Candida utilis* was conducted by the hybridization method using the genomic DNA library of *Candida utilis* constructed in Example 2 and a part of the known PMA gene of the other organisms as a probe. Filters having adsorbed phase DNA of about 20,000 plaques of the above gene library thereon were prepared according to the method described in Molecular Cloning, 2nd edition, p. 2, 95–121, Cold Spring Harbor Laboratory (1989). An about 1 kb region corresponding to +1–+1027 (A of the initiation codon ATG is referred to as +1) of the 5' end of a PMA1 structural gene was amplified with the two primers:

5'-ATGACTGATACATCATCCTC-
    TTCATC-3' (SEQ ID NO: 27), and

5'-TAACGACAGCTGGCAAACC-
GACTGGGAC-3' (SEQ ID NO: 28)

which were synthesized from the DNA sequence of PMA1 gene of *Saccharomyces cerevisiae* (Serrano et al. Nature 319, 689–693(1986)) with the chromosomal DNA of the *Saccharomyces cerevisiae* AH22 strain as the template according to the PCR method. The chromosomal DNA was prepared according to the method described in Methods in Yeast Genetics—A Laboratory Course Manual—Rose, M. D., et al., p. 126–127, Cold Spring Harbor Laboratory Press, NY (1990). The fragment obtained was $^{32}$P-labelled, and hybridization was conducted with the labelled fragment as a probe. As a result, four positive plaques were obtained. For a phage DNA of one of the four positive plaques, the insert DNA was digested with XbaI to isolate four 10 kb, 4 kb, 2.8 kb and 2.6 kb XbaI fragments.

When the four isolated fragments were hybridized with a probe of an about 1 kb fragment of the PMA1 gene of *Saccharomyces cerevisiae* used for screening, the probe was hybridized with a 2.6 kb XbaI fragment. The fragment was inserted in the XbaI site of the plasmid vector pBluescript IISK+ to prepare plasmids pPMAF1 and pPMAF2 which have been inserted in the opposite directions to each other (FIG. 33).

Figure 33:
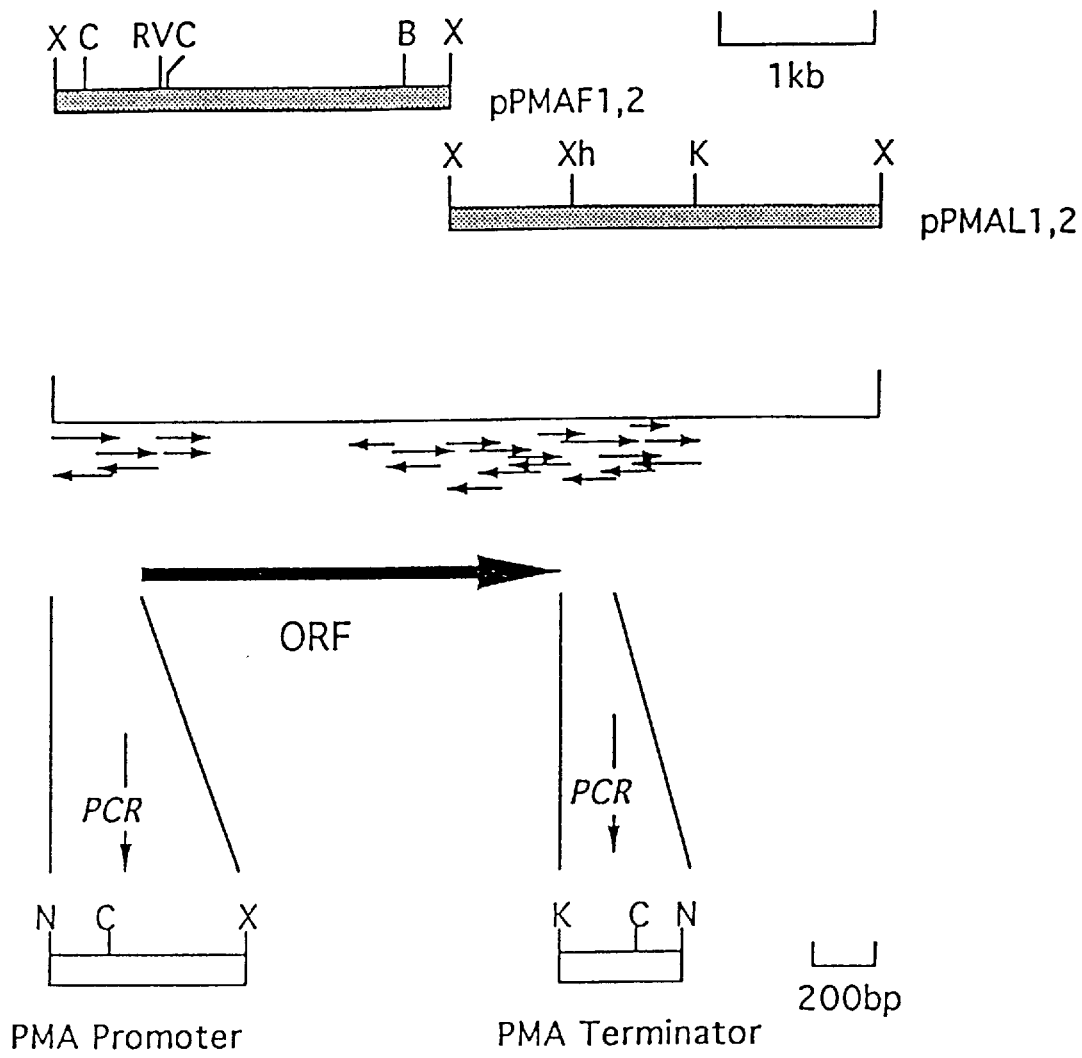
FIG. 33 illustrates the restriction enzyme map of the plasmid containing the plasma membrane proton ATPase (PMA) gene, the strategy for determining the DNA sequence, and the process for obtaining the promoter and terminator fragments with PCR.

From these plasmids, deletion mutants at the restriction enzyme sites such as BamHI, ClaI or EcoRI of these plasmids were prepared, and deletion mutants were prepared with exonuclease III and mung bean nuclease in order to prepare plasmids having a variety of deletion mutations and to determine the DNA sequences of about 1 kb from the both ends (FIG. 33). When the expected structural gene region was analyzed, a 352 bp open reading frame which showed about 50% of homology to the 5' terminal region of the PMA1 structural gene of *Saccharomyces cerevisiae* was observed within about 1 kb sequence containing the region from the XbaI site to the EcoRV site of the left side in FIG. 33. Within about 0.8 kb sequence containing the region from the XbaI site at the other side to inside including the BamHI site, a 754 bp open reading frame which shows 70% of homology to the range from +1292 to +2046 (A of the initiation codon ATG is referred to as +1) of the PMA1 gene of *Saccharomyces cerevisiae* was observed. It was judged from this result that the isolated gene is the PMA gene of *Candida utilis*. Further, the 2.6 kb XbaI fragment contained a 599 bp sequence upstream the initiation codon ATG. The sequence of the 599 bp fragment which is expected to contain the transcriptional promoter is shown in FIG. 34.

As for the transcriptional terminator, the remaining three fragments cut out from the same phage DNA with XbaI (10 kb, 4 kb and 2.8 kb) were subcloned, and their DNA sequences were determined from the both terminal sides to examine their homology to the region of the 3' side of the PMA1 gene of *Saccharomyces cerevisiae*. It has been revealed that a region which shows high homology to the 3' terminal side of the PMA1 gene is present at the one side of the 2.8 kb XbaI fragment. The XbaI fragment was inserted in the XbaI site of the plasmid vector pBluescriptIISK+ to prepare plasmids pPMAL1 and pPMAL2 in which the fragment was inserted in opposite direction to each other (FIG. 33). Plasmids having a variety of deletion mutations were prepared from these plasmids by digestion with KpnI or with use of exonuclease III and mung bean nuclease, and the 1.9 kb DNA sequence from the XbaI site to the KpnI site was determined (FIG. 33). This DNA sequence comprises a 717 bp open reading frame which has a homology of about 82% to the range from +2041 to +2757 (A of the initiation codon ATG is referred to as +1) of the PMA1 gene of *Saccharomyces cerevisiae* and a 188 bp sequence downstream the termination codon TAA. The 1188 bp sequence from immediately after the termination codon TAA to the KpnI site which is expected to contain the transcriptional terminator is shown in FIG. 35.

Example 25

Construction of an expression vector with the promoter and terminator of the PMA gene First, DNA fragments containing the promoter or the terminator were obtained from the PMA gene regulatory regions of *Candida utilis* by the PCR method (FIG. 33).

As the promoter, a fragment ranging from the location at 20 bp downstream of the XbaI site to immediately in front of the initiation codon ATG was obtained with the plasmid pPMAF1 as a template. The two DNA sequences:

5'-GGCGGCCCCAATTAACCCTCACTAAAGGG-
AACGA-3' (SEQ ID NO: 29) and

5'-TTCTAGACTATATCAATGGTTAGTATCA-
CGTG-3' (SEQ ID NO: 30)

were used as the primers. The promoter was synthesized to have the NotI site which was located at the 5' upstream end and the XbaI site which was located at immediately in front of the 3' downstream initiation codon.

As the terminator, a fragment ranging from immediately after the termination codon TAA to 403 bp downstream the termination codon with the plasmid pMAL1 as a template. The DNA sequences:

5'-CCGGTACCTAAGCCGCTAATA-
CCCC-3' (SEQ ID NO: 31) and

5'-GGGCGGCCGCACTCGCTGATC-
GAAA-3' (SEQ ID NO:32)

were used as the primers. The terminator was synthesized to have the KpnI site which was located immediately after the termination codon at the 5' upstream side and the NotI site which was located at the 3' downstream end.

The PCR process was conducted 30 cycles with Pfu DNA polymerase (Stratagene). The promoter fragment synthesized by the PCR process was digested with NotI and XbaI, inserted between the NotI and XbaI sites of pBluescriptIISK+ vector to construct a plasmid pBMpro. On the other hand, the terminator fragment was inserted between the KpnI and NotI sites of the pBluescriptIISK+ to construct a plasmid pBMter. The 0.4 kb KpnI-NotI fragment obtained from the plasmid pBMter was inserted between the sites of KpnI and NotI of the plasmid pUC19N which was constructed by subjecting the EcoRI site of the plasmid pUC19 to the Klenow enzyme treatment and ligating NotI linkers (5' AGCGGCCGCT 3': SEQ ID NO: 18) to construct a plasmid pUMter (FIG. 36).

The 0.4 kb terminator fragment obtained by digesting the plasmid pUMter with XbaI and NotI and the 0.65 kb promoter fragment obtained by digesting the plasmid pBMpro with NotI and XbaI were ligated with the 2.9 kb fragment obtained by digesting the plasmid pPGKPT5 constructed in Example 4 with NotI to construct a plasmid pMAPH1 (FIG. 1).

Figure 36:
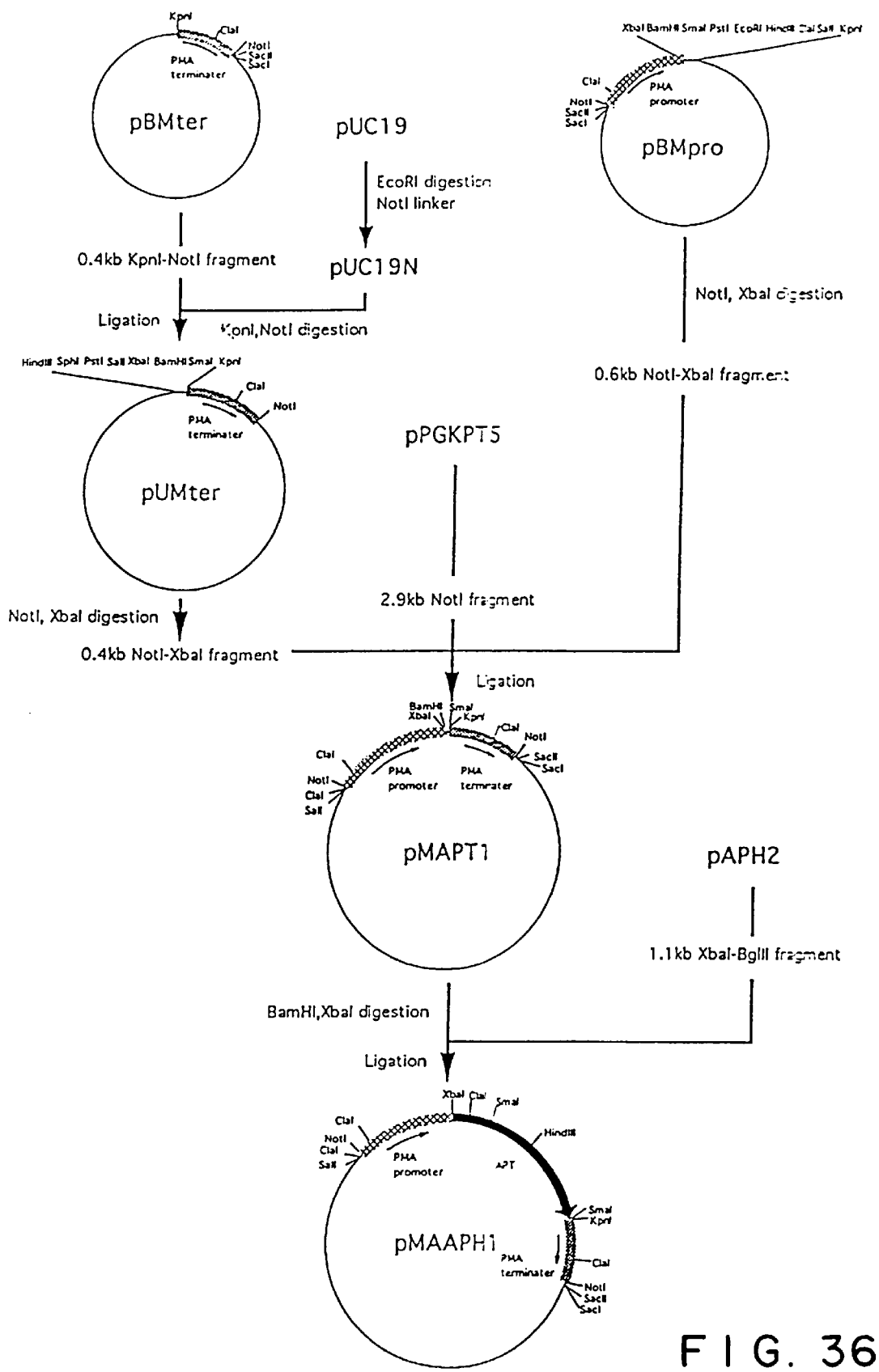
FIG. 36 illustrates the construction of expression vector plasmids with the PMA gene promoter and terminator.

In order to confirm that the expression plasmid pMAPH1 thus constructed functions practically in *Candida utilis*, the 1.1 kb APT gene fragment cut out with XbaI and BglII from the plasmid pAPH2 described in Example 19 was inserted between the sites of XbaI and BamHI of the plasmid pMAPH1 to construct a plasmid pMAAPH1 (FIG. 36).

After the plasmid pMAAPH1 thus constructed was digested with NotI, it was used for transformation of the ATCC 9950 strain by the electric pulse method under the pulse condition of electric capacitance of 25 µF, resistance of 1,000Ω, and voltage of 5 KV/cm.

Transformants were selected on a YPD plate containing 200 µg/ml G418. About 40 transformants were obtained with 0.1 µg of DNA. This indicates that the promoter and terminator of the GAP gene were active.

Example 26
Cloning of DNA fragments containing autonomously replicating sequences (ARS)

The 3.3 kb NotI fragment containing the PGK gene promoter and the PGK gene terminator was cut out from the plasmid pGKAPH1 constructed in Example 19, and inserted into the NotI site of the plasmid pBluescripIISK– (Stratagene) to construct a plasmid pGKAPH2 (FIG. 37). Then, 200 ng of the plasmid pGKAPH2 having been digested with BamHI and dephosphorylated and 200 ng of 3–7 kb fragments digested partially with Sau3AI of the genomic DNA of the Candida utilis ATCC 9950 strain obtained in Example 2 were ligated with T4 DNA ligase. E. coli DH5 was transformed with the DNA solution, and plasmid DNA mixtures were extracted from about 30,000 transformants obtained from the genomic DNA library. The ATCC 9950 strain was transformed with 3 µg of the DNA prepared from the library according to the electric pulse method described in Example 11 under the 4 conditions of an electric capacitance of 25 µF, a resistance of 800Ω or 1,000Ω and a voltage of 3.75 KV/cm or 5 KV/cm. Thus, seven cycloheximide-resistant colonies were obtained. These resistant strains were cultured in YPD medium containing 400 µg/ml of G418. Total DNA was prepared from cells to transform E. coli DH5. The chromosomal DNA of yeast was prepared according to the method described in Methods in Yeast Genetics—A Laboratory Course Manual—Rose, M. D. et al., p. 131–132, Cold Spring Harbor Laboratory Press, NY. Digestion of seven plasmid DNA (pCARS1, pCARS4, pARS5, pCARS6, pCARS7, pCARS8 and pCARS10) collected from E. coli with various restriction enzymes revealed that either of these plasmid DNA comprises 5–7 kb inserts. In addition, when the ATCC 9950 strain was transformed with the plasmid DNA by the electric pulse method, G418-resistant transformants were obtained for either of the plasmid DNA. It was confirmed from this result that DNA sequences having autonomous replicability have been cloned in these plasmids. By the analysis with a variety of restriction enzyme digestions that pCARS7 and pCARS8 of these plasmids comprise the same insert. These results indicates that six DNA fragments having autonomous replicability in the yeast Candida utilis have been cloned.

Further, a genomic DNA library of the yeast Candida utilis was prepared with the plasmid pCLBS10 (FIG. 15) described in Example 9 as a vector. The yeast Candida utilis was transformed with the library together with the library constructed on the plasmid pGKAPH2. However, no cycloheximide-resistant transformant was obtained. This indicates that as a feature of the ARS of Candida utilis, the number of copies of the plasmid containing it is small per cell, and the transformants cannot be selected when the ARS is used with a cycloheximide-resistance L41 gene which requires several copies for selecting a transformant.

Example 27
Shortening of the DNA fragments containing an autonomously replicating sequences (ARS)

Three plasmids (pCARS5, pCARS6 and pCARS7) which have successfully transformed the yeast Candida utilis at a high frequency among the seven plasmids in which autonomously replicating DNA sequence have been cloned in Example 26 were further analyzed in detail.

The frequency of transformation of yeast with these three plasmids was examined with the BglII-digested DNA of the chromosome-integrated plasmid pCLRAPH1 prepared in Example 19 as a control. The ATCC 9950 strain was transformed with 0.1 µg of DNA under the pulse condition of an electric capacitance of 25 µF, a resistance of 1,000Ω and a voltage of 5 KV/cm. The post-pulse culture was carried out for 4 hours. The result is shown in Table 7.

TABLE 7

| Frequencies of transformation with a variety of ARS plasmids | |
|---|---|
| Plasmid | Number of colonies |
| pCARS5 | 16450 |
| pCARS6 | 9500 |
| pCARS7 | 4700 |
| pCLRAPH1 | 400 |

Note 1): Number of transformants per 1 µg of plasmid DNA.
Note 2): pCLRAPH1 was digested with BglII before use.

This indicates that the frequency of transformation which is about 10–40 times higher than that of the integration of DNA with rDNA as a target is obtained with the plasmids containing the ARS.

In addition, these plasmids pCARS5, pCARS6 and pCARS7 were digested with NotI and recyclized with T4 DNA ligase to construct plasmids pCARS50, pCARS60 and pCARS70 from which the 3.3 NotI fragment containing the PGK gene promoter, the APT gene and the PGK gene terminator was deleted. These three new plasmids were examined on the length of their inserts with a variety of restriction enzyme digestion. Thus, all these plasmids had inserts of about 5–6 kb, so that the regions having autonomous replicability was further limited. Each of the plasmids pCARS50, pCARS60 and pCARS70 was partially digested with Sau3AI to collect 1–3.5 kb fragments, which were ligated to the plasmid pGKAPH2 which had been digested with BamHI and dephosphorylated with T4 DNA ligase. E. coli DH5 was transformed with each of the three DNA solutions, and plasmid DNA mixtures were extracted from 2,500–6,000 transformants to prepare DNA libraries. The ATCC 9950 strain was transformed again with 5 µg portions of the DNA according to the electric pulse method described in Example 11 to obtain G418-resistant transformants.

The G418-resistant colonies thus obtained had a variety of sizes, and five transformants of each of the three libraries which had formed a relatively large colony was further cultured in YPD medium containing 200 µg/ml of G418. Total DNAs were prepared from cells thus obtained, and E. coli DH5 was transformed with the DNA. No transformant of E. coli was obtained with some of the G418-resistant strains. Moreover, when the ATCC 9950 strain was transformed again with these plasmids collected according to the electric pulse method described in Example 11, some of these plasmids were excluded as they showed an extensively low frequency of transformation as compared with the original plasmids pCARS5, pCARS6 and pCARS7. Finally, a plasmid containing a shortened DNA fragment and having a transformation frequency similar to that of the parent plasmid was obtained from each of pCARS50, pCARS60 and pCARS70. The plasmid derived from pCARS50 was referred to as pCARS5-2, the one derived from pCARS60 as pCARS6-2 and the one derived from pCARS70 as pCARS7-

49

Figure 38:
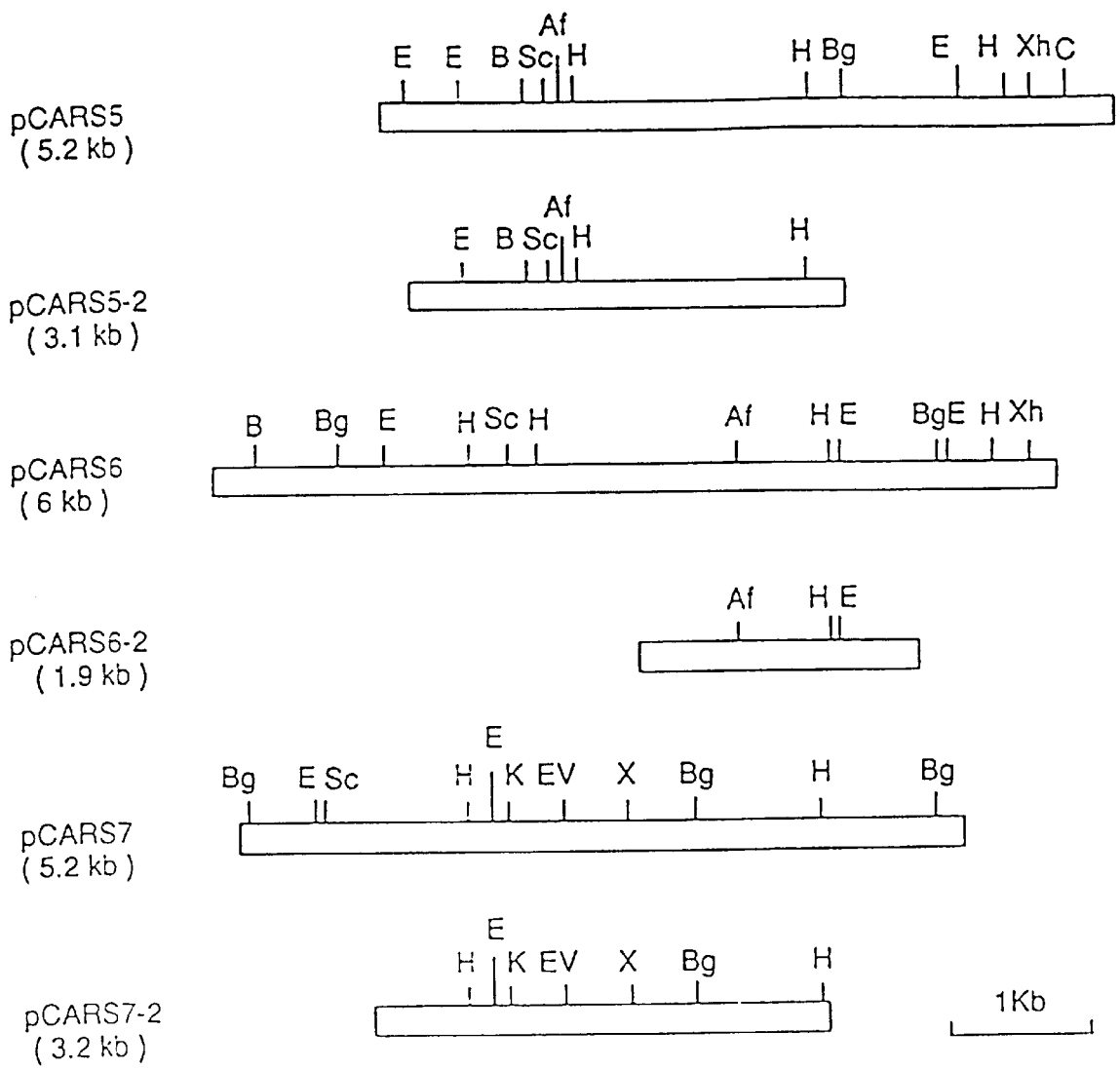
FIG. 38 illustrates the restriction enzyme maps of six plasmid insertion DNA fragments containing ARS.

2, respectively. The restriction enzyme maps of the chromosomal DNA fragments containing autonomously replicating sequences in these six plasmids thus obtained are shown in FIG. 38.

Plasmids containing further shortened DNA fragments were constructed from the three plasmids pCARS5-2, pCARS6-2 and pCARS7-2 which have the shortened chromosomal DNA fragments to examine their transformation frequencies. When the partial DNA sequences of some of the plasmids constructed in this process were determined, the about 700 bp region in the left side of the BglII site in pCARS5 in FIG. 38 showed a homology of 90% or more to the about 700 bp region in the left side of the EcoRI site in pCARS6-2. This results suggested that the insertion DNA fragments of pCARS5 and pCARS6 are derived respectively from the homologous chromosomes or repetitive sequences, though they have different restriction enzyme maps. Therefore, the following analysis was conducted on the insertion DNA fragment of pCARS6 and pCARS7. The autonomously replicating sequence contained in pCARS6 was referred to as CUARS1, and the autonomously replicating sequence contained in pCARS7 was referred to as CUARS2, respectively.

Example 28

Shortening of DNA fragments inserted in pCARS6 and pCARS7 and transformation frequency and plasmid stability (1) Shortening of the DNA fragment inserted in pCARS6 and transformation frequency The DNA fragment cloned in the plasmid pCARS6-2, which was partially digested with Sau3AI, had a size of about 1.9 kb. Thus, three plasmids containing parts of the inserted fragment of pCARS6-2 were constructed in order to further limit the autonomously replicable region. These plasmids were constructed by the following procedure.

The 3.3 kb NotI fragment containing the APT gene expression cassette was removed from pCARS6-2 to construct pCARS6-20. The plasmid pCARS6-20 was digested with AflII and XbaI, treated with Klenow enzyme to form blunt ends, and recyclized with T4 DNA ligase to construct a plasmid pCARS6-210. The plasmid was ligated with a 2.3 kb NotI fragment containing the APT gene expression cassette with a shortened PGK gene promoter which was cut out from the plasmid pGKAPH3 to construct plasmid pCARS6-12. The plasmid pGKAPH3 was constructed by treating the EcoRI site in the promoter fragment of the plasmid pGKAPH1 constructed in Example 19 with Klenow enzyme to form blunt ends, to which NotI linkers (5'AGCGGCCGCT3': SEQ ID NO: 18) were ligated. Each of pCARS6-20 and pCARS6-21 was digested with HindIII, recyclized with T4 DNA ligase, and then ligated with the 2.3 kb NotI fragment containing the APT gene expression cassette with the shortened PGK gene promoter in the same manner as above to construct plasmids pCARS6-22 and pCARS6-23, respectively. The restriction enzyme maps of the insertion DNA fragments contained in these five plasmids are shown in FIG. 39.

The ATCC 9950 strain was transformed with each of the plasmids thus constructed according to the electric pulse method described in Example 11 with 1 μg of DNA under the pulse condition of an electric capacitance of 25 μF, a resistance of 1,000Ω and a voltage of 5 KV/cm. The post-pulse culture was carried out for 4 hours. The result is shown in Table 8.

50

TABLE 8

Transformation frequencies and stabilities of a variety of plasmids derived from pCARS6

Number of transformants per 1 μg of plasmid DNA

| Plasmid | Number of colonies | (%) |
| --- | --- | --- |
| pCARS6 | 1093 | (100) |
| pCARS6-2 | 710 | (65) |
| pCARS6-21 | 137 | (13) |
| pCARS6-22 | 253 | (23) |
| pCARS6-23 | 25 | (2) |

Note 1: Data express the average values of double experimental runs.

Stability of plasmid

| Plasmid | % |
| --- | --- |
| pCARS6 | 21.4 |
| pCARS6-2 | 31.9 |
| pCARS6-21 | 29.9 |
| pCARS6-22 | 11.0 |
| pCARS6-23 | 3.9 |

Note: Generation number is between 2.5–3.5 generation.

The stability of each plasmid in yeast was examined according to the following procedure. The G418-resistant colonies thus obtained were inoculated in 4 ml of a YPD medium and cultured with shaking at 30° C. for 8 hours. The cells were spread on YPD plate and a YPD plate containing G418. Numbers of colonies were compared with each other after culturing for 2 days for calculating the retention rate of the plasmid. The results are shown in Table 8. The absorbance of the culture showed that the cells have divided 2.5–3.5 times. It was also revealed from the result that of the plasmids pCARS6-21 and pCARS6-22 in which the insertion DNA fragment of pCARS6-2 had been shortened from the both sides showed great decrease in transformation frequency, although the pCARS6-21 showed the stability similar to that of pCARS6-2. Also, with respect to the CARS6-23 in which the insertion DNA fragment had been shortened to 0.6 kb, transformation frequency was further decreased to 1/50 as compared with the transformation frequency with pCARS6. These results indicate that CUARS1 contained in pCARS6 is difficult to be shortened than the about 1.9 kb DNA fragment of pCARS6-2.

(2) Shortening of pCARS7 insertion DNA fragment and transformation frequency

The DNA fragment cloned in the plasmid pCARS7-2, which was partially digested with Sau3AI, had a size of about 3.5 kb. Thus, in order to further limit the autonomously replicable region, five plasmids containing parts of the pCARS7-2 insertion fragment were constructed according to the following procedure.

From plasmid pCARS7-2, the 3.3 kb NotI fragment containing the APT gene expression cassette was removed to construct plasmid pCARS7-20, which was then digested with XbaI, recyclized with T4 DNA ligase, and ligated to the 2.3 kb NotI fragment containing the APT gene expression cassette to construct pCARS7-4.

In addition, an about 1.8 kb EcoRV-HindIII fragment, an about 1.3 kb XbaI-HindIII fragment, and an about 1.8 kb HindIII-BglII fragment were cut out from pCARS7-20, and ligated to pBluescriptIISK– (Stratagene) digested with wither EcoRV and HindIII, XbaI and HindIII, or HindIII and BamHI, respectively. The 2.3 kb NotI fragment containing the APT gene expression cassette with the shortened PGK gene promoter was ligated with the plasmid to construct pCARS7-6, pCARS7-7, and pCARS7-8. The restriction enzyme maps of the insertion DNA fragments contained in these six plasmids are shown in FIG. 40.

The ATCC 9950 strain was transformed with each of the plasmids thus constructed according to the electric pulse method described in Example 11 with 1 µg of DNA under the pulse condition of an electric capacitance of 25 µF, a resistance of 1,000Ω and a voltage of 5 KV/cm. The post-pulse culture was carried out for 4 hours. The result is shown in Table 9.

TABLE 9

Transformation frequencies and stabilities of a variety of plasmids derived from pCARS7

| Plasmid | Number of transformants per 1 µg of plasmid DNA | |
|---|---|---|
| | Number of colonies | % |
| pCARS7 | 1833 | 100 |
| pCARS7-2 | 1273 | 69 |
| pCARS7-4 | 0 | 0 |
| PCARS7-6 | 598 | 33 |
| pCARS7-7 | *280 | 15 |
| PCARS7-8 | 5 | 0.2 |

Note 1: Data express the average values of double experimental runs.
Note 2: * indicates that colonies have very small sizes.

Stability of plasmid

| Plasmid | % |
|---|---|
| pCARS7 | 23.0 |
| pCARS7-2 | 34.9 |
| pCARS7-6 | 18.6 |
| pCARS7-7 | 11.4 |
| pCARS7-8 | 7.0 |

Note: Generation number is between 2.5–3.5 generation.

The stability of each enzyme in yeast was examined according to the following procedure. The G418-resistant colonies thus obtained were inoculated in 4 ml of a YPD medium and cultured with shaking at 30° C. for 8 hours. The cells were spread on YPD plate and YPD plate containing G418, and numbers of colonies were compared with each other after culturing for 2 days for calculating the retention rate of the plasmid (Table 9). The absorbance of the culture showed that the cells have divided 2.5–3.5 times. These results indicated that the transformation frequencies with the plasmids pCARS7-2 and pCARS7-6 decreased to about 70% and about 30% as compared with that of pCARS7. However, the stability was not so lowered. While the plasmid pCARS7-7 containing a further shortened DNA fragment showed the transformation frequency of ½ as compared with pCARS7-6, it generated colonies very small in size and showed poor stability (Table 9). On the other hand, transformation frequency was poor with pCARS7-8, and no transformant was obtained with pCARS7-4. These results indicate that CUARS2 contained in pCARS7 may be shortened to the 1.8 kb DNA fragment of pCARS7-6, while the transformation frequency decreased.

These two results with respect to the shortening of ARS indicate that a relatively long region is necessary for the ARS of the yeast *Candida utilis* to have an autonomous replicability. This is a very interesting feature, which is different from the fact that the about 200 bp ARS of a yeast of the genus Saccharomyces shows its function (Newlon, C. R and Theis, J. Current Opinion in Genetics and Development, 1993, 3, 752–758).

Example 29
Determination of the DNA sequences of DNA fragments containing the autonomously replicating sequence of pCARS6-2 and pCARS7-6 and Southern analysis (1) Determination of the DNA sequences of DNA fragments containing autonomously replicating sequences The DNA sequence of the DNA fragments containing ARS, CUARS1 and CUARS2, in pCARS6 and pCARS7 were determined. Plasmids having a variety of deletion mutations were prepared by deletion with ExoIII nuclease and mung bean nuclease from the both ends of the insertion DNA fragment of pCARS6-2, as a DNA containing the CUARS1 and the insertion DNA fragment of pCARS7-6 as a DNA containing the CUARS2 in order to determine the DNA sequences. The DNA sequence of the insertion DNA fragment of pCARS6-2 is shown in FIGS. 41 and 42, and the DNA sequence of the insertion DNA fragment of pCARS7-2 is shown in FIGS. 43 and 44. The insertion DNA fragment of pCARS6-2 comprises 1921 bp and has a ratio of A+T to the total bases of 69.5%, and the insertion DNA fragment of pCARS7-2 comprises 1788 bp and has a ratio of A+T to the total bases of 70.8%. It has been thus revealed that either of the DNA fragments have a very high ratio of A+T.

Computerized analysis revealed that as compared with the 11 bp sequence (T/A)TTTA(C/T)(A/G)TTT(T/A) (SEQ ID NO:40) which are commonly observed in ARS (Newlon, C. R. and Theis, J., Current Opinion in Genetics and Development, 1993, 3, 752–758), 9 consensus-like sequences (which are different in one base from the consensus sequence) are present in pCARS6-2 and similar 13 consensus-like sequences are present in pCARS7-6, 5 sequences being overlapped with each other (FIGS. 41–44).

(2) Calculation of number of copies by Southern analysis

Figure 45:
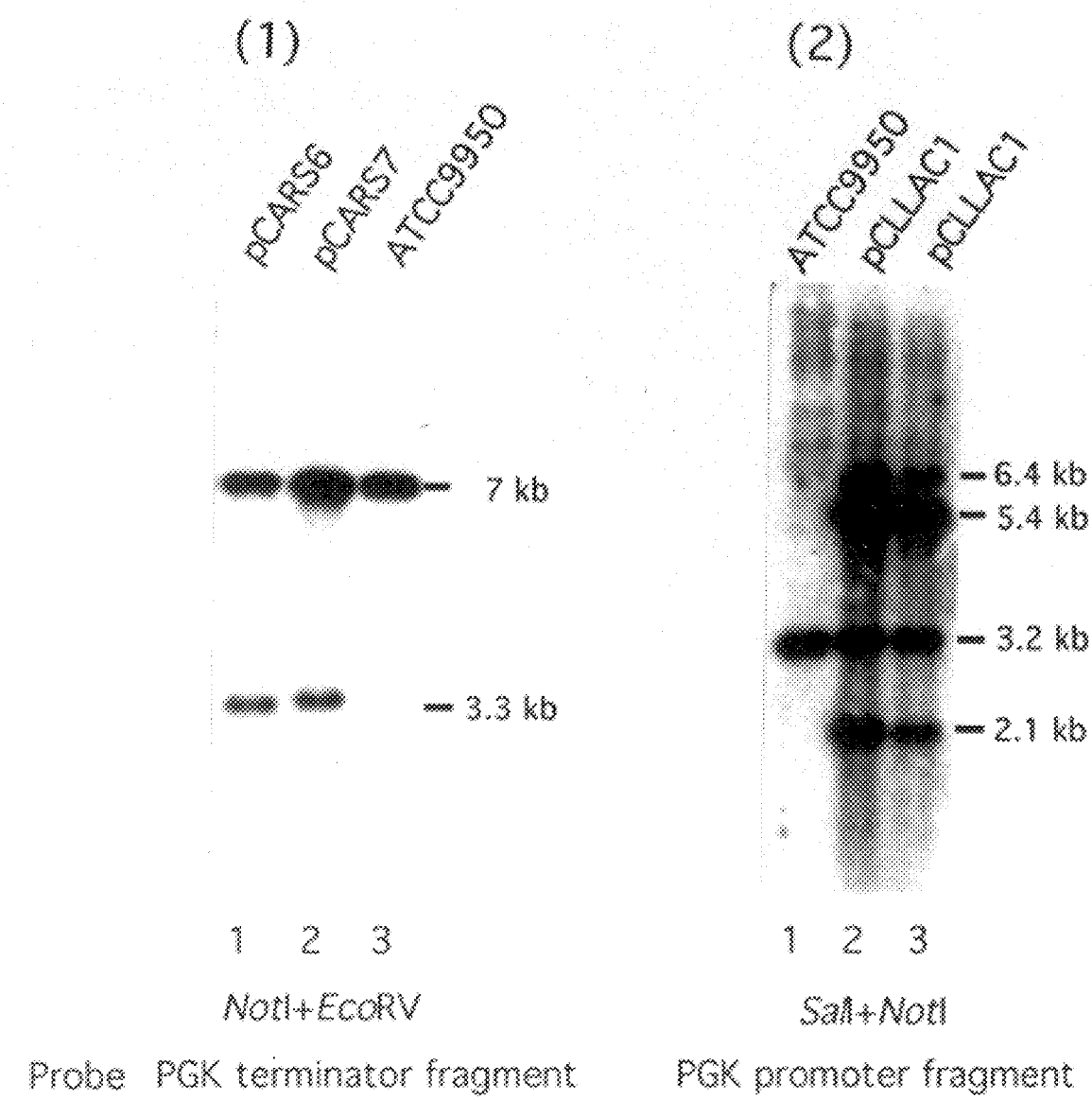
FIGS. 45(1) and 45(2) illustrate the electrophoresis patterns of the results of the Southern blot analysis of the DNA (1) of the ATCC 9950 strain transformed with plasmid pCARS6 or pCARS7, and of the DNA (2) of the ATCC 9950 strain transformed with plasmid pCLAC1.

In order to evaluate the number of copies of the plasmid containing ARS in the cell of the yeast *Candida utilis*, Southern analysis was conducted on the DNA prepared from the yeast *Candida utilis* which had been transformed with pCARS6 or pCARS7 (FIG. 45-1). In addition, since the PGK gene was used as an internal standard for calculating the number of copies, Southern analysis was conducted for calculating the number of copies of the PGK gene (FIG. 45-2).

Southern analysis for calculating the number of copies of the PGK gene was conducted with DNA prepared from 2 strains of the ATCC 9950 transformed with the plasmid pCLLAC1 described in Example 18, which had been digested at the SphI site in the PGK promoter, and with DNA prepared from the parent strain as a control. When the 0.4 kb EcoRI-XbaI fragment containing the PGK promoter cut out from pGKPT4 described in Example 4 was used as a probe for the DNA digested with SalI+NotI, a 3.2 kb band derived from the endogenous PGK gene was observed in the ATCC 9950 strain as the parent strain (FIG. 45-2, lane 1). On the other hand, in the strain in which pCLLAC1 digested with the SphI site in the PGK promoter had been integrated, in addition to this 3.2 kb band, a 5.4 kb band generated by NotI digestion of plural plasmids integrated in tandem, and two bands of 6.4 kb and 2.1 kb generated by disrupting one of the chromosomal PGK genes by the insertion of the plasmids were detected. (lanes 2 and 3). Since these two 6.4 kb and 2.1 kb bands were generated from the NotI site in the plasmid molecule and the SalI site in the PGK gene region at the both sides of the integrated plasmid molecule, the plasmid molecule was revealed to be integrated in the PGK gene locus by homologous recombination.

When the densities of these bands were measured with an Imaging Analyzer (Fuji Film), the 3.2 kb band derived from the endogenous PGK gene and the 6.4 kb and 2.1 kb bands derived from the plasmids at the both ends of the plasmid molecules integrated in the chromosome had almost the same densities in the transformant. Thus, it was indicated that there are 2 copies of the PGK gene per cell, and in the transformants one of the 2 copies was disrupted by the insertion of the plasmid DNA. Furthermore, it was revealed by comparing the densities of the 5.4 kb band due to the tandem integration of the plasmid and the 6.4 kb and 2.1 kb bands, that the integrated plasmid had about 4 copies.

The DNA prepared from ATCC 9950 strains transformed with pCARS6 and pCARS7 were digested with EcoRV+ NotI, and Southern analysis was conducted with the 0.9 kb XbaI-NotI fragment containing the PGK terminator cut out from pGKPT4 described in Example 4 as a probe. The result is shown in FIG. 45-1. In the parent ATCC 9950 strain, an about 7 kb band derived from the endogenous PGK gene was observed (FIG. 45-1, lane 3). In the transformant, a 3.3 kb band derived from the plasmid in addition to the about 7 kb band was observed. By comparing the densities of the 7 kb and the 3.3 kb bands, it was calculated on the assumption that the 7 kb band corresponds to 2 copies of the PGK gene and that copy number of pCARS6 and pCARS7 were 1 (lane 4) and 0.4 (lane 2), respectively. Due to the falling out of the plasmid molecule during cell culture, the number of copies of pCARS7 might be less than 1. It was considered from the result that the plasmid containing CUARS had about 1 copy per cell.

(3) Existence mode of ARS on chromosome

Figure 46:
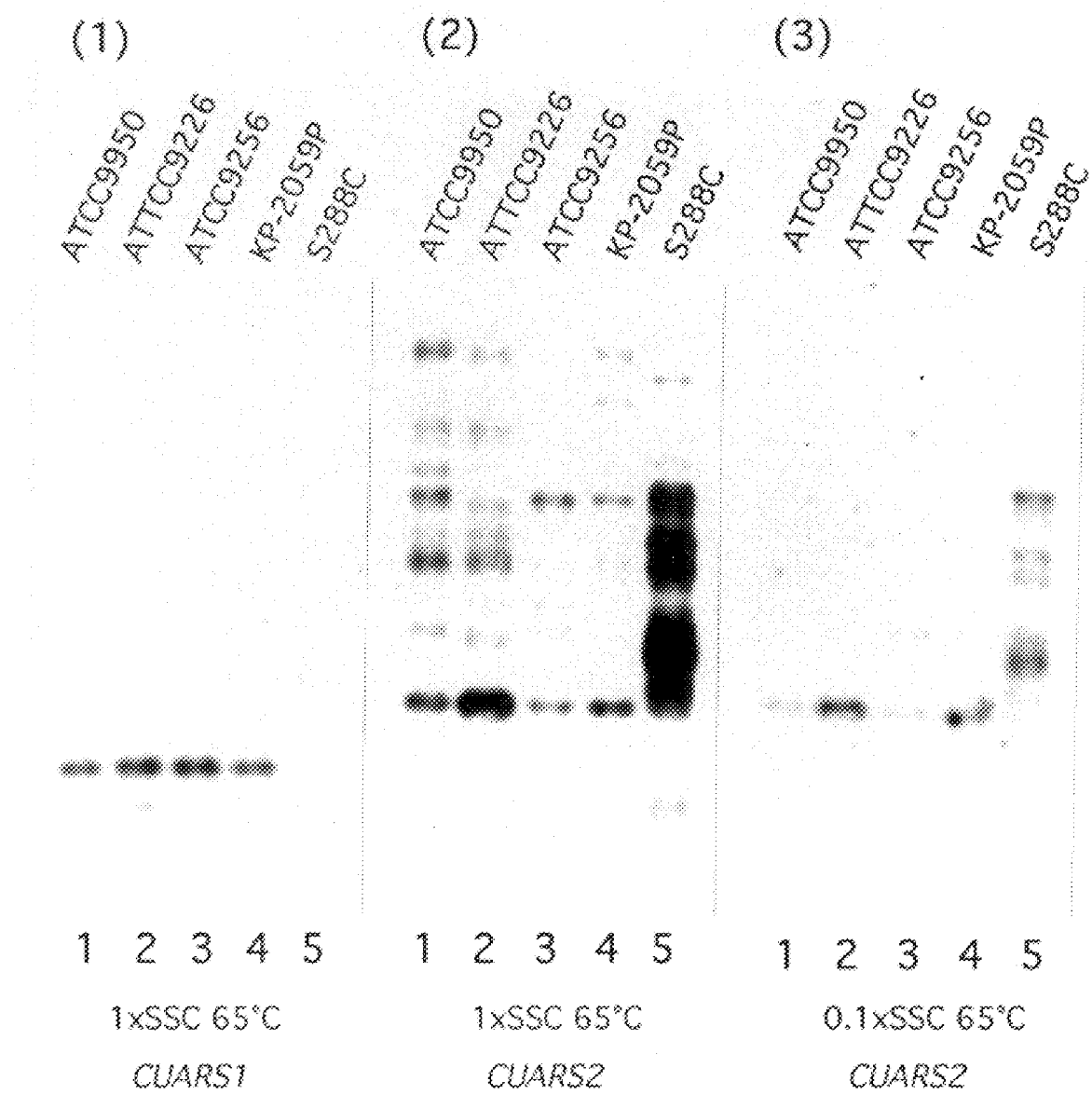
FIGS. 46(1)–46(3) illustrate the electrophoresis patterns of the results of the Southern blot analysis of the DNA of ATCC9950, ATCC9226, ATCC9256, KP-2059P and S288C strains with CUARS1 (1) and CUARS2 {(2) and (3)} as probes.

Southern analysis was conducted on a variety of chromosomal DNA of the HindIII-digested ATCC 9950, 9226, 9256 and KP-2059 strains and *Saccharomyces cerevisiae* S288C strain. With probes: as CUARS1 the 1.3 kb fragment obtained by digesting pCARS6-22 with XbaI and HindIII (FIG. 39); and as CUARS2 the 1.8 kb EcoRV-HindIII fragment of pCARS7-6 (FIG. 40), hybridization was conducted (FIG. 46). With respect to CUARS1, in addition to a main 2 kb band which was expected from the restriction enzyme map of pCARS6, a 1.6 kb band which had the same length as the HindIII fragment expected from the restriction enzyme map of pCARS5 was observed (FIG. 46-1). Further, with respect to CUARS2, in addition to a main 2.5 kb band which was expected from the restriction enzyme map of pCARS7, DNA sequences having a high homology were present in about 10 copies on the chromosome of the yeast *Candida utilis* and also in many copies on the Saccharomyces yeast (FIG. 46-2). It is suggested from the result that CUARS2 may be an extensively preserved sequence. In addition, with a severer washing condition (0.1×SSC, 65° C.), any signals other than the main one were scarcely observed (FIG. 46-2).

Furthermore, in order to examine whether these ARS sequences are derived from chromosomal DNA or not, Southern analysis was conducted on the chromosomal DNA of *Candida utilis* separated by the pulse field gel electrophoresis method. The DNA of the ATCC 9950 strain was separated in seven bands, in which CUARS1 was located at the 6th chromosome from the top and CUARS2 was located at the 3rd chromosome from the top. It was also revealed that the cloned ARS sequences were derived from chromosome. The insertion DNA fragment of pCARS5 was located at the 6th chromosome like CUARS1. As indicated from the sequence analysis described in Example 27, these results supported the possibility that ARS cloned in these pCARS5 and pCARS6 be derived from the homologous chromosomes.

Example 30

Cloning of DNA fragments having promoter activity with use of ARS (1) Construction of promoter cloning vector DNA containing an autonomously replicable sequence was cut out as a 1.9 kb SacI-SmaI fragment from the plasmid pCARS6-20 constructed in Example 28. The fragment was ligated with the plasmid pAPH1 (Example 19), which was digested with EcoRI and treated with Klenow enzyme to form blunt ends, and further digested with SacI to construct a plasmid pPCV1. Further, pPCV1 was digested with BamHI, treated with Klenow enzyme to form blunt ends, and HpaI linkers (5'GTTAAC3') were ligated to construct a plasmid pPCV2 (FIG. 47).

(2) Construction of a library and cloning of DNA fragments having promoter activity Chromosomal DNA of the *Candida utilis* ATCC 9950 strain was partially digested with restriction enzymes RsaI, HaeIII and AluI at the same time. Then, the DNA fragments were subjected to electrophoresis with 1% of agarose gel, and the 0.9–1.8 kb long fragments were collected. The partially digested DNA fragments and the plasmid pPCV2 digested with HpaI and dephosphorylated were ligated with T4 DNA ligase. *E. coli* DH5 was transformed with the DNA solution, and a plasmid DNA mixture was extracted from about 100,000 transformants thus obtained to prepare a genomic DNA library. The ATCC 9950 strain was transformed with the DNA prepared from this library with the electric pulse method under the pulse condition of electric capacitance of 25 $\mu$F, resistance of 1,000$\Omega$, and voltage of 5 KV/cm. DNA was used in an amount of 20–25 $\mu$g per pulse. Transformants were selected on a YPD plate containing 200 $\mu$g/ml G418. Repetitive runs of transformation gave 380 transformants in total with 280 $\mu$g of DNA. Among these transformants, 84 strains in which relatively large colonies were formed were grown on YPD plate containing 1 mg/ml G418. Twelve strains which showed good growth were cultured in YPD medium containing 1 mg/ml G418, and total DNA was prepared from the cells to transform *E. coli* DH5.

It has been revealed by the restriction enzyme digestion that all of the twelve plasmid DNA recovered from *E. coli*, i.e., pPCV1, 3, 9, 14, 19, 33, 51, 55, 57, 62, 64 and 78, contain 0.9–1.8 kb insertion DNA fragments. Further, DNA fragments containing sequences having promoter activity were cut out with XbaI, and ligated to pBluescriptIISK– (Stratagene) to construct plasmids. Partial DNA sequences of the plasmids were determined starting from the both sides of the insertion DNA fragments. It was revealed from the result that pPCV33 and pPCV78, or pPCV14, pPCV51 and pPCV55 have the same DNA fragment. Therefore, nine DNA fragments having promoter activity were finally cloned.

When the ATCC 9950 strain was transformed with nine plasmids pPCV1, 3, 9, 14, 19, 33, 57, 62 and 64 by the electric pulse method, 6,000–10,000 G418-resistant colonies were obtained per 1 $\mu$g of DNA for either of the plasmid DNA. Moreover, 20 clones comprising 2 strains of 10 G418-resistant strains obtained with the 9 plasmids and pCARS6-2 used as a control were cultured in 5 ml of YPD medium overnight, and then separated into single colonies on YPD plate. Ten colonies of each of the twenty clones were cultured on a YPD plate containing G418 to evaluate the retention rate of the plasmids. As a result, while pCARS6-2 had a plasmid retention rate of 5%, all of the other plasmids had an increased retention rate. Among these plasmids, particularly pPCV1, pPCV19 and pPCV64 had a high retention rate in the range of 80–85%. It was thus indicated that the DNA fragment containing a sequence which had a promoter activity thus obtained had a function of increasing the stability of the plasmid.

(3) Determination of the DNA sequence of a DNA fragment having a promoter activity With respect to the insertion DNA fragment of the plasmid pPCV19 among the nine DNA fragments having promoter activity thus obtained, plasmids having a variety of deletion mutations were prepared by deletion with use of ExoIII nuclease and mung bean nuclease to determine the DNA sequence from the both sides of the insertion DNA fragment. The determined DNA sequence of the 1054 bp insertion DNA fragment of pPCV19 are shown in FIG. 48.

Example 31

Construction of a plasmid for expressing hygromycin B-resistance gene and selection of co-transformants of yeast with use of it (1) Construction of a plasmid for expressing hygromycin B-resistance gene and confirmation of its function Hygromycin B phosphotransferase (HPT) gene was obtained by PCR with 2 primers prepared according to the already described DNA sequence of the HPT gene (Gritz, L. and Davis, J., Gene, 25, 179–188 (1983)) using the plasmid pBIB-HYG (Becker, D., Nucl. Acids Res., 18, 203 (1990)) as a template. As the primers, the DNA sequences:

5'-GGTCTAGATATGAAAAAGCC-
TGAAC-3'    (SEQ ID NO: 33) and

Figure 49:
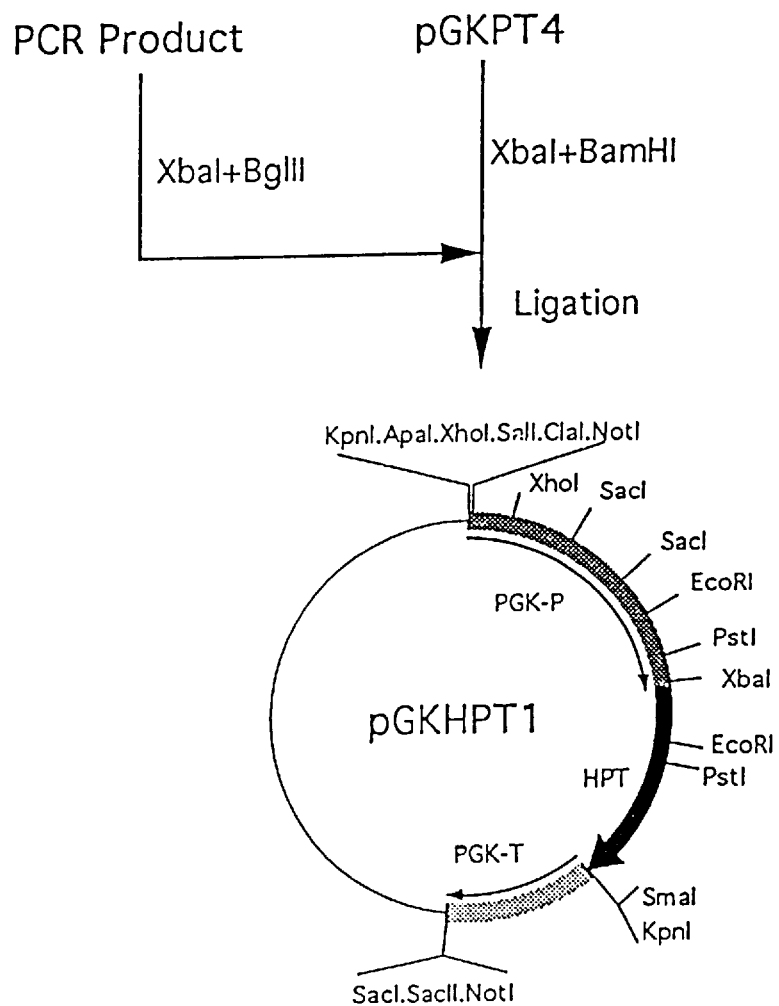
FIG. 49 illustrates the construction of plasmid pGKHPT1.

5'-GGAGATCTATTCCTTTGCCCTCGGA-3'    (SEQ ID NO:34)

were used. The synthesis was conducted to have the XbaI site which was located immediately in front of the initiation codon at the 5' side and the BglII site which was located immediately after the 3' end termination codon. The HPT gene fragment synthesized was digested with XbaI and BglII, inserted between the sites XbaI and BamHI of the expression vector pPGKPT4 (FIG. 4) described in Example 4 to construct a plasmid pGKHPT1 (FIG. 49). The 3.3 kb NotI fragment containing the PGK gene prompter, the HPT gene, and the PGK gene terminator was cut out from the pGKHPT1. The plasmid pAHG1 was constructed by inserting the NotI fragment at the NotI site of the plasmid pPCV14 described in Example 30. In order to confirm whether the constructed HPT gene expression cassette functions or not, the ATCC 9950 strain was transformed with plasmid pAHG1 by the electric pulse method described in Example 11. Transformants selected with resistance to G418 grew in a YPD liquid medium containing 200, 400 and 800 µg/ml of hygromycin B, while wild strain used as a control did not grow in any media and showed resistance to hygromycin B.

After the plasmid pGKHPT1 was divided into a fragment containing the PGK gene promoter, the HPT gene and the PGK gene terminator, and a vector fragment by digestion with NotI, they were used for the transformation of the ATCC 9950 strain. Transformation was conducted by the electric pulse method described in Example 11, and transformants were selected on a YPD plate containing 800 µg/ml of hygromycin B. As a result, 168 hygromycin B-resistant colonies were obtained per 1 µg DNA. This is almost the same as the transformation frequency with the NotI digested plasmid pGKAPH1 used as a control, 156 colonies per 1 µg DNA. Thus, this result indicates that the hygromycin B-resistance gene can be used in the direct selection of transformants of Candida utilis just like the G418-resistance gene.

(2) Co-transformation of yeast 0.1 µg of the plasmid pPCV64 containing ARS obtained in Example 30 and 1 µg or 10 µg of the plasmid pPGKHPT1 divided by NotI digestion into the fragment containing the PGK gene promoter, the HPT gene, and the PGK gene terminator and the vector fragment by NotI digestion were mixed, and used for the transformation of the ATCC 9950 strain by the electric pulse method described in Example 11.

Pulse was applied at the condition of an electric capacitance of 25 µF, a resistance of 600, 800 or 1,000Ω, and voltage of 3.75 or 5 KV/cm, with 6 pulse conditions for the 2 DNA mixtures. Transformants were selected on a YPD plate containing 200 µg/ml G418, and about 2,000–7,000 of transformants were obtained under each condition with 0.1 µg of pPCV64 DNA. 500–2,000 G418-resistant colonies obtained under each condition was replica cultured on a YPD plate containing 800 µg/ml of hygromycin B. The ratio of colonies showing resistance to hygromycin B to those showing resistance to G418 does not vary largely between the pulse conditions and remains in the range of about 1–2%. Further, the G418-resistant and hygromycin B-resistant strains were cultured in YPD liquid medium overnight to obtain strains which became G418-sensitive by falling out of pPCV64 which was present as a plasmid. When 40 strains were examined, 10 G418-sensitive and hygromycin B-resistant strains were obtained. It was expected in these strains that the fragment containing the PGK gene promoter, the HPT gene and the PGK gene terminator was retained on chromosome. The chromosomal DNA was prepared from these 10 strains, and it was examined by PCR whether the HPT gene expression cassette was integrated in the chromosome or not.

As a primer therefor, primer 1; 5'CAAGTTGATCCTTCTCCGGA3'    (SEQ ID NO: 35)

which was synthesized on the basis of the DNA sequence outside 5' end of the PGK gene promoter fragment used for the HPT gene expression, primer 2; 5'GAAACTTCTCGACAGACGTC3'    (SEQ ID NO: 36)

which was synthesized on the basis of the sequence inside the HPT gene, and primer 3; 5'CATCGGGTAAGGTCTACATG3'    (SEQ ID NO: 37)

which was synthesized on the basis of the sequence in the PGK gene terminator fragment used for the HPTgene expression were used.

PCR was conducted 30 cycles under the condition of 95° C. for 1 minute, 55° C. for 1 minute, and 72° C. for 5 minutes. The result were as shown in FIG. 50. FIG. 50(1) illustrates the electrophoresis of the PCR reaction products with primer 1 and primer 3. A 2.7 kb amplification fragment due to the endogenous PGK gene was observed in every sample, and a 2.6 kb fragment was observed in five samples of Nos. 3, 5, 7, 9 and 10. The 2.2 kb fragment was considered due to replacement of one of the two endogenous PGK genes by the fragment containing the PGK gene promoter, the HPT gene, and the PGK gene terminator used for transformation. Moreover, the result of PCR of the same DNA sample with primer 1 and primer 2 is shown in FIG. 50(2). A 1.4 kb amplification fragment was observed for five samples in which a 2.6 kb fragment was observed, and in these five clones the endogenous PGK gene was replaced by the HPT gene by homologous recombination.

SEQUENCE LISTING ( 1 ) GENERAL INFORMATION:

( i i i ) NUMBER OF SEQUENCES: 40

( 2 ) INFORMATION FOR SEQ ID NO:1:

( i ) SEQUENCE CHARACTERISTICS:
        ( A ) LENGTH: 880 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:1:

```
CTGCAAGCTA  CTTTGTAATT  AAACAAATAA  CGGGATTATA  TGTCAATATC  ATTATGATTA    60
TTTAGGAAAA  CATGTAGACC  TTACCCGATG  CACCTCCACC  AACAAGCCAA  TTCTGGGTGG   120
GATGGAAGTT  ACACACTGCT  GGTACGTTGG  TCACCAGTGG  GTTTGACAAA  TGTGCCAGCT   180
GATGACCATC  TCGGTCGTAG  ACGTCAAAGT  ACTTGTTCAT  ATTGGCAATG  ACAAACTTTT   240
CTTTATCCGG  GGTATATTGC  TGCCACCTTG  CCTTCAAAAT  GGATACCCAT  CTTCCCGTTT   300
GACAGTTGTG  TTTGATACGA  TGACTTGGGG  TCAAATCACC  TTCAATAGCG  AAGTTCTTAG   360
GTTTAGTGCT  GATGTCCTCA  CCAAGATTGA  AGATGTTAAC  TGTGTCATCG  TAACCGTTAC   420
AAACAAGGTC  ACCAGATCTA  TTCCAATCCA  CGATGGAAAC  TGACAATCTT  GAATCATAGA   480
CGCCAACAGT  GTGAAGAGTC  TCCAGGTTAT  CATCCCATTC  ATCCAATCA   CACGTAGTTA   540
CTGTTCTTAG  ATCCCAAACC  TTCAAAGTTC  GATCCAATGA  GGCAGTAGCA  ATCTGGTTCT   600
TATTCATCGG  ATTGGTAGTG  AATCCACCAA  TCTTTTTATT  CGACAATCTC  AAAACTTGTC   660
TTCTTGAGTG  ATCGCCTGCT  CTTAGGTCAA  TTCTGCTGAA  TTGTCCTTGC  ATTGTTGTGT   720
AGTACATTTC  ATTGTCGTTG  TTGTAATTTA  TGTCAGTGAT  ACCGACGTCA  AAGTCGTTGA   780
TGAATAACTG  TGAGGACTTC  ATGGAGCGTA  GATCAATTGA  GCGAATGGAC  CCATCATACG   840
ATGCACTGTA  GACCTTCGTC  GTGTCATTCA  TGTTGAATTC                           880
```

( 2 ) INFORMATION FOR SEQ ID NO:2:

( i ) SEQUENCE CHARACTERISTICS:
        ( A ) LENGTH: 1346 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:2:

```
AAGCTTTTGT  CTTTTAGGAG  CCTTCTTTTC  ACCCTGGCTT  TCTTCAGACT  CCACGCCTCT    60
CGCCCGTTTG  TTGTTGATCT  TCTTCTGTTG  CTTCTTCGTG  AGCTTACCAG  TATCCAGATG   120
CGTTGTCAGG  GCAAGAGGGT  CATGTTCAAG  CTCCTCTTTC  ACTTTCAGTC  CAATACGTTT   180
CCAGGCAGGG  ATGTGTTCGC  TCATCGTTCC  AGACTCGAGT  GGTGAAAACT  ATGGCAACCT   240
CTACTTCCTT  TCCAAACACA  CAGCGTGCTT  TGTAGTGTGT  GCCTAAGAGC  TGAATTTTTT   300
TTCCTTCCAT  GCTGCGCTGC  GATGAGCTCT  GCCCGCCCGC  AGCCTCGGAG  GCTAGCGACG   360
TATAAAAAAG  GCCTGTGAAA  ATTTTATCCT  CCTCCTTAAC  GACCCTTCTT  TCTCTTCTTC   420
ACATTCAAAA  ACTTCAAGCA  GCTGTCTCTG  TTCCTTTGCT  GTGTTCTACC  ATTGGATATT   480
CCCATTCCCC  GTGGAGAACC  GAACTGGAGT  CTAGCAGCAT  GCGAGATCAA  TATTACACGG   540
TTTGAGTCTG  ATACGCTTGA  GCAGCCATTT  TTTGGCTTCT  CCTGGTGTGT  ATCCAGATAT   600
AGAAGTTCGT  ATACATTTCC  CATAGCGATT  GTAAAATGAT  TCTGCAATGG  AACCATCCGT   660
```

-continued

| | | | | | | |
|---|---|---|---|---|---|---|
| AATTGTAGGC | CTGCTGAGAT | GGCACTCGCA | ATGCCTCTGT | GTCTGGTTTT | TTGCCTTCTC | 720 |
| CGTCCATCAG | CACCAGTGGC | TTCTTAGGGC | ATAACGAGAC | GGCTCCTTGG | TGAAAGATGC | 780 |
| CCTGCTCCGT | CTGTCTGCCT | GTTGCTACAA | CCACTGCGTA | GTCAGATGAC | CCGGTCTGTG | 840 |
| TGCTGTGGAA | TCACCGGGAG | CGAAATTCCG | GTTTCGCTGG | CAGATGAGCT | CATCAACCAC | 900 |
| ATCAACTGGA | GCAACCTCAC | CAGAGGACAC | GTAACCTGCC | CGGTTGAATT | CTGTCAAACC | 960 |
| GTACATCACA | CAACAACAGC | AGCAGCAACA | ACAACAACGT | CAGTTGTCGT | TCGCATGGCG | 1020 |
| ACGTTACCTA | ACGGCACCAA | CATCGTCTCG | TCCTCGCCAA | TGCCTGTTTC | CCCTACCCGG | 1080 |
| AGTGGCCCGG | CCCACCTGTC | GTTCTTTTTT | CGTCAATTGT | GTCCAGCTGG | TGCCATCACC | 1140 |
| ATATGTTCAA | GTGCGTGGCC | TGTACTAGCG | CAGTCTGCTG | CAGTATAAAA | GGGATTGCTG | 1200 |
| AGGCCCCCTT | TAGCGTTTCC | AATTAACAAT | TGATTCCCTT | TTCCCCATAG | TCCGTTTGTA | 1260 |
| CTACATCCTA | CATAACAAAA | GTGAGTGTTA | CAAGACAAGT | GTGGCGGTCA | ATTGGATCAT | 1320 |
| TTGGACTAAC | ATACTGGCGG | ATAAAG | | | | 1346 |

( 2 ) INFORMATION FOR SEQ ID NO:3:

( i ) SEQUENCE CHARACTERISTICS:
  ( A ) LENGTH: 2330 base pairs
  ( B ) TYPE: nucleic acid
  ( C ) STRANDEDNESS: double
  ( D ) TOPOLOGY: linear ( i x ) FEATURE:
  ( A ) NAME/KEY: CDS
  ( B ) LOCATION: 1259..2059

( i x ) FEATURE:
  ( A ) NAME/KEY: mat_peptide
  ( B ) LOCATION: 1259..2059

( x i ) SEQUENCE DESCRIPTION: SEQ ID NO:3:

| | | | | | | |
|---|---|---|---|---|---|---|
| AAGCTTATGG | AGGAGATTGG | GAAGATTGAA | CGAGGTGAGA | TGGACACGTT | GCTGATTGAC | 60 |
| GAGATCGGCA | AGAAGGAGGC | ACCTGTGGTG | AAACCACTTA | CACCCGACGT | GGATAGTAAT | 120 |
| GTAACAGGGG | AACCGACTGG | ACATAGTTCT | ACGACACCAC | CACCGGTGGA | ACAGGACTCG | 180 |
| AGCACAACCA | CGAGGAAGAG | AGCACAAGAC | GATGGTGAGG | AAAACACAAG | GAAGAAGCCC | 240 |
| AAGGTTGAGG | CAGAGAAAAA | GGCAGAGCAA | GAGGCAGAGA | AAGAGGCAGA | GAAAGAGGCA | 300 |
| GAGAAAGAGG | CAGAGCAAGA | GGCAGAGAAA | GAGGCTCCGC | GTGCAGTGCC | GAACAAGAGA | 360 |
| CTACAACACA | TTGCTACTCC | TCTCATCGAG | AGCATCTCGT | CATACAAGTA | CGCCTCAGCG | 420 |
| TTTCTACACC | CTGTTAACGA | GTCCAGTGCA | CCCAACTATT | ACTCTCTGAT | CAAGAAACCA | 480 |
| AGGGATCTGA | AGACCATCAA | ACAGATGGTC | AAGGACGGAC | GTATACAGAC | CAATCTTGAG | 540 |
| CTGGAGAGGG | AGATCTTGCT | GATGTTTGCC | AATGCCATCA | TGTACAACAA | GACCGGGACG | 600 |
| GATATCTACG | AGTGGACCAA | GGAGATGCAG | CCGGAAGTTG | ACAAGCTCAT | CGAGCTGTTT | 660 |
| AACGAGAGTA | AATAGGATAC | AGGCTAGAGA | TCAAAGAAG | AATAGAAACA | GCTCGATAAA | 720 |
| ACGGTATTGT | AAGTGGTATG | TACAAAGGGG | TGTGTCTTGC | TCAACGTCTT | TGCATCTGCT | 780 |
| GAGTCAAAGC | AGCGTTCTGC | TCTTGGAATC | TAAGACCGAC | TCTTTCCGAA | TGCTTGAGGA | 840 |
| ACTTTTCAGA | GCACTTCAAC | ACACAGGATT | CCTCCTTTGA | TGATAGCTTT | TCAGAGGTGA | 900 |
| AGTCGTTGAC | ACAGTCGCTG | AAACAACGCT | CAACGAGGTT | GGAATAAAGA | CGCATAAAGT | 960 |
| CCTTCATCTG | CTTCTGCTCA | ACAAGCTGCT | GGAACTGCTG | CTGCTCTTTT | GGGTTCAATT | 1020 |
| GGTCCATCCT | TGCTACTTTT | CCGCCTAGTT | TCGATTCCGA | TTCTGATAGA | GAAGCCCAGC | 1080 |

-continued

```
TATGAATGGA AGAAATTTTT CACTTTTGTA TGTCCTTTTT TTCACGCTTC GTTGCTTCGG      1140

ACAAAAAAAT AGTGGAGGCA CTCGGTGGAG GGAAGCTATC CTCGAGATGA AAAATTTCAA      1200

GCTCATCTCA TCGTCCAAGT GGGACAGCAA GCTGAGGCTT CTGAAGAGGT TGAGGAAA       1258

ATG GTC ACC ACG TTA TCG TAC ACA GAG AGG GCA TCG CAG CAC CCT TCG       1306
Met Val Thr Thr Leu Ser Tyr Thr Glu Arg Ala Ser Gln His Pro Ser
 1               5                  10                  15

CCA CTT GCT AAG CGT CTG TTT TCG CTT ATG GAG TCC AAG AAG ACG AAC       1354
Pro Leu Ala Lys Arg Leu Phe Ser Leu Met Glu Ser Lys Lys Thr Asn
             20                  25                  30

CTG TGT GCC AGT GTC GAT GTT CGT ACC ACA GAG GAG TTG CTC AAG CTC       1402
Leu Cys Ala Ser Val Asp Val Arg Thr Thr Glu Glu Leu Leu Lys Leu
         35                  40                  45

GTT GAT ACG CTT GGT CCT TAT ATC TGT CTG TTG AAG ACG CAT ATT GAT       1450
Val Asp Thr Leu Gly Pro Tyr Ile Cys Leu Leu Lys Thr His Ile Asp
     50                  55                  60

ATC ATT GAT GAC TTC TCT ATG GAG TCT ACT GTG GCT CCA CTG TTG GAG       1498
Ile Ile Asp Asp Phe Ser Met Glu Ser Thr Val Ala Pro Leu Leu Glu
 65                  70                  75                  80

CTT TCA AAG AAG CAC AAT TTC CTC ATC TTT GAG GAC CGT AAG TTT GCT       1546
Leu Ser Lys Lys His Asn Phe Leu Ile Phe Glu Asp Arg Lys Phe Ala
                 85                  90                  95

GAT ATC GGC AAC ACC GTC AAG GCA CAG TAC GCC GGT GGT GCG TTC AAG       1594
Asp Ile Gly Asn Thr Val Lys Ala Gln Tyr Ala Gly Gly Ala Phe Lys
             100                 105                 110

ATT GCG CAA TGG GCA GAT ATC ACC AAC GCC CAC GGT GTC ACC GGT GCA       1642
Ile Ala Gln Trp Ala Asp Ile Thr Asn Ala His Gly Val Thr Gly Ala
         115                 120                 125

GGT ATC GTC AAG GGG TTG AAG GAG GCT GCA CAG GAA ACC ACG GAT GAG       1690
Gly Ile Val Lys Gly Leu Lys Glu Ala Ala Gln Glu Thr Thr Asp Glu
     130                 135                 140

CCA AGA GGG CTG TTG ATG CTT GCG GAG CTG AGC TCC AAG GGC TCC TTG       1738
Pro Arg Gly Leu Leu Met Leu Ala Glu Leu Ser Ser Lys Gly Ser Leu
145                 150                 155                 160

GCC CAC GGG ACA TAT ACC GAG GAG ACC GTG GAG ATT GCC AAA ACT GAT       1786
Ala His Gly Thr Tyr Thr Glu Glu Thr Val Glu Ile Ala Lys Thr Asp
                 165                 170                 175

AAG GAC TTT TGT ATT GGA TTC ATC GCA CAG AGA GAC ATG GGT GGC AGA       1834
Lys Asp Phe Cys Ile Gly Phe Ile Ala Gln Arg Asp Met Gly Gly Arg
             180                 185                 190

GAA GAT GGG TTC GAC TGG ATC ATC ATG ACA CCA GGC GTG GGA CTC GAC       1882
Glu Asp Gly Phe Asp Trp Ile Ile Met Thr Pro Gly Val Gly Leu Asp
         195                 200                 205

GAT AAG GGC GAC TCC CTG GGC CAA CAG TAC AGA ACT GTC GAT GAG GTT       1930
Asp Lys Gly Asp Ser Leu Gly Gln Gln Tyr Arg Thr Val Asp Glu Val
     210                 215                 220

GTC AGT GGT GGC TCT GAC ATC ATC ATC GTT GGT AGA GGC TTG TTT GGA       1978
Val Ser Gly Gly Ser Asp Ile Ile Ile Val Gly Arg Gly Leu Phe Gly
225                 230                 235                 240

AAG GGA AGA GAT CCA ACA GTG GAA GGT GAG CGT TAT AGA AAA GCA GGC       2026
Lys Gly Arg Asp Pro Thr Val Glu Gly Glu Arg Tyr Arg Lys Ala Gly
                 245                 250                 255

TGG GAT GCT TAT CTC AAG AGA TGC TCA GCT CAA TAAGCGTTGA GCTCTGGCTT     2079
Trp Asp Ala Tyr Leu Lys Arg Cys Ser Ala Gln
             260                 265

GTATAGGTTC ACTTGTATAA AATGTTCATT ACTGTTTTCG GAAGTTGTAG ATTGCCATTT     2139

TTGCGCAAAT TGACGCCAGT CTTTTTTTGC GCCAAATGTC AGTTTTTTG CGCCAAAATT      2199

TACTTCATCT TATACAACTG CAAAAACCAT CCAATCCAAT CCAGAAAGGA CTGATCAATG     2259
```

```
GTGGTGATTG  ACTCAAGTTC  TGATGCTACA  CAACAGACAG  AGCTCTCTAA  AAAGAATTCG         2319

ATATCAAGCT  T                                                                  2330
```

( 2 ) INFORMATION FOR SEQ ID NO:4:

( i ) SEQUENCE CHARACTERISTICS:
        ( A ) LENGTH: 267 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Val  Thr  Thr  Leu  Ser  Tyr  Thr  Glu  Arg  Ala  Ser  Gln  His  Pro  Ser
 1              5                    10                   15
Pro  Leu  Ala  Lys  Arg  Leu  Phe  Ser  Leu  Met  Glu  Ser  Lys  Lys  Thr  Asn
              20                   25                   30
Leu  Cys  Ala  Ser  Val  Asp  Val  Arg  Thr  Thr  Glu  Glu  Leu  Leu  Lys  Leu
         35                   40                   45
Val  Asp  Thr  Leu  Gly  Pro  Tyr  Ile  Cys  Leu  Leu  Lys  Thr  His  Ile  Asp
      50                   55                   60
Ile  Ile  Asp  Asp  Phe  Ser  Met  Glu  Ser  Thr  Val  Ala  Pro  Leu  Leu  Glu
 65                  70                   75                           80
Leu  Ser  Lys  Lys  His  Asn  Phe  Leu  Ile  Phe  Glu  Asp  Arg  Lys  Phe  Ala
                  85                   90                        95
Asp  Ile  Gly  Asn  Thr  Val  Lys  Ala  Gln  Tyr  Ala  Gly  Gly  Ala  Phe  Lys
               100                  105                 110
Ile  Ala  Gln  Trp  Ala  Asp  Ile  Thr  Asn  Ala  His  Gly  Val  Thr  Gly  Ala
              115                  120                 125
Gly  Ile  Val  Lys  Gly  Leu  Lys  Glu  Ala  Ala  Gln  Glu  Thr  Thr  Asp  Glu
     130                  135                 140
Pro  Arg  Gly  Leu  Leu  Met  Leu  Ala  Glu  Leu  Ser  Ser  Lys  Gly  Ser  Leu
145                      150                 155                      160
Ala  His  Gly  Thr  Tyr  Thr  Glu  Glu  Thr  Val  Glu  Ile  Ala  Lys  Thr  Asp
               165                   170                 175
Lys  Asp  Phe  Cys  Ile  Gly  Phe  Ile  Ala  Gln  Arg  Asp  Met  Gly  Gly  Arg
              180                   185                 190
Glu  Asp  Gly  Phe  Asp  Trp  Ile  Ile  Met  Thr  Pro  Gly  Val  Gly  Leu  Asp
         195                  200                  205
Asp  Lys  Gly  Asp  Ser  Leu  Gly  Gln  Gln  Tyr  Arg  Thr  Val  Asp  Glu  Val
     210                  215                  220
Val  Ser  Gly  Gly  Ser  Asp  Ile  Ile  Ile  Val  Gly  Arg  Gly  Leu  Phe  Gly
225                  230                  235                       240
Lys  Gly  Arg  Asp  Pro  Thr  Val  Glu  Gly  Glu  Arg  Tyr  Arg  Lys  Ala  Gly
               245                   250                 255
Trp  Asp  Ala  Tyr  Leu  Lys  Arg  Cys  Ser  Ala  Gln
               260                   265
```

( 2 ) INFORMATION FOR SEQ ID NO:5:

( i ) SEQUENCE CHARACTERISTICS:
        ( A ) LENGTH: 2086 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: join(1111..1114, 1482..1795)

5,849,524

-continued ( i x ) FEATURE:
    ( A ) NAME/KEY: mat_peptide
    ( B ) LOCATION: join(1111..1114, 1482..1795)

( x i ) SEQUENCE DESCRIPTION: SEQ ID NO:5:

```
GGATCCAATC  GTTGAAAGTG  ATCAAGCTGA  TTACAAAAGT  AAGTATGAAA  AGAGCCAATG        60

TTGAGAGTCT  CAGGAACCAC  ATCGACTTCT  TCGTGCCATC  CTCCCACATT  CTGAAGCCCA       120

AGAACCCACA  AATCATCAAA  CACCAACACG  ATGCGGACGC  CAACCCGAGT  TGTAACGCCA       180

CAAAGTACGG  GTACGACCCT  GTTCCAGGAG  GGCTCACGCC  GCAATCAACA  ACCAAAGTCG       240

CCACGATCAA  CGCCAGTATC  AAGTAAAAGA  AGAATAGCAT  CTCCAGTCTT  CCGATAGCTG       300

TGTACTTCGA  TCTGACGTTG  TAGATGATGA  TGATCATGAT  CACGAGGGCA  CCAATGTTGA       360

CAAAGGCGTT  ACCAATCTGG  AATATCACGG  TATTGGCAAC  GTCTATCGGA  CGGGCGTAGC       420

ACTCAGGGAT  GATCCCTTCG  TTCAGGTGCG  TGAACTGCTC  GTTCGTCGTT  GCCTTCACAA       480

CCTGGCACAA  CGGGAGCGGC  GTGTTGTGGC  ATAGCGAGTT  GAAATCACCG  AATGCCATTG       540

TGTTTTATCG  TTAGGGAGAC  CTGTTTGAAG  CTGACAGCGG  GATGAAGATG  AGGAAGGAGA       600

GCACAACAGC  TGAGCGGAAG  TCTCTGTGAT  GCTTGGTGGA  CCGGGTGTAG  GTGGAATCTC       660

CCTGGTGAGC  GTACTTGCAA  CGGTGCTCAG  CGACTTCTTC  TCGAGAGGAA  ACGTAAACAA       720

AGAGGTTTCA  ATGTTGATGT  TGATGTGTAT  TTTTGTTACA  AAAGCAGAAA  TTGTAAACAA       780

AAAGGTATAA  TTAGGGCTCT  GGTGTAATGA  TGGGCACGTG  ACGTTACCGT  GCTGGTCGAT       840

TTTAGGGCTA  TTGGTTCGCG  TCCCGCTGGT  GTCCGGGTTA  GCGTGTCAAT  GTGGCGCCTC       900

CCGATTATTA  CATAAGAAAA  CACCCACCCA  CGCAACACCT  GGTGTCTGGA  TGTTGACGCT       960

TTGTATGCGT  GTGTGTGTTT  TTTCTTCCGT  CTTGTTGGGC  CACTCTGCGC  GAGCGTTGGC      1020

GACTCACCGG  TGAAATTTAT  CGAAAACTTT  CAGGCTCAGG  CCCTTTTCAA  CACTACCCTT      1080

TGAGATCACA  TCAAGCAGTA  ATCAAACACA  ATG  G  GTATGTGGGA  AACGACGACG          1134
                                    Met
                                     1

TGTGCGGTGT  GTGAATGCCA  TTAGTGGGAT  ATGTGGTAGT  CTCGAGCGTG  GATATTATCG      1194

ATAGGGATGG  TGCTTGTTCT  ATACGTCTTG  CTGGGAAGGA  AGAAAGCGAT  GAAGTATGTG      1254

GGAAGAAGGG  GTGGTTTAAG  AGAGGAAGTA  GACATGTAAC  AAGTGTGTTC  AGAGAACAAG      1314

GACGGAAATA  TCACCTATAT  GACGTACACA  TCACGAACTG  CTCCTGGAGG  AAGCGACAAG      1374

ATGAATATCA  ACAGGCATCA  TCATATCTCT  ACAATGGCTC  GTTCCCAAAG  CACACGCACA      1434

AACAAATCCG  AGACTTTTGT  ACTAACAGCT  GTATCTCTGA  CAAATAG   TT  AAC  GTT      1489
                                                          Val Asn Val

CCA  AAG  ACC  AGA  AGA  ACC  TAC  TGT  AAG  GGT  AAG  GAG  TGC  AGA  AAG  CAC    1537
Pro  Lys  Thr  Arg  Arg  Thr  Tyr  Cys  Lys  Gly  Lys  Glu  Cys  Arg  Lys  His
 5                 10                          15                          20

ACT  CAA  CAC  AAG  GTT  ACC  CAG  TAC  AAG  GCT  GGT  AAG  GCT  TCC  CTC  TTT    1585
Thr  Gln  His  Lys  Val  Thr  Gln  Tyr  Lys  Ala  Gly  Lys  Ala  Ser  Leu  Phe
                    25                          30                          35

GCC  CAG  GGT  AAG  CGT  CGT  TAT  GAC  CGT  AAG  CAA  TCC  GGT  TAC  GGT  GGT    1633
Ala  Gln  Gly  Lys  Arg  Arg  Tyr  Asp  Arg  Lys  Gln  Ser  Gly  Tyr  Gly  Gly
                40                          45                          50

CAA  ACC  AAG  CCA  GTT  TTC  CAC  AAA  AAG  GCT  AAA  ACC  ACC  AAG  AAG  GTT    1681
Gln  Thr  Lys  Pro  Val  Phe  His  Lys  Lys  Ala  Lys  Thr  Thr  Lys  Lys  Val
           55                          60                          65

GTT  TTG  CGT  TTG  GAG  TGT  GTT  GTC  TGC  AAG  ACC  AAG  GCC  CAA  TTG  GCT    1729
Val  Leu  Arg  Leu  Glu  Cys  Val  Val  Cys  Lys  Thr  Lys  Ala  Gln  Leu  Ala
      70                          75                          80

TTG  AAG  CGT  TGT  AAG  CAC  TTC  GAG  TTG  GGT  GGT  GAC  AAG  AAG  CAA  AAG    1777
```

| Leu | Lys | Arg | Cys | Lys | His | Phe | Glu | Leu | Gly | Gly | Asp | Lys | Lys | Gln | Lys |
| 85 | | | | | 90 | | | | 95 | | | | | | 100 |

```
GGT CAA GCT TTG CAA TTC TAAGCTTAAG ACAATTGTTG AAAGTTTTAT            1825
Gly Gln Ala Leu Gln Phe
            105

TATTATCACT ACACTGTGTT TTTGATGTCA TCTAATGTAA AAGCGTTTAT ATTACCACTT   1885

GGTTCGGTAT CCTGTAGAAG AATACGGCCT GTAGCGTAGC ATTCCCACAG GAGGATCACA   1945

GCAACATAGA CCAAACAATG TCACGCACGG GGATCGAACG CGGAACCAAA CCTCTCCCTC   2005

CTCCCCCTTT CACCGCGGTT ATTTTGTTAT GGGCACACAC AGGGGAAGGA AAAAAATGCA   2065

CACACGCACA AAAGCGAGCT C                                             2086
```

(2) INFORMATION FOR SEQ ID NO:6:

(i) SEQUENCE CHARACTERISTICS:
        (A) LENGTH: 106 amino acids
        (B) TYPE: amino acid
        (D) TOPOLOGY: linear (ii) MOLECULE TYPE: protein (xi) SEQUENCE DESCRIPTION: SEQ ID NO:6:

| Met | Val | Asn | Val | Pro | Lys | Thr | Arg | Arg | Thr | Tyr | Cys | Lys | Gly | Lys | Glu |
| 1 | | | | 5 | | | | | 10 | | | | | 15 | |

| Cys | Arg | Lys | His | Thr | Gln | His | Lys | Val | Thr | Gln | Tyr | Lys | Ala | Gly | Lys |
| | | | 20 | | | | 25 | | | | | 30 | | | |

| Ala | Ser | Leu | Phe | Ala | Gln | Gly | Lys | Arg | Arg | Tyr | Asp | Arg | Lys | Gln | Ser |
| | | 35 | | | | | 40 | | | | | 45 | | | |

| Gly | Tyr | Gly | Gly | Gln | Thr | Lys | Pro | Val | Phe | His | Lys | Lys | Ala | Lys | Thr |
| | 50 | | | | | 55 | | | | | 60 | | | | |

| Thr | Lys | Lys | Val | Val | Leu | Arg | Leu | Glu | Cys | Val | Val | Cys | Lys | Thr | Lys |
| 65 | | | | | 70 | | | | 75 | | | | | | 80 |

| Ala | Gln | Leu | Ala | Leu | Lys | Arg | Cys | Lys | His | Phe | Glu | Leu | Gly | Gly | Asp |
| | | | | 85 | | | | | 90 | | | | | 95 | |

| Lys | Lys | Gln | Lys | Gly | Gln | Ala | Leu | Gln | Phe |
| | | | 100 | | | | | 105 | |

(2) INFORMATION FOR SEQ ID NO:7:

(i) SEQUENCE CHARACTERISTICS:
        (A) LENGTH: 975 base pairs
        (B) TYPE: nucleic acid
        (C) STRANDEDNESS: double
        (D) TOPOLOGY: linear (xi) SEQUENCE DESCRIPTION: SEQ ID NO:7:

```
AAGCTTACAG CGAGCACTCA AATCTGCCCT CCGAGCCCTC CGGCCCTCTC TTCAACAAAC    60

TCGCGCTGCA CTTCGTCGTC AGTGGTGCCA ATCACCCAAC GTGGAGGTAT CAAGAGGTGC   120

TCCAGCCCAC AAAGCGACAT CAAAGACAAC AACCCTGCCG GCCTACGTCC TACACACCCT   180

GGTGATCGCA GACATTGTAC AAGGTGCCAC GCAATAACCT ACAGGCACCG CACATGACGA   240

TGGCCTTGGT TGTGCAACCA GTGACTTCCA CGGTCCACGC AGCAACATGA ACCACACCAC   300

CCAGAATCGA TGCGCGCAAC AACAGTTGTT CCGGTTCACT CAGCCCACA GCGAGTCGCT    360

GGCAGAACAC GAGCCTGAGG GCGGAAAGAG GGTAGAGGAA AGCGCAAGGA CAGGGGACAA   420

CCTGGCCCAA TTGATGTCAT ATAAACCCTC TCGATCAATT GAGCACACTC ATCCGCCAAT   480

TGACCCCTGT TCGCAGCTCC ACGCCCATG TTCCTCGTCC CTGGTGTAGC TTCTCCCTA    540

AATTCCAGCG CTTGGTTCCG CCCTCCCTGT CTCCCGGGTT TAACGAACGT GTGTACCATC   600
```

```
TGATGGTAAT  CCGCTCCCGT  CCGCGCAACA  CAACTCACAA  GCAGATCACA  CCTGTACACG    660

CCGCTGCTGA  TGCGCCCAAT  TTAATTTTTT  TTCTCTCAAT  GTAGGGGAGA  AGCCTTGGGA    720

GCTCCCGACT  CCCAGTTGGG  CACAGCTGCC  ACCTCATGAC  TTTTCCTGTG  TGTGCCTGTC    780

TGACGTTACG  TGTGATGTAG  TGGCCCCCGT  TCGGTGTGTT  TTCGCCTGTT  GCGCTGTGCC    840

CCCCTTAAAA  GTATAAAAGG  AAGTGCAATT  GCTGTTTGTG  TTGATTGTTG  ATCCTTGTTT    900

CCTCTGTTTC  CTCCTCATCA  CACAAGAAAG  GTTTCTTCTT  TCCAACAGAT  ACAAACACA     960

CTTACAAACA  ACATA                                                          975
```

( 2 ) INFORMATION FOR SEQ ID NO:8:

( i ) SEQUENCE CHARACTERISTICS:
        ( A ) LENGTH: 802 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:8:

```
ATTGTATGAC  TTTTATTTAT  GGGATTACGT  TATAAATTAT  GATCCTCATG  GATTATCTTA     60

TTAAGTCTCC  ATCTTGTAGC  TTGTAATATG  ATGAACACTC  GTGAGTTTTC  CAGGTAATTC    120

ACCGTGCCTC  GTCCATGCAC  TTTTATCAGC  CTCGACGTCA  TACATTGCAT  GGTGAGTAAC    180

TGGAAAACGG  CTTTTTACGT  TCTGTTGTAT  ATGGCTAAAC  GCTTCTATGG  CACGGCGCTA    240

TTAACCTGTC  TGACATTTCA  ACCTGGTGTT  GATGGCTTAA  ACGATAATAC  GGTGAGATAT    300

ATAGCTAACA  GAATGGGGGT  GACGCACTGA  TTCCACTGTA  TATATAGGCG  ATATGTGTTG    360

TTGGATGGAC  GTTTCTTTGT  CTCCTGATCC  ACAATAGTAG  CTCAGCTCCG  TGCCAACTGG    420

TTCGCTGGTA  CGATAGTGAG  GGATGAATGA  AACCTTTTCG  TTTTCTTCTG  CGCTTCCACG    480

GAACTGTGTA  GATTTCTCTC  GTGAATAGCG  AGTTAAGCCA  CGAGTGGGGT  CTGCAATTGA    540

AGGTGTGATA  CCAGAGTCAA  AAGTTTGGAT  GTGATGGAAA  CTTCAAAGGC  TTCTCGGTGG    600

TATATCAAAC  GATTCACAGA  GGTAGAAGCG  GATCTTGAAG  GCCAGAATAT  GCATTAAAAC    660

CAGCGTATAT  CAGTTTTGCT  TTCCCAGAGA  GGACTTTTGC  ATTATTCTTC  AGCTTTATCC    720

CTGGATTTTG  GGAGATGAAA  CATTGACAAA  GCTGGTTCGT  GATCCTAAAT  ACTTGCCTAC    780

TGACTCCTGA  GGTATTACAC  GT                                                802
```

( 2 ) INFORMATION FOR SEQ ID NO:9:

( i ) SEQUENCE CHARACTERISTICS:
        ( A ) LENGTH: 599 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:9:

```
TCTAGAGCTG  TCGACGCGGC  CGCGGAATTA  ACCCTCACTA  AAGGGAACGA  ATTCGGATCG     60

GTGTTTTGGG  CAGTGGGACC  AAATCGATGC  CCATGTTGTT  TTTTGTATT   TTCGAACTT    120

TTTCCCCATT  CGGTCATACC  GAAGGCGGTT  CAAGCCTGCA  AGAGACAACA  ACTATGGCTG    180

CTGTTCTTGG  AATGAAAATA  AACGCATTTG  GAAGTTTTGC  AGCCAAAACA  GGATGCGTTT    240

TCGCCATTTC  GGTGCGGCAT  TTCCGGTTTC  AGATTTTCGC  GAAATTTGTT  TTTCCCATCA    300

AATCTGCAAA  TTTCGGAAAC  GGGCCGCGCT  GATTGGCTGC  GTCCTGAAGC  GGCAATTTTT    360

CTCCCTCTCG  TTTGTTGATA  CAACCAAGAA  TTTCTTTTCG  TGCTCTGCGC  CAGCGCTATC    420

CAAATGTTTA  TAAATCTTGA  TGTGATTTCC  CGTTTTCTGT  CCTTGCTCAT  TCTGTCTCTC    480
```

| | | | | | | |
|---|---|---|---|---|---|---|
| TGTTGAACCA | TTGTTGTTTT | ACGAACTCAA | GGTCCAATTG | GAACAGTATG | TGCACTGCCA | 540 |
| ATGGAGCATT | GAAAGGGTTA | TTCGATGTCG | TCACCACGTG | ATACTAACCA | TTGATATAG | 599 |

( 2 ) INFORMATION FOR SEQ ID NO:10:

( i ) SEQUENCE CHARACTERISTICS:
        ( A ) LENGTH: 1188 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:10:

| | | | | | | |
|---|---|---|---|---|---|---|
| GCCGCTAATA | CCCCTTAGGT | TTTCGTTTCA | TACATAGAGT | GGTTGTTGTT | TAACATTTTA | 60 |
| TCGTGATTAA | TTTTTAATCG | AGTAATATAT | TATTGGAAAA | GTTTTTAGAC | TTTGAAGCGT | 120 |
| AGTATCGGTG | GCTTTGCGGA | GCTTAGCGCT | GTGTCCTTTC | TCCGTTGTTT | ATGGAGTGTT | 180 |
| GATGTTTTGT | GATTTACAGC | GATGTCCGGG | TTTTTGTGTA | CACGCTGCCC | TTGAACCAAA | 240 |
| AAAAAGCTG | CTGGGAATCG | ATCGAGGGAA | AAACATCAC | CAAAAAAAA | ACAAACAGCA | 300 |
| GAAAGTAAAC | AAACAACATT | ACAAACAACA | ACATCACACA | GCGGCACGCT | TAAACCAGG | 360 |
| GCGGTAGTGA | CGTGACTTGC | TTGTTTTCGA | TCAGCGAGTG | CGGTGTTATC | GATATCTTCG | 420 |
| AATCTGCTTA | TAGTTCAAGA | ACGCCTGGAT | CCCAAGCGTA | GTGAAGTGTT | CTCTTTTGTT | 480 |
| TACTTTCTGT | TTTGTATATT | AGTTCGGAAC | CCATTAGAAA | AGGTTCATCT | CTGAGATAAA | 540 |
| GAGCAAAGAC | GCACGAGACA | ATCAATCATT | TGAGATGGGA | TCAGTATCAG | CGGAGAGTGC | 600 |
| TGATAAGATT | GAGGAGAACA | GAGCAACTGG | GGCTTGTTTG | GACATTCTCT | CACCACCAAA | 660 |
| GCCTTCGTCA | ACGTCCACAC | CACCTACAGC | GACTGCTGGT | GCCATTGGCG | GGTCTGGTAA | 720 |
| TGAAACCAGT | GACAGCTTCA | ATCCTTTTGA | GAAGGACTCA | CTGGATGAAT | CTGCTTCGGT | 780 |
| GTTATCCACA | AAGCAACTGC | TTGCTGAGGG | ACAGGGATCA | AATGCCCTGC | CATCTGAACT | 840 |
| CGTTGATATC | AACTTGGCGA | TTAGCGCTCT | TAACTTGGAC | TTTGACGGTC | AAAAACGTGG | 900 |
| ACAAACTACA | GCCACTACAG | AGCCAGTAGG | TGTTTTGAAA | GATGGTGCCG | AACCTAGTGC | 960 |
| TACAGGATCA | GACGACCACC | CGCCACCAGC | TCTGTATCCA | CCAGGTATGA | TCCCACAGCA | 1020 |
| CATGCCATTT | TTCCCGCTAA | ACGAATTTGG | ACAGCCAATG | CATGCACCAT | TCCCTGGAGA | 1080 |
| CCATCCACAT | AGTCCAATCC | CGTGGGATTC | CAAACCTGGA | CAGACTCCTT | TTGGTTTAAT | 1140 |
| GGGATCTCAT | GGCCCAAATA | TGGATGGGTT | ACGCTCACAA | ATGGTACC | | 1188 |

( 2 ) INFORMATION FOR SEQ ID NO:11:

( i ) SEQUENCE CHARACTERISTICS:
        ( A ) LENGTH: 1921 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:11:

| | | | | | | |
|---|---|---|---|---|---|---|
| GATCATGTTT | CGTACAAAAC | ACCGCCACTC | CGTTATGAGA | AAGTCATAGT | TATATTTCGG | 60 |
| GGAAACTTAT | GTTGCTTGCA | AGGAATAATA | GACAGACAAA | TGTTTTACGA | AACTGAAGGA | 120 |
| TTAATACAAT | TGATGCAAAA | AAACAAAAAA | AAAAAAAAA | AAAAAAAAA | AAAAAAACA | 180 |
| AAACACAAA | AACACAAAGA | AAAAAAACAC | AAAGAAAAAA | AACACAGAAC | ATCCAAAACA | 240 |
| AACAACAAT | ATATATATAT | TTGCTAATAC | CATCACCCTC | CCTCATACAA | AAAAAAAAG | 300 |
| AAAATGGAAG | GAGCACGTAT | ATCTTTTCTA | TGATCTTTGG | ATATGGAATA | GATAAGCAAC | 360 |
| CCCTCTAGTG | AAGTACACAT | CAAGATACTT | GGGGAGCAAA | CTGAGAGCAC | ATGATATACA | 420 |

```
CGAAAGCCAC  CATATATCAT  ATATAAAAAT  ATGAAACATG  AAAAGTTATT  CATCTGTTGG    480

ATTCACTTTT  ATATGTTTTC  ATGCATTGTC  TACTCTATGC  CTCTGTCTTT  TCTCTGTTCC    540

TTTACACTCC  TCTATTATCA  AATTGAGTGT  TTCATTTATC  AAAGAAGTTT  GAGCTGGATC    600

AGAACTTTAG  ATATTCATTC  CTGTTTTCGA  TATATCTATA  CGATGTTCTA  ATATCCACTC    660

TCACTACCAT  TGTTAAAAAA  AGTTAAAATT  ATAGCTGTGT  GCCTTAAGGG  AATAAAGGAA    720

ATGGATCTTT  TGAATGTTAA  AAAACGAGAT  ACTCTTTTGT  AAACCAGAAA  ACGATTTTCA    780

AAACACAAAT  TGGTGAATGT  CACCAAGCAA  AAATTGTATC  CTAAAAAAAA  TAAATTTATG    840

AACTAAATTA  TCTCTGAACA  GACATTTAGT  CAACCTTTTC  TCCTTGCTCC  TCGGTCAAAG    900

GTTTTTCGTA  TAGATATATA  TACGGGTTGC  TTTTTTGTTT  CCACTCGTCT  AATCGAGTTT    960

CGATATCAAT  GGAGATTTAT  TCTTTGGCTT  TGATTCCATA  ATAATCCATA  TCCTAATAAA    1020

ACACTTTGAA  GCGAATTGAA  ACCCCAATAT  CTTTCTGGCC  ATTAAACAT   TTATAAAGTA    1080

CTGGATGTTT  AAAGAGCTTT  GAGAATTGCC  TAGCTTCAAA  ATATATTTGT  CTCCAATTAT    1140

GATTTGTAT   TTTCCTTTCT  TTGTTTTCTG  TAGTTATTTA  AATAAGTTC   ACTACGTTGT    1200

TTTTGAGGA   ACCGTTACTC  TATTTACTCA  AATTTATTAT  CAAATGTTT   TTTTTCGTT     1260

TGATTTATTC  AAATGCTGTC  GATATGTCCC  AGAAATATCA  TACAATTCAA  ATTTCTAAAG    1320

CCAGCGTTTA  TTATAAAGCT  TTGAGTTCTT  TCGACTTAAT  TACATGTATG  TAGCTCAAAC    1380

CAAAGTTACT  CTATAATTAT  AAAAAGACTA  TGAACCAATT  CAAGAATTCC  CCATTCCAG     1440

CAAATTTAGT  ATAGCTCAAA  TTCACACTGT  CATATGCAAA  AACCTAAATA  AGCAGATCAT    1500

TGTAAAGAGC  CGGCAGTTGT  ATATTCCAGT  GGGGCTGAAC  TTGTGGTTAG  GATTCACAGA    1560

CATCTTGTTG  TCGGATTTCT  ATTGATAGAA  GCTGTGCCAT  TGAAAATGGA  AATATAAAAT    1620

GGTATTGGGT  TGATCATATA  TGAATTTCTT  ATTACTCATA  ATAATAGGAG  AAATCATCGA    1680

ACATGGAACA  TAGATGCTAA  TTAAGGTACG  TACAGCATCC  TGTTCAATAT  TTCAACTTTT    1740

TAAGTATTAA  ATTAGTGAAG  AAATGTATTA  TGAACCATTG  TTCAATAATT  CTAATGTGTT    1800

TTTTGTGGTT  TTTTTTTTGG  CTTTTGGGAC  ATTGTAATTT  TTACTCATTT  ATTCGATGTC    1860

TCTTCAGGTT  TTTGTGTTTT  TTTTTTTTGT  GTTTAAATCT  TCGCGGAATT  GAGATAAGAT    1920

C                                                                         1921
```

( 2 ) INFORMATION FOR SEQ ID NO:12:

( i ) SEQUENCE CHARACTERISTICS:
    ( A ) LENGTH: 1798 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:12:

```
AAGCTTATAG  AATTTGAAGA  TATAAAAACA  CAACAAAGCT  ATGAAAGCAA  TGAGGGACG     60

ATTTGATGAA  CAGAAGGAGC  TATTCCCATT  AATTTAATAT  CTACCAATAG  ATATGTCAGT    120

CAAACATGTC  AGAAGTCATA  CTCACTAATT  ATATGAGCGG  GTGCGTTAGA  TATTTATATG    180

AGTTTGCATC  TTTCTACATG  GGGCTTTCAA  GTAACTGGAA  GTAATACAAC  TTTTGTTTAA    240

GTTGATAAAA  ACAAAAAACA  AAAAACAAA   AACAAAAAA   ACAAAATAA   AAAAAAAAA     300

AAACAAAAAA  AAAAAAACAC  ACACGCACAC  ACACACATAT  ACAAACACAT  ACAAAAAACT    360

TATCATAATT  AAGATAAATG  AAAGCTATCT  AAAATTTCCA  GACATTTTCT  GAAAAGTGG     420

CTGCCAGCTT  TATTGCTTTG  CTTTAAATTT  ATAAGAAAA   CTTCTTTGAA  ATCGAATATG    480
```

| | | | | | | |
|---|---|---|---|---|---|---|
| AAACAAGAGG | AAACGGATGA | AAGGATAAAA | CACAAATACA | GGAAAACATT | ATTACAAATA | 540 |
| AAGCACCTGT | AAGAGATAAA | TTTGTTACAT | TTAAAGGATT | CTACTTACAT | ATACAGAGAA | 600 |
| AGCAATTTCA | TAGACATAGG | GTCTACCGAA | CAGTCTTGAT | ATTTCAGACT | AGTATTTTTG | 660 |
| TTGTATTATG | GGGCTTGGTC | GGTATGTTAG | TAAAAAGTTC | ATTTTAAAAT | TTTCCAAGAA | 720 |
| GTGTTTTTAT | TGCAGAAAAA | TATCCGTGGT | TCAAGAGATA | ATGGGCTGTA | AATTTGTTTT | 780 |
| GTACCAAAAA | TATCTTAATT | AATACAAAGA | ATACCTTTTA | TGAAGGTAGA | TCAAGATCTT | 840 |
| AAATTTCATT | ACTCAGAAAT | GAATATACTT | GAAACTTCCG | AAATACTATG | TTATGGGAA | 900 |
| CAAATAAGAG | GAGCCATTTC | ATATTTATTT | TGGAAAGATC | GTTTTCTATG | CGCAGTTGTT | 960 |
| GGAATAGCGA | TATTATCATG | ACCTTATATT | CAGTCAGAGA | AAATAGGGTA | CGAATTTGAA | 1020 |
| AACAATGTTT | CAGCTTCAAA | GAGGACCTTT | AAACGGTCAG | GCAAAAGTTG | AGGTGTCAGT | 1080 |
| GTGTATAAAA | ATGTTCAATT | CATTTTTGGT | TGAAAGATGC | TTTAAAAGGT | TGGTGCAAAG | 1140 |
| AATCATATAT | GTGTATTGGC | TAGTTAAAAG | TTGCTTTATT | AAAAATATAT | GCAAACTAAA | 1200 |
| TTGTCTATAC | GATTGATAAG | GTGAAACTTA | GATAAACAAT | GAAAAGGAA | GGTGCTTTGA | 1260 |
| AAACCGACCA | GCTTCAAATA | AATATGTAAC | TATTTTTATG | GATGTGAAAA | TTAAATGTTG | 1320 |
| TCGAATCTGC | TGTTTCTAGA | TTTGTAGATG | AAAATGTTGA | CGTGAGAGTT | TTCATTTGTT | 1380 |
| TGTATTTTAT | ATTATGCTTT | GATTACTACT | CATAGCTTGG | GTTTAGCATG | GCCTGAGTAA | 1440 |
| GTAGGAAGAT | CCAATAAATT | GACTGTTGTC | GTTTTGAAAT | TAAATACTGA | AATGAATAAA | 1500 |
| AGTTTGACGA | GAAAAGACCT | GAAATATATA | AAAATGTTTT | GTATTATTTA | AGTCGGTTAC | 1560 |
| ATTCTCTCAC | TTTATTGTAA | CAACCATTAT | AGTGATGGGG | AAAAAATAAA | ACATAAGCCA | 1620 |
| CATAAGGAGA | TATTGTTCTT | TATTGAAAGG | ATGGAATCAT | TTTCTGGAAA | TGTCAAAAAT | 1680 |
| TAAATATTAC | TTGGTTTTTG | ATGAATTGTA | GAAGAAAAG | TAAATGCTGC | TATTCTCTTT | 1740 |
| CTTTACATTT | TCCATGTTTC | CTGATTCTGG | CTATGTCACT | TTAAGTTGTT | GAGATATC | 1798 |

( 2 ) INFORMATION FOR SEQ ID NO:13:

( i ) SEQUENCE CHARACTERISTICS:
  ( A ) LENGTH: 1054 base pairs
  ( B ) TYPE: nucleic acid
  ( C ) STRANDEDNESS: double
  ( D ) TOPOLOGY: linear ( x i ) SEQUENCE DESCRIPTION: SEQ ID NO:13:

| | | | | | | |
|---|---|---|---|---|---|---|
| CCACATTTGT | TGTACGAGAA | GGGCCAACGA | CAGCTCTCTT | CGAGGAAGAC | TTGGAGATAA | 60 |
| GCCTTGCTTG | ATTTGTAATC | TTCAAGAGAG | AGCTCTTTGT | AGCTTGTCTT | GTTGAGTGTC | 120 |
| TGAGAAGCAT | TTGTGCAATG | AATATGGGAG | AGATGAGATG | AGTAGAGAGC | AGCACAAGTG | 180 |
| GAATCAAATC | ACAATAACAA | CTTTAGCCAC | AGGGAGGTTA | AAAGAGGAGA | AGAAGGAGTC | 240 |
| CTTTCCAATT | GTGGCTAGTG | CAGAAGAGAA | AATTTGCTTG | CTACAATCGT | GGTGTGTATG | 300 |
| CAAACCCGTT | GTAAAGGTGG | TGTCTTTGTA | TATGTAGGGT | GTGTGGCTTC | GTCTCGAGAA | 360 |
| AGCACATAAG | CTGTGGCGCA | CTTTCTCGGG | TAAGTGATTT | AATTGCACGT | GATCTCAATT | 420 |
| TCTTTTTTTG | AAGCCACTAA | AGCTTACGTA | AGCGACCACG | GATCTGGTGT | TGGGATGTTT | 480 |
| TGGTTTTGGG | AGGGGCAGGG | GGTTTACATG | TTGGCTTTAT | CGATTGCGGC | GCTTTGTGTT | 540 |
| TGGGGGTGTA | TGCCCTAGCG | ACCCTGTGGG | CCACTGCCCA | GGTGCCCAGG | TGCGACCAGG | 600 |
| AAAAAAATTT | CTTCATCGCT | AGAGCTTTCT | TCAACCCCCT | TTCTTTCCTA | ATTCTTTTCA | 660 |
| ACTAACAACA | AATAAACACA | GTAACAAGAT | GTCATCTGAC | CTTTCAGACG | TTAGACTCTT | 720 |
| TGTCAGACCA | CTTCCATTCG | ATGTTAACGA | AGAGGACTTG | AAGAGCTTCT | TCTCCCCTAT | 780 |

| | | | | | | |
|---|---|---|---|---|---|---|
| TGGTGAAATC | ACCGATTTCA | TCGTTGCTAG | AGGTTATGCC | TTTGTTGAAT | ACGCTAATGC | 840 |
| AGATTTGGCA | AGACAAGCCA | TCGCTGAATT | GCACCAAAAG | CCGTTCGGTG | ATGTTCCATT | 900 |
| ATCCTTGGAG | TACGCTAAGG | CTCAAAAGCC | AAGATTCAGA | CTTCTTGTTT | CTAACATGCC | 960 |
| AGAAGGTGCT | GAGTGGCAAG | ATCTGAAAGA | TTTTGCTCTC | CAAAAGGGAT | TCGAAGTTAC | 1020 |
| CTACGCCAAC | GTTTTCCAAA | GAGAGAACAA | CGGT | | | 1054 |

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

| | | | |
|---|---|---|---|
| GGTCGACATA | TCGTGGTAAG | CGCCTTGTCA | 30 |

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

| | | | |
|---|---|---|---|
| TTCTAGACTT | TATCCGCCAG | TATGTTAGTC | 30 |

( 2 ) INFORMATION FOR SEQ ID NO:16:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

| | | | |
|---|---|---|---|
| GGGTACCTAA | CTGCAAGCTA | CTTTGTAATT AAC | 33 |

( 2 ) INFORMATION FOR SEQ ID NO:17:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

| | | | |
|---|---|---|---|
| GGAATTCAAC | ATGAATGACA | CGACGAAGGT | 30 |

( 2 ) INFORMATION FOR SEQ ID NO:18:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

| | |
|---|---|
| AGCGGCCGCT | 10 |

( 2 ) INFORMATION FOR SEQ ID NO:19:

( i ) SEQUENCE CHARACTERISTICS:

(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:19:

ACCACTATTA CCACTACGGT TTGCTCTACA                              30

(2) INFORMATION FOR SEQ ID NO:20:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO:20:

GACACATCTC TGAGCAGCAT GACTTGGTTG                              30

(2) INFORMATION FOR SEQ ID NO:21:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:21:

CTAGATGGTA GG                                                 12

(2) INFORMATION FOR SEQ ID NO:22:

(i) SEQUENCE CHARACTERISTICS:
(A) LENGTH: 10 base pairs
(B) TYPE: nucleic acid
(C) STRANDEDNESS: single
(D) TOPOLOGY: linear (xi) SEQUENCE DESCRIPTION: SEQ ID NO:22:

CCGGATCCGG                                                    10

(2) INFORMATION FOR SEQ ID NO:23:

(i) SEQUENCE CHARACTERISTICS:
(A) LENGTH: 31 base pairs
(B) TYPE: nucleic acid
(C) STRANDEDNESS: single
(D) TOPOLOGY: linear (xi) SEQUENCE DESCRIPTION: SEQ ID NO:23:

CCAAGCTTAC AGCGAGCACT CAAATCTGCC C                            31

(2) INFORMATION FOR SEQ ID NO:24:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:24:

CCTCTAGATA TGTTGTTTGT AAGTGTGTTT TGTATC                       36

(2) INFORMATION FOR SEQ ID NO:25:

(i) SEQUENCE CHARACTERISTICS:
(A) LENGTH: 30 base pairs
(B) TYPE: nucleic acid ( C ) STRANDEDNESS: single
        ( D ) TOPOLOGY: linear ( x i ) SEQUENCE DESCRIPTION: SEQ ID NO:25:

GGGATCCATT GTATGACTTT TATTTATGGG        30

( 2 ) INFORMATION FOR SEQ ID NO:26:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

GGACTAGTGA GATGACTCTA GGCATCTTCT        30

( 2 ) INFORMATION FOR SEQ ID NO:27:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

ATGACTGATA CATCATCCTC TTCATC        26

( 2 ) INFORMATION FOR SEQ ID NO:28:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

TAACGACAGC TGGCAAACCG ACTGGGAC        28

( 2 ) INFORMATION FOR SEQ ID NO:29:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

GGCGGCCGCA ATTAACCCTC ACTAAAGGGA ACGA        34

( 2 ) INFORMATION FOR SEQ ID NO:30:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

TTCTAGACTA TATCAATGGT TAGTATCACG TG        32

( 2 ) INFORMATION FOR SEQ ID NO:31:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

CCGGTACCTA AGCCGCTAAT ACCCC 25

(2) INFORMATION FOR SEQ ID NO:32:

(i) SEQUENCE CHARACTERISTICS:
    (A) LENGTH: 25 base pairs
    (B) TYPE: nucleic acid
    (C) STRANDEDNESS: single
    (D) TOPOLOGY: linear ( x i ) SEQUENCE DESCRIPTION: SEQ ID NO:32:

GGGCGGCCGC ACTCGCTGAT CGAAA 25

(2) INFORMATION FOR SEQ ID NO:33:

(i) SEQUENCE CHARACTERISTICS:
    (A) LENGTH: 25 base pairs
    (B) TYPE: nucleic acid
    (C) STRANDEDNESS: single
    (D) TOPOLOGY: linear ( x i ) SEQUENCE DESCRIPTION: SEQ ID NO:33:

GGTCTAGATA TGAAAAAGCC TGAAC 25

(2) INFORMATION FOR SEQ ID NO:34:

(i) SEQUENCE CHARACTERISTICS:
    (A) LENGTH: 25 base pairs
    (B) TYPE: nucleic acid
    (C) STRANDEDNESS: single
    (D) TOPOLOGY: linear ( x i ) SEQUENCE DESCRIPTION: SEQ ID NO:34:

GGAGATCTAT TCCTTTGCCC TCGGA 25

(2) INFORMATION FOR SEQ ID NO:35:

(i) SEQUENCE CHARACTERISTICS:
    (A) LENGTH: 20 base pairs
    (B) TYPE: nucleic acid
    (C) STRANDEDNESS: single
    (D) TOPOLOGY: linear ( x i ) SEQUENCE DESCRIPTION: SEQ ID NO:35:

CAAGTTGATC CTTCTCCGGA 20

(2) INFORMATION FOR SEQ ID NO:36:

(i) SEQUENCE CHARACTERISTICS:
    (A) LENGTH: 20 base pairs
    (B) TYPE: nucleic acid
    (C) STRANDEDNESS: single
    (D) TOPOLOGY: linear ( x i ) SEQUENCE DESCRIPTION: SEQ ID NO:36:

GAAACTTCTC GACAGACGTC 20

(2) INFORMATION FOR SEQ ID NO:37:

(i) SEQUENCE CHARACTERISTICS:
    (A) LENGTH: 20 base pairs
    (B) TYPE: nucleic acid
    (C) STRANDEDNESS: single
    (D) TOPOLOGY: linear ( x i ) SEQUENCE DESCRIPTION: SEQ ID NO:37:

CATCGGGTAA GGTCTACATG                                        20

( 2 ) INFORMATION FOR SEQ ID NO:38:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

TTGTGGAAAA CTTGCTTGGT TTGA                                   24

( 2 ) INFORMATION FOR SEQ ID NO:39:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

CCAAGCTTGG                                                   10

( 2 ) INFORMATION FOR SEQ ID NO:40:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

WTTTAYRTTT W                                                 11

What is claimed is:

1. A DNA sequence comprising a gene sequence encoding a ribosomal protein L41 of *Candida utilis*.

2. A DNA sequence according to claim 1, wherein the ribosomal protein L41 of *Candida utilis* has an amino acid sequence shown in FIG. 14 (SEQ ID NO: 6).

3. A DNA sequence according to claim 1, which further comprises a promoter sequence and a terminator sequence.

4. A DNA sequence according to claim 3, which comprises a DNA sequence (SEQ ID NO: 5) shown in FIG. 13.

5. A DNA sequence comprising a gene which encodes a cycloheximide-resistant L41 protein having an amino acid sequence shown in FIG. 14 (SEQ ID NO: 6) wherein glutamine is substituted for proline at position 56.

6. A plasmid comprising the DNA sequence according to claim 5.

7. A DNA fragment of about 13.5 kb which is represented by the restriction enzyme map in FIG. 6(b) and comprises an rRNA gene group of *Candida utilis*, or a partial DNA sequence thereof.

8. A DNA sequence comprising repeated units of the about 13.5 kb DNA fragment according to claim 7.

9. A plasmid comprising the DNA sequence according to claim 7.

10. A DNA sequence comprising a gene sequence encoding orotidine-5'-phosphate decarboxylase (URA3) protein which was isolated from *Candida utilis* and which complements the ura3 mutation of *Saccharomyces cerevisiae*.

11. A DNA sequence according to claim 10, wherein the URA protein comprises an amino acid sequence shown in FIGS. 10 and 11 (SEQ ID NO: 4).

12. A DNA sequence according to claim 10 which comprises the DNA sequence shown in FIG. 9 (SEQ ID NO: 3) or a partial sequence thereof which complements the ura3 mutation of *Saccharomyces cerevisiae*.

13. A plasmid comprising the DNA sequence according to claim 12.

14. A phosphoglycerate kinase (PGK) gene promoter sequence of *Candida utilis*.

15. A PGK gene promoter sequence according to claim 14, which comprises a sequence having at least nucleotides 946–1346 of the sequence shown in FIG. 3 (SEQ ID NO: 2) or a partial sequence thereof which retains the PGK gene promoter activity.

16. A PGK gene terminator sequence of *Candida utilis*.

17. A PGK gene terminator sequence according to claim 16, which comprises the DNA sequence shown in FIG. 2 (SEQ ID NO: 1) or a partial sequence thereof which retains the PGK gene terminator activity.

18. A gene expression unit comprising a PGK gene promoter sequence of *Candida utilis* and a PGK gene terminator sequence of *Candida utilis*.

19. A plasmid comprising the gene expression unit according to claim 18.

20. A plasmid according to claim 19, which is a plasmid pPGKPT3, pPGKPT4, or pPGKPT5.

21. A DNA sequence comprising a PGK gene promoter sequence of *Candida utilis* functionally linked to a heterologous gene sequence.

22. A DNA sequence according to claim 21, further comprising a PGK gene terminator sequence linked downstream of the heterologous gene.

23. A glyceraldehyde-3-phosphate dehydrogenase (GAP) gene promoter sequence of *Candida utilis*.

24. A GAP gene promoter sequence according to claim 23, which comprises the DNA sequence shown in FIG. 30 (SEQ ID NO: 7) or a partial sequence thereof which retains the GAP gene promoter activity.

25. A GAP gene terminator sequence of *Candida utilis*.

26. A GAP gene terminator sequence according to claim 25, which comprises the DNA sequence shown in FIG. 31 (SEQ ID NO: 8) or a partial sequence thereof which retains the GAP gene terminator activity.

27. A gene expression unit comprising a GAP gene promoter sequence of *Candida utilis*, and a GAP gene terminator sequence of *Candida utilis*.

28. A plasmid comprising the gene expression unit according to claim 27.

29. A plasmid according to claim 26, which is a plasmid pGAPPT1 or pGAPPT2.

30. A DNA sequence comprising a GAP gene promoter sequence of *Candida utilis* functionally linked to a heterologous gene sequence.

31. A DNA sequence according to claim 30 further comprising a GAP gene terminator sequence of *Candida utilis* linked downstream of the heterologous gene.

32. A plasma membrane proton ATPase (PMA) gene promoter sequence of *Candida utilis*.

33. A PMA gene promoter sequence according to claim 32, which comprises the DNA sequence shown in FIG. 34 (SEQ ID NO: 9), or a partial sequence thereof which retains the PMA gene promoter activity.

34. A PMA gene terminator sequence of *Candida utilis*.

35. A PMA gene terminator sequence according to claim 34, which comprises the DNA sequence shown in FIG. 35 (SEQ ID NO: 10), or a partial sequence thereof which retains the PMA gene terminator activity.

36. A gene expression unit comprising a PMA gene promoter sequence of *Candida utilis* and a PMA gene terminator sequence of *Candida utilis*.

37. A plasmid comprising the gene expression unit according to claim 36.

38. A plasmid according to claim 37, which is a plasmid pMAPT1.

39. A DNA sequence comprising a PMA gene promoter sequence of *Candida utilis* functionally linked to a heterologous gene sequence.

40. A DNA sequence according to claim 39, further comprising a PMA gene terminator sequence of *Candida utilis* linked downstream of the heterologous gene.

41. A process for expressing a heterologous gene, which comprises the steps of:
transforming a host cell with a DNA sequence according to any one of claims 21, 30 and 39, and
culturing the transformant cell to express the heterologous gene.

42. A process for expressing a heterologous gene according to claim 41, wherein the host cell is yeast.

43. A process for expressing a heterologous gene according to claim 42, wherein the host cell is *Candida utilis*.

44. A circular integration vector comprising a sequence homologous to a portion of the chromosomal DNA of *Candida utilis* ("homologous DNA sequence"), and a marker gene for selecting a transformant, and optionally a heterologous gene, wherein the heterologous gene is incorporated into the chromosomal DNA of *Candida utilis* by homologous recombination when the vector is cut within the homologous DNA sequence with a restriction enzyme into a linear form and introduced into *Candida utilis*.

45. A vector according to claim 44, wherein both ends of a DNA sequence comprising said marker gene and said optional heterologous gene are covalently linked to said homologous DNA sequence, and wherein the heterologous gene is incorporated into the chromosomal DNA of *Candida utilis* by homologous recombination when the vector is cut within the homologous DNA sequence with a restriction enzyme into a linear form and introduced into *Candida utilis*.

46. A vector according to claim 44, wherein said homologous DNA sequence is selected from a group comprising (a) a gene sequence encoding ribosomal protein L41 of *Candida utilis* and (b) a DNA sequence which confers resistance to cycloheximide to yeast and encodes a cycloheximide-resistant L41 protein having an amino acid sequence shown in FIG. 14 (SEQ ID NO: 6) wherein glutamine is substituted for proline at position 56, and (c) a partial DNA sequence of either (a) or (b).

47. A vector according to claim 44, wherein said homologous DNA sequence comprises a DNA fragment of about 13.5 kd which is represented by a restriction enzyme map in FIG. 6(b) and comprises an rRNA gene group of *Candida utilis* or a partial DNA sequence thereof.

48. A circular integration vector according to claim 44, wherein said homologous DNA sequence comprises a gene sequence encoding orotidine-5'-phosphate decarboxylase (URA3), which was isolated from *Candida utilis* and which complements the ura3 mutation of *Saccharomyces cerevisiae* or a partial DNA sequence thereof.

49. A circular integration vector according to claim 44, wherein said homologous DNA sequence comprises the PGK gene sequence.

50. A circular integration vector according to claim 44, wherein said homologous DNA sequence comprises the GAP gene sequence.

51. A circular integration vector according to claim 44, wherein said homologous DNA sequence comprises the PMA gene sequence.

52. A circular integration vector according to claim 44, wherein the marker gene is a drug-resistance gene.

53. A circular integration vector according to claim 52, wherein the drug-resistance marker gene is a cycloheximide-resistance gene.

54. A circular integration vector according to claim 53, wherein the cycloheximide-resistance gene is a cycloheximide-resistance L41 gene.

55. A circular integration vector according to claim 54, wherein the cycloheximide-resistance L41 gene encodes a protein having an amino acid sequence shown in FIG. 14 (SEQ ID NO: 6), wherein glutamine is substituted for proline at position 56.

56. A circular integration vector according to claim 52, wherein the marker gene is a drug-resistance marker gene functionally linked to a *Candida utilis* compatible promoter.

57. A circular integration vector according to claim 56, wherein the drug-resistance marker gene is an G418 antibiotic resistance gene.

58. A vector according to claim 57, wherein the G418 antibiotic resistance gene is an aminoglycoside-3'-phosphotransferase (APT) gene isolated from bacterial transposon Tn903.

59. A circular integration vector according to claim 56, wherein the drug-resistance marker gene is an antibiotic hygromycin resistance gene.

60. A vector according to claim 59, wherein the hygromycin B antibiotic resistance gene is a hygromycin B phosphotransferase (HPT) gene isolated from a plasmid in *E. Coli*.

61. A vector according to claim 44, comprising a heterologous gene operably linked to a *Candida utilis* compatible promoter sequence, and, optionally, functionally linked to a transcription termination sequence.

62. A vector according to claim 61, wherein the promoter sequence or the transcription termination sequence is isolated from *Candida utilis*.

63. A vector according to claim 62, wherein the promoter sequence is a promoter sequence of a phosphoglycerate kinase gene of *Candida utilis*, a glyceraldehyde-3-phosphate dehydrogenase gene of *Candida utilis*, or a plasma membrane proton ATPase gene of *Candida utilis*, and the terminator sequence is a terminator sequence of a phosphoglycerate kinase gene of *Candida utilis*, a glyceraldehyde-3-phosphate dehydrogenase gene of *Candida utilis*, or a plasma membrane proton ATPase gene of *Candida utilis*.

64. A method for transforming *Candida utilis*, which comprises the steps of:

transforming *Candida utilis* with a vector according to claim 44, and selecting a transformant which has become drug-resistant.

65. A method according to claim 64, wherein the DNA sequence of said vector is introduced in the chromosome of *Candida utilis*.

66. A method according to claim 65, wherein multiple copies of the vector DNA sequences are introduced into the chromosome of *Candida utilis*.

67. A method according to claim 64, wherein the vector comprises a cycloheximide-resistance L41 gene as a marker gene.

68. A method according to claim 64, wherein the vector comprises an rDNA sequence.

69. A method according to claim 65, wherein the vector DNA sequence is introduced in the URA3 gene locus, the L41 gene locus, the PGK gene locus, the GAP gene locus, or the PMA gene locus.

70. A method according to claim 64, wherein said *Candida utilis* transformant is selected from the group consisting of ATCC 9256, ATCC 9226 and ATCC 9950.

71. A method according to claim 64, wherein the transforming step is carried out by the electric pulse method.

72. A method according to claim 71, wherein the electric pulse condition comprises the viable cell ratio in the range of 10–40% and the time constant in the range of 10–20 milliseconds.

73. A DNA fragment at least 1.8 kb long having an autonomous replicability which can maintain a vector containing said DNA fragment as an extrachromosomal element in *Candida utilis*, said vector further characterized by its ability to transform a host at high frequency.

74. A DNA fragment according to claim 73, wherein said autonomous replication DNA fragment is isolated from yeast.

75. A DNA fragment according to claim 74, wherein said autonomous replication DNA fragment is isolated from yeast.

76. A DNA fragment, wherein said autonomously replicable DNA fragment comprises a DNA sequence shown in FIGS. 41 and 42 (SEQ ID NO: 11) or a partial sequence thereof which retains an autonomous replicability.

77. A DNA fragment, wherein said autonomously replicable DNA fragment comprises a DNA sequence shown in FIGS. 43 and 44 (SEQ ID NO: 12) or a partial sequence thereof which retains an autonomous replicability.

78. A vector for transformation of *Candida utilis*, comprising:

a DNA fragment which imparts upon said vector autonomous replicability and which enhances the transformation frequency of the host selected from the group comprising:

the DNA fragment shown in FIGS. 41 and 42 (SEQ ID NO: 11) or a functional fragment thereof; and the DNA fragment shown in FIGS. 43 and 44 (SEQ ID NO: 12) or a functional fragment further thereof.

79. A vector according to claim 78, which comprises a drug-resistance marker gene functionally connected to a *Candida utilis* compatible promoter.

80. A method for transforming a yeast *Candida utilis*, comprising the steps of:

introducing into *Candida utilis* a vector according to claim 79;

selecting a transformant comprising said vector; and further selecting a transformant in which said vector is incorporated into the chromosome.

81. A method for isolating a *Candida utilis* transformant in accordance with claim 80, wherein said vector incorporated into the chromosome is free of a selectable marker gene comprising the further step of culturing the transformant obtained by the method of claim 80 under a non-selectable condition.

82. A process according to claim 80, wherein the DNA fragment having at its both terminals homologous DNA sequences comprises a heterologous gene.

83. A vector comprising a DNA sequence containing a heterologous gene and a sequence homologous to the chromosomal DNA of *Candida utilis* ("homologous DNA sequence") and a marker gene, wherein said heterologous gene is incorporated into the chromosomal DNA of *Candida utilis* by homologous recombination when the vector is cut within the homologous DNA sequence with a restriction enzyme into a linear form.

84. A vector according to claim 83, wherein the homologous DNA sequence is a DNA sequence comprising: a gene sequence encoding ribosomal protein L41 of *Candida utilis*; an about 13.5 kb DNA fragment which is represented by a restriction enzyme map in FIG. 6(*b*) and comprises an rRNA gene group of *Candida utilis* or a partial DNA sequence thereof; a DNA sequence comprising repeated units of said about 13.5 kb DNA fragment; a DNA sequence comprising a gene sequence encoding orotidine-5'-phosphate decarboxylase (URA3) protein, which is isolated from *Candida utilis* and which complements the ura3 mutation *Saccharomyces cerevisiae*; the PGK gene sequence; the GAP gene sequence; the PMA gene sequence and a partial DNA sequence thereof.

85. A transformant of *Candida utilis* which is transformed with a DNA sequence containing a heterologous gene.

86. A transformant of *Candida utilis* transformed with a vector according to claim 83.

87. A transformant of *Candida utilis* according to claim 86 which is free of a selectable marker gene.

88. A transformant *Candida utilis* according to claim 85, wherein said *Candida utilis* transformant is selected from the group consisting of ATCC9256, ATCC9226, and ATCC9950.

89. A process for preparing a peptide encoded by a heterologous gene, comprising the steps of:

culturing a *Candida utilis* transformant according to claim 85, and isolating an expressed peptide encoded by the heterologous gene from said culture, and purifying the peptide.

90. A vector according to claim 79, wherein the drug-resistance gene is free of a promoter sequence.

91. A plasmid according to claim 90, wherein the drug-resistance gene is the APT gene which is the G418-resistance gene isolated from bacterial transposon Tn903.

92. A plasmid according to claim 91, which is a plasmid pPCV2.

93. A Method for isolating DNA having a transcriptional promoter activity comprising the steps of:

transforming *Candida utilis* with a DNA library in which a DNA fragment partially digested with a restriction enzyme is cloned at the 5'-end of the drug-resistance gene of the plasmid according to claim 90, selecting a transformant which will be drug-resistant, and isolating from a plasmid recovered from the transformant a DNA fragment which functions in *Candida utilis* as a transcriptional promoter.

94. A process according to claim 93, wherein the DNA partially digested with a restriction enzyme is a chromosomal DNA of *Candida utilis*.

95. A DNA fragment having a transcriptional promoter activity in *Candida utilis* obtainable by the process according to claim 93.

96. A DNA fragment according to claim 95, which is isolated from a chromosome by digestion with AluI, HaeIII or RsaI, or a combination thereof, and has a length of 0.8–1.8 kb.

97. A DNA sequence comprising a heterologous gene and a promoter sequence selected from the group consisting of a DNA fragment according to claim 95, a DNA fragment comprising the base sequence shown in FIG. 48 (SEQ ID NO: 13) and a partial sequence of said DNA fragment comprising said base sequence, wherein said promoter sequence has a transcriptional promoter activity in *Candida utilis* and wherein said heterologous gene is operably linked downstream of said promoter sequence.

98. A process for expressing a heterologous gene comprising the steps of:

transforming a host cell with the DNA sequence according to claim 97, and culturing said transformant cell to express the heterologous gene.

99. A process for expressing a heterologous gene according to claim 98, wherein the host cell is *Candida utilis*.

100. A transformant of *Candida utilis* transformed with a vector according to claim 44.

101. A DNA fragment comprising the base sequence shown in FIG. 48 (SEQ ID NO: 13) or a partial sequence thereof which has a transcriptional promoter activity in *Candida utilis*.

* * * * *